(12) United States Patent
Combs et al.

(10) Patent No.: US 8,796,319 B2
(45) Date of Patent: Aug. 5, 2014

(54) 1,2,5-OXADIAZOLES AS INHIBITORS OF INDOLEAMINE 2,3-DIOXYGENASE

(75) Inventors: Andrew P. Combs, Kennett Square, PA (US); Eddy W. Yue, Landenberg, PA (US); Richard B. Sparks, Boothwyn, PA (US); Wenyu Zhu, Media, PA (US); Jiacheng Zhou, Newark, DE (US); Qiyan Lin, Newark, DE (US); Lingkai Weng, Malvern, PA (US); Tai-Yuen Yue, Hockessin, DE (US); Pingli Liu, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 13/294,711

(22) Filed: Nov. 11, 2011

(65) Prior Publication Data

US 2012/0058079 A1 Mar. 8, 2012

Related U.S. Application Data

(62) Division of application No. 12/498,782, filed on Jul. 7, 2009, now Pat. No. 8,088,803.

(60) Provisional application No. 61/078,876, filed on Jul. 8, 2008, provisional application No. 61/150,873, filed on Feb. 9, 2009.

(51) Int. Cl.
*A61K 31/4245* (2006.01)
*C07D 413/12* (2006.01)
*C07D 271/08* (2006.01)

(52) U.S. Cl.
CPC .......... *A61K 31/4245* (2013.01); *C07D 413/12* (2013.01); *C07D 271/08* (2013.01)
USPC .......................................... 514/364; 548/125

(58) Field of Classification Search
CPC . C07D 271/08; C07D 413/12; A61K 31/4245
USPC .......................................... 514/364; 548/125
See application file for complete search history.

(56) References Cited

U.S. PATENT DOCUMENTS

| | | | |
|---|---|---|---|
| 3,236,855 A | 2/1966 | Jones et al. | |
| 3,553,228 A | 1/1971 | Freedman et al. | |
| 3,948,928 A | 4/1976 | Nishimura et al. | |
| 4,116,974 A | 9/1978 | Farge et al. | |
| 4,323,681 A | 4/1982 | Wolf et al. | |
| 4,699,916 A | 10/1987 | Sirrenberg et al. | |
| 5,364,864 A | 11/1994 | Bigg et al. | |
| 5,712,294 A | 1/1998 | Robert et al. | |
| 6,482,416 B2 | 11/2002 | Munn et al. | |
| 6,482,822 B1 | 11/2002 | Bigg et al. | |
| 6,780,858 B2 | 8/2004 | Li et al. | |
| 7,144,902 B1 | 12/2006 | Baucke et al. | |
| 8,008,281 B2 | 8/2011 | Prendergast et al. | |
| 8,034,953 B2 | 10/2011 | Combs et al. | |
| 8,088,803 B2 | 1/2012 | Combs et al. | |
| 8,372,870 B2 | 2/2013 | Combs et al. | |
| 8,377,976 B2 | 2/2013 | Combs et al. | |
| 8,450,351 B2 | 5/2013 | Combs et al. | |
| 8,507,541 B2 | 8/2013 | Combs et al. | |
| 2002/0155104 A1 | 10/2002 | Munn et al. | |
| 2004/0234623 A1 | 11/2004 | Munn et al. | |
| 2006/0194802 A1 | 8/2006 | Abdellaoui et al. | |
| 2006/0258719 A1 | 11/2006 | Combs et al. | |
| 2007/0037752 A1 | 2/2007 | Ansorge et al. | |
| 2007/0037785 A1 | 2/2007 | Ansorge et al. | |
| 2007/0038298 A1 | 2/2007 | Sulner et al. | |
| 2007/0185165 A1 | 8/2007 | Combs et al. | |
| 2007/0203140 A1 | 8/2007 | Combs et al. | |
| 2007/0265257 A1 | 11/2007 | Tanaka et al. | |
| 2008/0119491 A1 | 5/2008 | Combs | |
| 2008/0125470 A1 | 5/2008 | Combs et al. | |
| 2008/0146624 A1 | 6/2008 | Combs et al. | |
| 2008/0182882 A1 | 7/2008 | Combs et al. | |
| 2008/0214546 A1 | 9/2008 | Combs et al. | |
| 2008/0214549 A1 | 9/2008 | Shaw et al. | |
| 2009/0163545 A1 | 6/2009 | Goldfarb | |
| 2009/0247586 A1 | 10/2009 | Dunkel et al. | |
| 2011/0165188 A1 | 7/2011 | Combs et al. | |
| 2011/0172279 A1 | 7/2011 | Combs et al. | |
| 2011/0311479 A1 | 12/2011 | Combs et al. | |
| 2013/0123246 A1 | 5/2013 | Combs et al. | |
| 2013/0177590 A1 | 7/2013 | Combs et al. | |

FOREIGN PATENT DOCUMENTS

| | | |
|---|---|---|
| BE | 659467 | 8/1965 |
| CA | 2500113 | 4/2004 |
| DE | 2040628 | 2/1972 |
| EP | 0352832 | 1/1990 |
| EP | 0516520 | 12/1992 |
| EP | 0536424 | 4/1993 |
| EP | 1038874 | 9/2000 |
| EP | 1188747 | 3/2002 |
| JP | 40020710 | 9/1965 |
| JP | 50-050369 | 5/1975 |

(Continued)

OTHER PUBLICATIONS

Clercq, Journal of Clinical Virology, vol. 30, 2004, pp. 115-133.*
Shih et al., Medicinal Research Reviews, vol. 24, 2004, pp. 449-474.*
Luo et al. Cell, 2009, 136, pp. 823-837.*
Graham, B.S., "Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM. pp. I-20-38.*
WebMD entry for Parkinson's Disease Prevention, obtained from http://www.webmd.com/parkinsons-disease/guide/parkinsons-disease-prevention on Jul. 19, 2012.*

(Continued)

*Primary Examiner* — Joseph Kosack
*Assistant Examiner* — Matthew Coughlin
(74) *Attorney, Agent, or Firm* — Fish & Richardson P.C.

(57) ABSTRACT

The present invention is directed to 1,2,5-oxadiazole derivatives, and compositions of the same, which are inhibitors of indoleamine 2,3-dioxygenase and are useful in the treatment of cancer and other disorders, and to the processes and intermediates for making such 1,2,5-oxadiazole derivatives.

68 Claims, 3 Drawing Sheets

(56) References Cited

FOREIGN PATENT DOCUMENTS

| | | |
|---|---|---|
| JP | 58208275 | 12/1983 |
| JP | 60193968 | 10/1985 |
| JP | 62059283 | 3/1987 |
| JP | 02006453 | 1/1990 |
| JP | 4297449 | 10/1992 |
| JP | 06-065269 | 3/1994 |
| JP | 11171702 | 6/1999 |
| JP | 11-513679 | 11/1999 |
| JP | 2000-505815 | 5/2000 |
| JP | 2001158785 | 6/2001 |
| JP | 2001158786 | 6/2001 |
| JP | 2001-233861 | 8/2001 |
| JP | 2002-542165 | 12/2002 |
| RU | 2230742 | 6/2004 |
| SU | 886740 | 12/1981 |
| WO | WO 97/14686 | 4/1997 |
| WO | WO 97/30047 | 8/1997 |
| WO | WO 97/42183 | 11/1997 |
| WO | WO 98/24784 | 6/1998 |
| WO | WO 99/29310 | 6/1999 |
| WO | WO 99/62903 | 12/1999 |
| WO | WO 00/52001 | 9/2000 |
| WO | WO 00/61609 | 10/2000 |
| WO | WO 01/51456 | 7/2001 |
| WO | WO 02/00196 | 1/2002 |
| WO | WO 02/079200 | 10/2002 |
| WO | WO 02/102799 | 12/2002 |
| WO | WO 03/045901 | 6/2003 |
| WO | WO 03/070236 | 8/2003 |
| WO | WO 03/087347 | 10/2003 |
| WO | WO 03/099805 | 12/2003 |
| WO | WO 2004029031 | 4/2004 |
| WO | WO 2004/093871 | 11/2004 |
| WO | WO 2004/094409 | 11/2004 |
| WO | WO 2005/019190 | 3/2005 |
| WO | WO 2005/037257 | 4/2005 |
| WO | WO 2005/037779 | 4/2005 |
| WO | WO 2006/028284 | 3/2006 |
| WO | WO 2006/067532 | 6/2006 |
| WO | WO 2006/122150 | 11/2006 |
| WO | WO 2006/133417 | 12/2006 |
| WO | WO 2007/068377 | 6/2007 |
| WO | WO 2007/075598 | 7/2007 |
| WO | WO 2008/036642 | 3/2008 |
| WO | WO 2008/036643 | 3/2008 |
| WO | WO 2008/036652 | 3/2008 |
| WO | WO 2008/036653 | 3/2008 |
| WO | WO 2008/058178 | 5/2008 |
| WO | WO 2008/073825 | 6/2008 |

OTHER PUBLICATIONS

Cancer Drug Design and Discovery Neidle, Stephen, ed. (Elsevier/Academic Press, 2008) pp. 427-431.*
Gura, Science Nov. 7, 1997: vol. 278. No. 5340, pp. 1041-1042.*
Roberts, Jr et al., JAMA 292(17): 2130-2140 (2004).*
Kamb, Nature Reviews Drug Discovery 4, 161-165 (Feb. 2005).*
Kola, Nature Reviews Drug Discovery 3, 711-715 (2004).*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Inaba et al. Gynecologic Oncology 2009, 115, 185-192.*
Speeckaert et al. European Journal of Cancer, 2012, 48, 2004-2011.*
Feder-Mengus et al. European Journal of Cancer, 2008, 44, 2266-2275.*
A.R. Katritzky et al., "Synthesis of mono and symmetrical di-N-hydroxy- and N-aminoguanidines", Journal of Organic Chemistry, 71(18):6753-8 (2006).
Ait-Mohand, Samia. and Dolbier, Jr. William R., "New and Convenient Method for Incorporation of pentafluorosulfanyl ($SF_5$) Substituents Into Aliphatic Organic Compounds", Organic Letters, 4(17), 3013-3015, 2002.
Andrianov et al. "Degenerate Rearrangement of 3-amino-1,2,5-oxadiazole-4-carboxamidoxime", Khimiya Geterotsiklicheskikh Soedinenii, (1988), (12), 1701 (and abstract Database Hcaplus, on STN, 1989:515108, No. 111:115108).
Andrianov et al., "Acid halides of 4-aminofurazan-3-carbohydroxamic acids", Chemistry of Heterocyclic Compounds, Latvian Institute of Organic Chemistry, vol. 30, 3:370-371 (1994) (English translation of Khimiya Geterotsiklicheskikh Soedinenii, (1994), (3), 420-21) and abstract Database Hcaplus STN File CA, 1995:376582; 123:198702.
Andrianov et al., "Ring formation reactions of 4-aminofurazan-3-carboxyamidoximes", Chemistry of Heterocyclic Compounds, 30(4):470-474 (1993) (English translation of Andrianov et al., "4-aminofurazan-3-carboxamidoxime cyclization", Khimiya Geterotsiklicheskikh Soedinenii (4):534-8 (1994) (and abstract Database Caplus No. 1995:393128; 122:290788).
Andrianov et al., "4-aminofurazan-3-hydroximic halides", Institute of Organic Synthesis, 5:581-585 (1992) translation of "Acid halides of 4-aminofurazan-3-carbohydroximic acid", Khimiya Geterotsiklicheskikh Soedinenii, (1992), (5), 687-91 and abstract Database Hcaplus, on STN, 1993:212973, No. 118:212973.
Andrianov et al., "Rearrangements of 1-oxa-2-azoles. 2. Structure and isomerization of pentamethyleneamidoximes of 4-aminofurazan-3-carboxylic acid", Khimiya Geterotsiklicheskikh Soedinenii, (1991), (1), 122-3 (and abstract Database Hcaplus, STN, 1991:449555, No. 115:49555).
Andrianov et al., "Rearrangements of 5-trifluoromethyl-1,2,4-oxadiazoles by action of ammonia and amines", Institute of Organic Synthesis, Academy of Sciences of the Latvian SSR, p. 707 translation of "Ammonia- and amine-induced rearrangements of 5-(trifluoromethyl)-1,2,4-oxadiazoles", Khimiya Geterotsiklicheskikh Soedinenii, (1988), (6), 856-7 and abstract Database Hcaplus, on STN, 1989:212695, No. 110:212695).
Andrianov et al., "Synthesis and properties of derivatives of 4-aminofuroxan-3-carboxylic acid", Chemistry of Heterocyclic Compounds, 33(8), 973-976 (1997), translation of Khimiya Geterotsiklicheskikh Soedinenii, (1997) No. 8, pp. 1115-1119 and abstract Database Hcaplus, on STN, 1998:221958, No. 128:308445.
Andrianov et al., "Synthesis of furazans by rearrangement of 3-acyl-1-oxa-2-azole oximes", UDC 547.793.07(047) 2611(90):1199-1213 (1991), Institute of Organic Synthesis, Academy of Science of the Latvian SSR, (Translation of Khimiya Geterotsiklicheskikh Soedinenii, (1990) No. 11, pp. 1443-1459).
Andrianov et al., "Synthesis, structure, and rearrangement of 4-aminofurazan-3-carboxamide oximes", UDC 547.793.2, 29(5):877-880 (1994), (translation of Zhurnal Organicheskoi Khimii, (1993), 29(5), 1062-6) and abstract Database Hcaplus, on STN, 1994:270259, No. 120:270259.
Andrianov, et al., "Synthesis and properties of 4-amino-3-cyanofurazan", Chemistry of Heterocyclic Compounds, vol. 30, No. 5, pp. 608-11 (1994), translation of Khimiya Geterotsiklicheskikh Soedinenii, (5), 693-6 (1994) with abstract Database Hcaplus, on STN 1995:374071, No. 123:198701.
Areschka et al., "Studies on the benzofuran series. LXI. 3-Benzofuranylacetamidoximes with antihypertenstive potential", European Journal of Medicinal Chemistry, (1977), 12(1), 87-91 (with English abstract).
Beaudegnies et al., "Synthesis of furazan conjugated new heterocycles", Heterocycles, (2003), 60(11), 2417-2424 and abstract Database Hcaplus, on STN, 2003:865834, No. 140:59538.
Belik et al., "Descriptor v'cp-aided study of the rearrangement of 1-oxa-2-azoles", Zhurnal Organicheskoi Khimii, 30(5), 757-9 (1994) with abstract STN File CA, 122:238877; 1995:326366.
Belik, et al., "Theoretical investigation of rearrangements of 1-oxa-2-azole-3-carboxamidoximes", Russian Journal of Organic Chemistry, 34(4), 543-548 (1998) (Translation of Zhurnal Organicheskoi Khimii 34(4), 577-582) (with abstract STN File CA, 130:209340; 1999:79495).
Berge, et al., "Pharmaceutical Salts", J. of Pharmaceutical Science, vol. 66 No. 1, pp. 1-19 (1977).
Brown, et al., "Implications of Interferon-induced Tryptophan Catabolism in Cancer, Auto-immune Diseases and Aids", Adv. Exp. Med. Biol., 294: 425-35 (1991).

(56) References Cited

OTHER PUBLICATIONS

Burger et al., "Janus kinase inhibitor INCB20 has antiproliferative and apoptotic effects on human myeloma cells in vitro and in vivo," Mol. Cancer Ther 2009;8(1) Jan. 2009, 26-35.
Chauhan et al., "Antifilarial profile of substituted pyrazoles: a new class of antifilarial agents," *Indian Journal of Chemistry,* Section B: Organic Chemistry Including Medicinal Chemistry (1993), 32B(8), 858-61 (with abstract Database Hcaplus STN File CA, 120:244819; 1994:244819).
Corbett et al. In vivo methods for screening and preclinical testing. Cancer Drug Discovery and Development: Anticancer Drug Development Guide: Preclinical Screening, Clinical Trials, and Approval, 2nd Ed. Teicher, B.A. and Andrews, P.A., Gumana Press Inc., Totowa, NJ, 2004.
Current Protocols in Immunology, vol. 4, Coligan, J.E., et al; Immunotherapy of Cancer, Human Press, 2006, Disis, M.L.
Database CAPLUS, on STN, 1963: 73272, No. 83, 12528c-e, see RN 90585-88-9 CAPLUS, XP-002467962 dated May 2, 2008, (abstract of Sycheva, et al. "Compaunds with Potential Antitubercular Activity. VI. Amidoximes, amide Hydrazones, and S-Oxides of Thioamides of some Heterocyclic acids", (1962) 32, 3669-74) (1page).
Database CAPLUS, on STN, 1966: 35828, No. 64, 6633a-d, see RN 4698-75-3 CAPLUS, XP-002467245 dated May 2, 2008 (abstract of Sycheva, et al., "Compaunds with Potential Antitubercular Activity. X. Derivatives of Benzoxazole-2-carboxylic acid", (1965) 46-51 (1 page).
Database CAPLUS, on STN, 1975:606233, No. 83: 32463a, 32466a, see RN 55942-51-3 CAPLUS, XP-002467961 dated May 2, 2008 (abstract of Nishimura, Haruki et al., JP Patent No. 50050369, issued May 6, 1975 "Amidoxime Derivatives",) (1 page).
Database CAPLUS, on STN, 1992: 6493, No. 116, 6493, XP-002467964, RN 137890-17-6 dated Jun. 2, 2008, (abstract of Andrianov, et al., "Rearrangements of 1-oxa-2-azoles. 4. synthesis and rearrangement of Amidoximes of soxazole-and 4,5-dihydrosoxazole-3-carboxylic acid", (1991) (6), 827-32) (1 page).
Daubener, et al., "IFNγ Activated Indoleamine 2,3-Dioxygenase Activity In Human Cells Is An Antiparasitic and an Antibacterial Effector Mechanism", Adv. Exp. Med. Biol., 467: 517-24 (1999).
Deeb et al., "Heterocyclic synthesis from 3-amino-4-cyanopyrazole," Collection of Czechoslovak Chemical Communications (1990), 55(3), 728-33 (with abstract Database Hcaplus STN File CA, 113:97502; 1990:497502).
Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci, USA.* 90:3539-3543 (1993).
El-Mobayed et al., "Synthesis of heterocyclic compounds containing nitrogen and sulfur from 3-amino-4-cyanopyrazole," *Journal of the Chemical Society of Pakistan* (1989), 11(4), 287-90 (with abstract Database Hcaplus STN File CA, 113:231330; 1990:631330).
Friberg, M., Jennings, R., et al. Indoleamine 2,3-dioxygenase contributes to tumor cell evasion of T cell-mediated rejection. Int. J. Cancer: 101:151-155, 2002.
Fujii, et al., "Antitumor activities of some fifty compounds related to adenine derivatives," Yakugaku Zasshi (1977), 97(6), 689-91(with abstract Database Hcaplus STN File CA, 87:111278; 1977:511278).
Fujii et al., "Purines. XLVIII. Syntheses and proton nuclear magnetic resonance study of 2-deuterioadenines substituted or unsubstituted at the 9-position and of their N-oxygenated derivatives," Chemical & Pharmaceutical Bulletin (1991), 39(2), 301-8 (with abstract Database Hcaplus STN File CA, 114:247645; 1991:247645).
Fujii et al., "Purines. XV. Conversion of N,9-dimethyladenine into the 1,9-dimethyl isomer. Reverse operation of the dimroth rearrangement," Chemical & Pharmaceutical Bulletin (1974), 22(10), 2211-16 (with abstract Database Hcaplus STN File CA, Abstract 82:43349; 1975:43349).
Fujii et al., "Purines. V. Dimroth rearrangement of 1-alkoxyadenines. Synthesis of N-alkoxyadenines," Chemical & Pharmaceutical Bulletin (1971), 19(8), 1731-4 (with abstract Database Hcaplus STN File CA, Abstract 75:110279; 1971:510279).
Fujii et al., "Purines. III. Rearrangement of 1-alkoxy-9-alkyladenines to 6-alkoxyamino-9-alkylpurines through isolatable N'-alkoxy-1-alkyl-5-formamidoimidazole-4-carboxamidines ," Tetrahedron (1971), 27(12), 2415-23 (with abstract Database Hcaplus STN File CA, Abstract 75:76739; 1971:476739).
Fujii et al., "Oxidation of N6-benzyladenine with m-chloroperoxybenzoic acid: formation of the N(1)-oxide," Heterocycles (1994), 37(1), 219-22 (with abstract Database Hcaplus STN File CA, 121:35143; 1994:435143).
Greene, et al., Protective Groups in Organic Synthesis, 2d. Ed., Wiley & Sons, 1991.
Grohmann, et al., "Tolerance, DCs and tryptophan: much ado about IDO", Trends Immunol., 24: 242-8 (2003).
Higuchi et al., "Pro-drugs as Novel Delivery Systems," vol. 14 of the A.C.S. Symposium Series Bioreversible Carriers in Drug Design, ed. Edward B. Roche, American Pharmaceutical Association and Pergamon Press, 1987.
Hwu P, et al., "Indoleamine 2,3-dioxygenase production by human dendritic cells results in the inhibition of T cell proliferation", *J. Immunol.* 164(7):3596-9, (2000).
Ichikawa, T. et al., "A new synthesis of adenine and 4-aminoimidazole-5-carboxamide", Central Research Laboratories, Ajinomoto Co., Inc., pp. 253-255 (1965).
Itaya et al., "Purines. XVIII. Kinetic studies of the Dimroth rearrangement of 1-alkoxy-9-methyladenines and 1-benzyloxyadenosine. Effect of 1-benzyloxy and 9-β-D-ribofuranosyl groups on the rates of the ring opening and the reclosure," *Chemical & Pharmaceutical Bulletin* (1975), 23(11), 2643-53 (with abstract Database Hcaplus STN File CA, Abstract 84:44592; 1976:44592).
Itaya et al., "Purines. LXXII. Oxidation of N6-alkyladenines with m-chloroperoxybenzoic acid leading to N6-alkyladenine 1-oxides," *Chemical & Pharmaceutical Bulletin* (1996), 44(5), 967-971, (with abstract Database Hcaplus STN File CA, 125:86583; 1996:325165; CAS RN 155720-89-1).
Itaya et al., "Purines. LXXV. Dimroth rearrangement, hydrolytic deamination, and pyrimidine-ring breakdown of 7-alkylated 1-alkoxyadenines: N(1)-C(2) versus N(1)-C(6) bond fission," *Chemical & Pharmaceutical Bulletin* (1997), 45(5), 832-841(with abstract Database Hcaplus STN File CA, 127:65632, 1997:349657).
Ji, et al., "Provision of Granulocyte-Macrophage Colony-Stimulating Factor Converts an Autoimmune Response to a Self-Antigen into an Antitumor Response", *J. Immunol,* 2005, 175:1456-63.
Koblish, et al., "Hydroxyamidine Inhibitors of Indoleamine-2,3-dioxygenase Potently Suppress Systemic Tryptophan Catabolism and the Growth of IDO-Expressing Tumors", *Molecular Cancer Therapeutics,* 9(2):489-498 (Published Online Feb. 2, 2010 at 10.1158/11535-7163.MCT-09-0628).
Koblish, et al., "Potent, Orally Active Hydroxylamidine Inhibitors of Indoleamine-2,3-dioxygenase Suppress Growth of IDO1-expressing Tumors through Systemic Inhibition of Tryptophan Catabolism", 24th Annual Meeting of the International Society for the Biological Therapy of Cancer (ISBTC) in National Harbor MD/Washington DC (Oct. 30, 2009) (poster—1 page) and abstract *J. Immunother.* vol. 32, No. 9 (2009) p. 1005.
Kocevar et al., "Some new synthetic approaches for the preparation of pteridine 3-oxides and pteridines," *Heterocycles* (1981), 15(1), 293-6 (with abstract Database Hcaplus STN File CA, 94:121470; 1981:121470).
Kocevar et al., "New synthetic approach for pyrazolo[3,4-b] pyrazines and isoxazolo[4,5-b] pyrazines," *Heterocycles* (1982), 19(2), 339-42 (with abstract Database Hcaplus STN File CA, 96:162655; 1982:162655).
Kocevar et al., "Neighboring group participation in formation of condensed azines. Formation of pyrazolo[3,4-b]pyrazines, isoxazolo[4,5-b]pyrazines and isothiazolo[5,4-b]pyridine. Heterocycles. CCX," Monatshefte fuer Chemie (1982), 113(6-7), 731-44 (with abstract Database Hcaplus STN File CA, 97:182276; 1982:582276).

(56) References Cited

OTHER PUBLICATIONS

Kocevar et al., "Simple Procedure for the Synthesis of Pyridinecarbohydroximoyl Chlorides and Bromides", Synth. Commun., 18(12), 1427-1432 (1988).

Liu et al., "Estimation and prediction on heats of formation for nitro furazan series compounds with new molecular subgraph", Huaxue Wuli Xuebao, (2002), 15(5), 351-356 and abstract Database Hcaplus, on STN, 2002:880171, No. 138:204550.

Liu, et al., "INCB024360, a Potent and Selective Inhibitor of Indoleamine 2,3-dioxygenase (IDO1) as a Novel Cancer Immunotherapeutic Agent", Mol Cancer Ther, 8(12 Suppl):Poster #C106 (2009).

Liu, et al., "Indoleamine 2,3-Dioxygenase, an Emerging Target for Anti-Cancer Therapy", Current Cancer Drug Targets, 9:938-952 (2009).

Logan, et al., "HeLa cells cocultured with peripheral blood lymphocytes acquire an immuno-inhibitory phenotype through up-regulation of indoleamine 2,3-dioxygenase activity", Immunology, 105: 478-87 (2002).

Longo, G., "Dioximes. LXXVIII", Gazzetta Chimica Italiana, (1931), 61, 575-83 (and abstract Database, on STN, 1932:6117, No. 26:6117).

Medawar, "Some immunological and endocrinological problems raised by the evolution of viviparity in vertebrates", Symp. Soc. Exp. Biol. 7: 320-3 8 (1953).

Meyer, Kevin G., "Improved synthesis of 3-aminofurazan-4-carboxylic acid", Organic Preparations and Procedures INt. 36(4):361-362 (2004).

Milletti et al., "New and Original pKa Prediction Method Using Grid Molecular Interaction Fields", Journal of Chemical Information and Modeling, 2007, 47(6), 2172-2181 and abstract Database Hcaplus, on STN, 2007:1104249, No. 148:33199.

Mishnev et al., "Crystal and molecular structure of isomers of the oxime of 3-aminofurazanoyl piperidine", Institute of Organic Synthesis, Latvian Academy of Sciences, pp. 349-352 translation of Zhurnal Struktumoi Khimii, 32(3):45-48 (1991).

Muller et al., "Inhibition of indoleamine 2,3-dioxygenase, an immunoregulatory target of the cancer suppression gene Bin1, potentiates cancer chemotherapy", Nature Med., 11:312-9 (2005).

Munn et al., "Prevention of Allogeneic Fetal Rejection by Tryptophan Catabolism", Science 281: 1191-3 (1998).

Munn et al., "Potential Regulatory Function of Human Dendritic Cells Expressing Indoleamine 2,3-Dioxygenase", Science 297: 1867-70 (2002).

Munn et al., "Expression of indoleamine 2,3-dioxygenase by plasmacytoid dendritic cells in tumor-draining lymph nodes", J. Clin. Invest., 114(2): 280-90 (2004).

Nekrasov et al., "Effect of particular structural features of aminooximes on formation of final products in reactions with 5-aryl-2,3-dihydrofuran-2,3-diones", Russian Journal of Organic Chemistry, (2000), 36(2), 263-268, (Translation of Zhurnal Organicheskoi Khimii, vol. 36, No. 2 (2000) pp. 285-90) and abstract Database Hcaplus, on STN, 2000:643842, No. 133:321845.

Peterson et al., Evaluation of Functionalized Tryptophan Derivatives and related Compounds as Competitive Inhibitors of Indoleamine 2,3-Dioxygenase Med. Chem. Res. 3, 531-544, (1994).

Physicians' Desk Reference (PDR, e.g., 1996 edition, Medical Economics Company, Montvale, NJ) Zh. Org. Chim. (1993), 29, 1062-1066.

Pivina et al., "Comparative characteristic of energy content calculating methods for the furazan series as an example of energetic materials", Propellants, Explosives, Pyrotechnics, (1995), 20(1) 5-10 and abstract Database Hcaplus, on STN, 1995:464236, No. 122:217824.

Poluektova et al., "Generation of cytotoxic T cells against virus-infected human brain macrophages in a murine model of HIV-1 encephalitis", J. Immunol., 168(8):3941-9 (2002).

Potula et al., "Inhibition of indoleamine 2,3-dioxygenase (IDO) enhances elimination of virus-infected macrophages in an animal model of HIV-1 encephalitis", Blood, 106:2382-90 (2005).

Rakitin et al., "Reaction of furoxannitrolic acids with nitrogen tetroxide", Khimiya Geterotsiklicheskikh Soedinenii, (1993), (9), 1283-7 (with abstract Database Hcaplus, on STN, 1994:244883, No. 120:244883).

Rakitin et al., "Synthesis of Furaxanenitrolic acids", N. D. Zelinskii Institute of Organic Chemistry, Russian Academy of Sciences, 117913 Moscow pp. 952-954 (1994), Translated from Khimiya Geterotsiklicheskikh Soedinenii,(1993), (8), 1117-19 (with abstract Database Hcaplus, on STN, 1994:164073, No. 120:164073).

Ravin, Louis J., "Preformulation", Remington's Pharmaceutical Sciences, 17th ed., Mack Publishing Company, Easton, PA., Chapter 76, pp. 1409-1423 (1985).

Riffaud, et al., "Sur les propriétés analgésiques at antiinflammatoires des benzofuryl-2 amidoximes", European Journal of Medicinal Chemistry, Editions Scientifique Elsevier, Paris, Fr., vol. 1796, pp. 577-580, (1982).

Robev et al., "Pharmacological study of newly synthesized 2-phenyl-4-anilinopyrimidine-5-amidoxime," Doklady Bolgarskoi Akademii Nauk (1982), 35(10), 1451-4 (with abstract Database Hcaplus STN File CA, 98:191493; 1983:191493).

Roche, Edward B., Bioreversible Carriers in Drug Design, ed., American Pharmaceutical Association and Pergamon Press, 1987.

Romanova et al., "Synthesis and reactivity of azidomes: III 1-Azido (4-amino-1, 2, 5-oxadiazol-3-yl) aldoxime in the Cycloaddtion Reaction," Russian J. of Org. Chem., 39(4), 574-578 (translation of Zhurnal Organicheskoi Khimii, vol. 39 No. 4, pp. 610-615 (2003)).

Rozhov et al., "Synthesis of 1,2,4-oxadiazole-, pyrrole- and 1,2,3-triazole-substituted (1,2,3-triazol-1-yl)furazans", Mendeleev Communications, 2008, 18(3), 161-163 and abstract Database Hcaplus, on STN, 2008:880463, No. 150:352019.

Sako, "Product class 19: pyridopyrimidines," Science of Synthesis (2004), 16, 1155-1267 (and abstract Database Hcaplus STN File CA, 142:197902; 2004:205975).

Sambrook, J, Russel, D. Molecular Cloning: A laboratory Manual (3rd edition). Cold Spring Harbor Laboratory Press. Cold Spring Harbor, NY, USA. 2001.

Scherle, P., "Characterization of Novel and Potent Inhibitors of the Immunoregulatory Enzyme Indoleamine 2,3-Dioxygenase (IDO) for Use as Cancer Therapy" presented on Mar. 5, 2009 at the Translational Research Cancer Center Consortium annual meeting in Philadelphia, PA.

Search Run STN International "11641284" dated Jan. 16, 2009 (93 pages).

Search Run Jul. 13, 2010/Scifinder, 10 pages.

Search Run Jul. 28, 2009 / HCAPLUS, 95 pgs.

Search Run Jul. 28, 2009/Registry File Compounds, 107 pgs.

Shaposhnikov et al., "New Heterocycles with a 3-Aminofurazanyl Substituent", Russian Journal of Organic Chemistry, (2002), 38(9), 1351-1355, (Translation of Zhurnal Organicheskoi Khimii, (2002), 38(9), 1405-8, and abstract Database Hcaplus, on STN, 2002:953422, No. 138:368816.

Sheremetev et al., "Hydroxylammonium salts of Furazan family", International Annual Conference of ICT (2003), 34th, 101/1-101/10 and abstract Database Hcaplus, on STN, 2003:641413, No. 139:383553.

Sheremetev et al., "Synthesis of secondary and tertiary aminofurazans", Russian Chemical Bulletin 53(3), 596-614 (2004), translation from Izvestiya Akademii Nauk, Seriya Khimicheskaya, 53(3), pp. 569-586 (Mar. 2004) (and abstract Database Caplus No. 2004:589877; 142:219211).

Sherif et al., "Syntheses with heterocyclic β-enaminonitriles. An expeditious synthetic approach to polyfunctionally substituted 5-phenyl-sulfonylthiophenes and their fused derivatives," Monatshefte fuer Chemie (1997), 128(6/7), 687-696 (with abstract Database Hcaplus STN File CA, 127:331458; 1997:619483).

Sinditskii et al., "Study on combustion of new energetic furazans", 29th International Annual Conference of ICT (Jun. 30-Jul. 3, 1998) (Energetic Materials), 170.1-170.11 and abstract Database Hcaplus, on STN, 1998:498929, No. 129:163569.

Sono, et al., "Indoleamine 2,3-Dioxygenase", J. Biol. Chem. 255(4), 1339-1345 (1980).

Spasova et al., "Certain derivatives of pyrazole as potential antimetabolites of 4(5)-amino-imidazole-5(4)-carboxamide,"

(56) References Cited

OTHER PUBLICATIONS

Progress in Chemotherapy, (Antibacterial, Antiviral, Antineoplast.), Proceedings of the 8th International Congress of Chemotherapy Athens 1973, vol. 3, 841-4 (with abstract Database Hcaplus STN File CA, 84:54765; 1976:54765).
Spasova et al., "Inhibition of the growth of L. casei by some pyrazole analogues of 5(4)aminoimidazole-4(5)-carboxamide," Doklady Bolgarskoi Akademii Nauk (1975), 28(11), 1517-20 (with abstract Database Hcaplus STN File CA, Abstract 84:99208; 1976:99208).
STN File CA, Abstract 145:457146 (abstract of Wang et al, "Experimental study on synthesis of 3-amino-4-chloroximinofurazan" Hanneng Cailiao (2005), 13 (Suppl.), 1-3) (1 page).
Takikawa et al., "Mechanism of Interferon-γ Action," J. Biol. Chem. 263(4):2041-8 (1988).
Taylor, et al., "Relationship between Interferon-γ, indoleamine 2,3-dioxygenase, and tryptophan catabolism", FASEB J., 5:2516-22 (1991).
Terness, P et al., "Inhibition of Allogeneic T cell Proliferation by Indoleamine 3,3-Dioxygenase-expressing Dendritic Cells: Mediation of Suppression by Tryptophan Metabolites", J.Exp. med., 196,(4),447-457, (2002).
Tselinskii et al., "Synthesis and reactivity of carbohydroximoyl azides: II. 4-substituted 1,2,5-oxadiazole-3-carbohydroximoylazides and 1-hydroxy-5-(4-R-1,2,5-oxadiazol-3-yl)tetrazoles", Russian Journal of Organic Chemistry, (2001), 37(11), 1638-1642, translation of Zhurnal Organicheskoi Khimii (2001), 37(11), 1708-1712 (with abstract Database Hcaplus, on STN, 2002:200728, No. 137:20337).
Uyttenhove, et al., "Evidence for a tumoral immune resistance mechanism based on tryptophan degradation by indoleamine 2,3-dioxygenase", Nat. Med., 9(10):1269-1274, (2003).
Wieland et al, "Zur Konstitution der polymeren Knallsauren. Pericyanilsaure, Epicyanilsaure und Metacyanilsaure", Eingelaufen am 25 pp. 54-78 (1929).
Wieland et al., "Zur Konstitution der polymeren Knallsauren. X", Aus dem Chem. Laboratorium der Bayr. Akademie der Wissenschaften zu Munchen, Eingelaufen am 23, pp. 43-53 (1929).
Wang et al., "Synthesis of 3-amino-4-aminoximidofurazan and its crystal structure", Hecheng Huaxue, (2006), 14(3), 234-239 (with abstract Database Hcaplus, on STN, 2006:616681, No. 146:206250.
Wang et al., "Furazan-functionalized tetrazolate-based salts: a new family of insensitive energetic materials", Chemistry—A European Journal, 2009, 15(11), 2625-2634 and abstract Database Hcaplus, on STN, 2009:347940, No. 150:518273.
Wang et al., "Crystal structure of 3-amino-4-acylaminoximinofurazan", Chinese Journal of Energetic Materials, translation of Hanneng Cailiao, 14(6), 441-445 (2006) with abstract Database Hcaplus, on STN, 2007:380035, No. 148:382415.
Wang et al. "Synthesis and crystal structure of 3,6-bis(3'-aminofurazan-4-yl)-1,4-dioxa-2,5-diazacyclohexane-2,5-diene", Huaxue Yanjiu Yu Yingyong (2006), 18(12), 1398-1402 (with abstract Database Hcaplus, on STN, 2007:633470, No. 148:561814).
Wang et al., "500 Gram-grade synthesis of 3-amino-4-aminoximinofurazan,"Hanneng Cailiao (2006), 14(1), 27-28 (3 pages); (with Database Hcaplus STN File CA, 145:191465; 2006:477562) (1 page).
Wichers et al., "The role of indoleamine 2,3-dioxygenase (IDO) in the pathophysiology of interferon-α-induced depression", J. Psychiatry Neurosci., 29(1): 11-17 (2004).
Wikipedia, "indoleamine 2,3-dioxygenase"; downloaded on Jan. 16, 2009 http://en.wikipedia.org/wiki/Indoleamine_2,3-dioxygenase (3 pages).
Wirleitner, et al., "Interferon-γ-Induced Conversion of Tryptophan: Immunologic and Neuropsychiatric Aspects", Curr. Med. Chem., 10: 1581-91 (2003).
Yarovenko et al., "New method for the preparation of 5-amino-1,2,4-oxadiazoles", Bulletin of the Academy of Sciences of the USSR, p. 1924, translation of Izvestiya Akademii Nauk SSSR, Seriya Khimicheskaya, (1991), (9), 2166-7 (3 pages); (with abstract Database Hcaplus, on STN, 1992:21001, No. 116:21001) (1 page).

Yarovenko et al., "A convenient synthesis of 3-substituted 5-guanidino-1,2,4-oxadiazoles", Russian Chem. Bulletin, vol. 43, No. 1 pp. 114-117 (1994) translation of Izvestiya Akademii Nauk, Seriya Khimicheskaya, (1994), (1), 118-21 and abstract Database Hcaplus, on STN, 1995:542485, No. 123:55777.
Yarovenko et al., "New synthesis of nitriles enriched with 15N isotope", Russian Chem. Bulletin, vol. 43, No. 3 pp. 402-404 (1994) translation of Izvestiya Akademii Nauk, Seriya Khimicheskaya, (1994), (3), 444-6 and abstract Database Hcaplus, on STN, 1995:542864, No. 123:111224.
Youngdale, Gilbert A. et al., "Synthesis and antifertility activity of 5-(phenoxymethyl)-2-oxazolidinethiones", Journal of Medicinal Chemistry, 9(1), 155-7, 1966.
Yue et al., "Discovery of Potent Competitive Inhibitors of Indoleamine 2,3-Dioxygenase with in Vivo Pharmacodynamic Activity and Efficacy in a Mouse Melanoma Model," J. Med. Chem. vol. 52, No. 23, pp. 7364-7367 (2009).
Zhou, et al., "Synthesis and properties of 3,4-Bis (4'-aminofurazano-3')furoxan", Huozhayao Xuebao, 30(1), 54-56 (2007) and abstract.
Zidarova et al., "Certain derivatives of 3-aminopyrazole-4-carboxylic acid as potential antimetabolites of 4(5)-aminoimidazole-5(4)-carboxamide in microorganisms," Doklady Bolgarskoi Akademii Nauk (1973), 26(3), 419-22 (with abstract Database Hcaplus STN File CA, Abstract 79:74187; 1973:474187).
Notification on the Result of Substantive Examination, National Office of Intellectual Property, No. 60636/SHTT-SC2, Vietnamese Application No. 1-2007-02634, dated Oct. 7, 2009 (3 pages).
Office Action (non-final) mailed Aug. 3, 2009, U.S. Appl. No. 11/430,441 (15 Pages).
Office Action (final) for U.S. Appl. No. 11/641,284 mailed Oct. 21, 2009 (8 pages).
Office Action (final) mailed Jun. 7, 2010, U.S. Appl. No. 11/430,441 (20 Pages).
International Preliminary Report on Patentability for PCT/US2006/17983 dated Nov. 13, 2007 (6 pages).
International Preliminary Report on Patentability for PCT/US2006/048290 dated Jun. 24, 2008 (9 pages).
International Preliminary Report on Patentability for PCT/US2007/078758 dated Mar. 24, 2009 (8 pages).
International Preliminary Report on Patentability for PCT/US2007/003364 dated Aug. 12, 2008 (9 pages).
International Preliminary Report on Patentability for PCT/US2007/078745 dated Mar. 24, 2009 (13 pages).
International Preliminary Report on Patentability for PCT/US2007/078759 dated Mar. 24, 2009 (15 pages).
International Search Report and Written Opinion PCT/US2006/17983 dated Aug. 2, 2006 (12 Pages).
International Search Report and Written Opinion for PCT/US2006/048290 dated Sep. 17, 2007 (15 pages).
International Search Report and Written Opinion for PCT/US2007/003364 dated Sep. 20, 2007 (16 pages).
International Search Report and Written Opinion for PCT/US2007/078745 mailed Jun. 16, 2008 (21 pages).
International Search Report and Written Opinion for PCT/US2007/078759 dated Feb. 6, 2008 (23 pages).
International Search Report and Written Opinion for PCT/US2007/078758 dated Apr. 28, 2008 (12 pages).
International Search Report and Written Opinion PCT/US2009/049794 dated May 6, 2010 (27 Pages).
Eurasia—Search Report for Application No. 200702455 dated Apr. 28, 2008 (1 page).
Extended European Search Report for European Application No. 06759438.2 dated Jun. 5, 2009 (10 pages).
Search Report dated Nov. 12, 2008 and Written Opinion dated Feb. 6, 2009—Singapore Application No. 200717302-4 (18 pages).
Singapore—Final Examination Report, Singapore Patent Application No. 2007/17302-4 dated Sep. 23, 2009 (11 Pages).
Examination Report—EP Patent Application No. 06759438.2 dated Jul. 29, 2010 (4 pages).
Giron, D.J., "Investigations of Polymorphism and Pseudo-Polymorphism in Pharmaceuticals By Combined Thermoanalytical Techniques", J. Therm. Anal. Cal. (2001), 64, pp. 37-60.

(56) References Cited

OTHER PUBLICATIONS

Giron, D.J., "Applications of Thermal Analysis and Coupled Techniques in Pharmaceutical Industry", *J. Therm. Anal. Cal.* (2002), 68, pp. 335-357.

Rodriguez-Spong et al., "General principles of pharmaceutical solid polymorphism: a supramolecular perspective", *Advanced Drug Delivery Review*, (2004), 56, pp. 241-274.

Souillac, et al., Characterization of Delivery Systems, Differential Scanning Calorimetry, pp. 217-218 in Encyclopedia of Controlled Drug Delivery, (1999), John Wiley & Sons, pp. 212-227.

Bagdasarov et al., "Extraction—photometric determination of copper and cobalt with oxime derivatives of benzimidazole", *Zavodskaya Laboratoriya* (1976), 42(2), 143-144 (Non-English Reference), (in U.S. Appl. No. 11/856,982 in Jan. 29, 2010 Office Action—provided with reference).

Schafer et al., "Failure is an option: learning from unsuccessful proof of concept trials", *Drug Discovery Today*, vol. 13, Nos. 21/22, pp. 913-16 (2008).

Horig et al., "From bench to clinic and back: perspective on the 1st IQPC Translational Research Conference", *Journal of Translational Medicine*, 2:44 (2004) pp. 1-8.

Office Action (nonfinal) for U.S. Appl. No. 11/641,284 mailed Jan. 29, 2009 (13 pages).

Office Action (nonfinal) for U.S. Appl. No. 11/641,284 mailed May 7, 2010 (9 pages).

Office Action (final) for U.S. Appl. No. 11/641,284 mailed Dec. 15, 2010 (8 pages).

Office Action (nonfinal) for U.S. Appl. No. 11/856,967 mailed Jan. 19, 2010 (5 pages).

Office Action (final) for U.S. Appl. No. 11/856,967 mailed Sep. 24, 2010 (11 pages).

Office Action (nonfinal) for U.S. Appl. No. 11/856,982 mailed Jan. 29, 2010 (10 pages).

Office Action (final) for U.S. Appl. No. 11/856,982 mailed Sep. 17, 2010 (6 pages).

Office Action (nonfinal) for U.S. Appl. No. 11/430,441 mailed Dec. 9, 2010 (15 pages).

Chilean Patent Office, Application No. 1096-2006, Office Action, Apr. 22, 2007 (2 pages).

State Intellectual Property Office—PR China, Application No. 200680024326-1, Office Action, Jan. 19, 2011 (10 pages).

State Intellectual Property Office—PR China, Application No. 200680024326-1, Office Action, Oct. 23, 2009 (6 pages).

Eurasian Patent Office, Application No. 200702455, Office Action, Oct. 9, 2009 (English translation) (6 pages).

Georgian Patent Office, Application No. AP2006010418, Office Action, Jul. 14, 2009 (English translation) (2 pages).

Malaysian Patent Office, Application No. PI20062122, Office Action, Oct. 18, 2010 (2 pages).

Intellectual Property Office of New Zealand, Application No. 562919, Examination Report, Sep. 17, 2009 (4 pages).

Keith Guillory, "Generation of Polymorphs, Hydrates, Solvates, and Amorphous Solids", in Polymorphism in Pharmaceutical Solids, 183-226 (Harry G. Britain, ed., 1999).

Griesser, "The Importance of Solvates" in Polymorphism in the Pharmaceutical Industry, 211-233 (Rolf Hilfiker, ed., 2006).

Storey, et al., "Automation of Solid Form Screening Procedures in the Pharmaceutical Industry—How to Avoid the Bottlenecks", *Crystallography Reviews*, 10(1):45-46 (2004).

Morissette, et al., "High-Throughput Crystallization: Polymorphs, Salts, Co-Crystals and Solvates", *Adv. Drug Delivery Rev.*, 56:275-300 (2004).

Vippagunta, et al., "Crystalline Forms", Adv. Drug Delivery Rev., 48:3-26 (2001).

Jordan, V. C. Nature Reviews: Drug Discovery, 2, (2003), p. 205.

Lob et al. Nature Reviews: Cancer, 9:445-452 (2009).

Astigiano, et al., Neoplasia, 7(4):390-396 (2005).

Brandacher, et al., *Clin. Cancer Res.*, 12(4):1144-1151 (2006) (abstract).

Hou, et al., Cancer Res 67(2):792-801 (2007).

Ino, et al., *British Journal of Cancer*, 95:1555-1561 (2006).

Munn, et al., *Journal of Clinical Investigation*, 117(5):1147-1154 (2007).

Okamoto, et al., *Clin Cancer Res* 11(16):6030-6039, at 6037-6038 (2005).

Tang, et al., *Zhongguo Shi Yan Xue Ye Xue Za Zhi.* 14(3):539-42 (2006) (Abstract).

Yarovenko et al., *Tetrahedron*, 1990, 46 (11), pp. 3941-3952.

International Preliminary Report on Patentability for PCT/US2009/049794 issued Jan. 11, 2011 (12 pages).

Office Action dated Nov. 8, 2011 for Japanese Patent Appln. No. 2008-511287 with English translation (11 pgs.).

Quan, et al., Expert Opin. Biol. Ther., 8:1705 at 1714 (2008).

Mailankot, et al., "Cell Cycle Arrest by Kynurenine in Lens Epithelial Cells", IOVS, 49:5466-5475 at 5474 (2008).

Pellegrin, et al., "Enhanced enzymatic degradation of tryptophan by indoleamine 2,3-dioxygenase contributes to the tryptophan-deficient state seen after major trauma", *Shock*, 23:209-215 (2005).

Bonda, et al., "Indoleamine 2,3-dioxygenase and 3-hydroxykynurenine modifications are found in the neuropathology of Alzheimer's disease", *Redox Rep.*, 15(4):161-8 (2010).

Kohl, et al., "IDO and clinical conditions associated with depressive symptoms", *Curr. Drug Metab.*, 8:283-7 (2007).

Tan, et al., "Manipulation of indoleamine 2,3 dioxygenase; a novel therapeutic target for treatment of diseases", *Expert Opin. Ther. Targets*, 13:987-1012 (2009).

Wiley-VCH Verlag GmbH & Co. KGaA, Weinheim, "Organic Synthesis: General Remarks", pp. 1-16 (2005).

Office Action—JP Patent Appl. No. 2008-547407 mailed Aug. 21, 2012 (7 pages).

Search Report, Taiwan Application No. 117382 dated Mar. 7, 2012 (English Translation 1 page—Taiwan Search Report 4 pages).

Office Action (non-final) Mexico Application No. MX/1/2007/013977 as communicated to undersigned representative on Nov. 18, 2011 (2 pages).

Feder-Mengus, et al., "High expression of indoleamine 2,3-dioxygenase gene in prostate cancer", *European J. Cancer*, 44 (2008) pp. 2266-2275.

Gasparri, et al., "Critical role of indoleamine 2,3-dioxygenase in tumor resistance to repeated treatments with targeted IFNγ", *Mol. Cancer Ther.*, 7(12) pp. 3859-3866 (2008).

Hoshi et al., "Indoleamine 2,3-dioxygenase is highly expressed in human adult T-cell leukemia/lymphoma and chemotherapy changes tryptophan catabolism in serum and reduced activity", *Leukemia Research*, 33 pp. 29-45 (2009).

Karanikas et al., "Indoleamine 2,3-Dioxygenase (IDO) Expression in Lung Cancer", *Cancer Biology & Therapy*, vol. 6, Issue 8 pp. 1258-1262, (2007).

Riesenberg et al., "Expression of Indoleamine 2,3-Dioxygenase inTumor Endothelial Cells Correlateswith Long-term Survival of Patients with Renal Cell Carcinoma", *Clin. Cancer Res.*, vol. 13 Issue 23 pp. 2993-3002 (2007).

Witkiewicz et al., "Expression of Indoleamine 2,3-Dioxygenase in Metastatic Pancreatic Ductal Adenocarcinoma Recruits Regulatory T Cells to Avoid Immune Detection", *J. Am. Coll. Surg.*, vol. 206, No. 5, pp. 849-856 (May 2008).

Witkiewicz et al., "IDO2 Genotyping and Expression in Pancreatic Cancer", *J. Am. Coll. Surg.*, vol. 208, No. 5 pp. 781-789 (May 2008).

'ClinicalTrials.gov' [online] "A Phase 2 Study of the IDO Inhibitor INCB024360 Versus Tamoxifen for Subjects with Biochemical-recurrent-only EOC, PPC or PTC Following Complete Remission with First-line Chemotherapy," [2013], [retrieved on Jul. 25, 2013] URL:<http://clinicaltrials.gov/ct2/show/NCT01685255?term=incyte&rank=4> 4 pages.

'ClinicalTrials.gov' [online] "A Phase 1/2 Randomized, Blinded, Placebo Controlled Study of Ipilimumab in Combination with INCB024360 or Placebo in Subjects with Unresectable or Metastatic Melanoma," [2012] [retrieved on Jul. 25, 2013] URL: http://clinicaltrials.gov/ct2/show/NCT01604889?term=incyte&rank=8 > 3 pages.

Liu et al., "Selective inhibition of IDO1 effectively regulates mediators of antitumor immunity," *Blood*, 2010, 115:3520-3530.

(56) References Cited

OTHER PUBLICATIONS

Mellman et al., "Cancer immunotherapy comes of age," *Nature*, 2011, 480:480-489.

Newton et al., "Pharmacodynamic assessment of INCB024360, an inhibitor of indoleamine 2,3-dioxygenase 1 (IDO1) in advanced cancer patients," *ASCO Annual Meeting*, 2012, 16 pages.

Nonaka et al., "Indoleamine 2,3-dioxygenase promotes peritoneal dissemination of ovarian cancer through inhibition of natural killercell function and angiogenesis promotion," *Int. J Oncology*, 2011, 38:113-120.

Soliman et al., "Indoleamine 2,3-Dioxygenase: Is it an Immune Suppressor", Cancer J., 16, 354-59 (2010).

Soliman et al., "A phase I study of 1-methyl-D-tryptophan in patients with advanced malignancies," *J Clin Oncol.*, 2012, suppl; abstr 2501.

Taneja et al., "MMTV mouse models and the diagnostic values of MMTV-like sequences in human breast cancer," *Expert Rev Mol Diagn.*, 2009, 9(5):423-440.

Trinh and Hwu, "Ipilimumab in the treatment of melanoma," *Expert. Opin, Biol. Ther.*, 2012, 12(6):773-782.

Office Action—JP Patent Appl. No. 2009-529341 mailed Oct. 16, 2012 (3 pages).

Office Action—JP Patent Appl. No. 2009-529343 mailed Oct. 16, 2012 (4 pages).

Extended European Search Report in EP Application No. 12178315. 3, dated Jan. 18, 2013, 8 pages.

Costa Rican Office Action in CR Application No. 9485, Feb. 11, 2013, 14 pages with English translation).

Andrianov et al., "4-Aminofurazan-3-carbohydroximic acid halides", Khimiya Geterotsiklicheskikh Soedinenii, (1994), (3), 420-5, and abstract.

Wong et al., "Programmed death-1 blockage enhances expansion and functional capacity of human melanoma antigen-specific CTLs," International Immunology, 2007, 19:1223-1234.

Office Action (nonfinal) for U.S. Appl. No. 12/498,782 mailed Jan. 14, 2011 (14 pages).

Office Action (final) U.S. Appl. No. 12/498,782 mailed May 31, 2011 (35 pages).

\* cited by examiner

1,2,5-OXADIAZOLES AS INHIBITORS OF INDOLEAMINE 2,3-DIOXYGENASE

CROSS REFERENCE TO RELATED APPLICATIONS

This application is a divisional of U.S. Ser. No. 12/498,782, filed Jul. 7, 2009 now U.S. Pat. No. 8,088,803, which claims the benefit of U.S. Ser. No. 61/078,876, filed Jul. 8, 2008 and U.S. Ser. No. 61/150,873, filed Feb. 9, 2009, the disclosures of each of which are incorporated herein by reference in their entireties.

FIELD OF THE INVENTION

The present invention is directed to 1,2,5-oxadiazole derivatives which are inhibitors of indoleamine 2,3-dioxygenase and are useful in the treatment of cancer and other disorders, and to processes and intermediates for making the same.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, a depletion of Trp resulting from IDO activity is a prominent gamma interferon (IFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al., 1999, *Adv. Exp. Med. Biol.*, 467: 517-24; Taylor, et al., 1991, *FASEB J.*, 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with inter-leukin-2 (IL2) was believed to result from IDO released by the tumor cells in response to IFNG secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, *Immunology*, 105: 478-87).

Recently, an immunoregulatory role of Trp depletion has received much attention. Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, *Adv. Exp. Med. Biol.*, 294: 425-35). To this end, it has recently been shown that IDO inhibition can enhance the levels of virus-specific T cells and, concomitantly, reduce the number of virally-infected macrophages in a mouse model of HIV (Portula et al., 2005, *Blood*, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, *Symp. Soc. Exp. Biol.* 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppresses T-cell activity and defends itself against rejection, and blocking tryptophan catabolism during murine pregnancy allows maternal T cells to provoke fetal allograft rejection (Munn, et al., 1998, *Science*, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, *Nature Med.*, 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, *Nature Med.*, 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, *Science*, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, *J. Clin. Invest.*, 114 (2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, *Trends Immunol.*, 24: 242-8). In states of persistent immune activation, availability of free serum Trp is diminished and, as a consequence of reduced serotonin production, serotonergic functions may also be affected (Wirleitner, et al., 2003, *Curr. Med. Chem.*, 10: 1581-91).

Interestingly, administration of interferon-α has been observed to induce neuropsychiatric side effects, such as depressive symptoms and changes in cognitive function. Direct influence on serotonergic neurotransmission may contribute to these side effects. In addition, because IDO activation leads to reduced levels of tryptophan, the precursor of serotonin (5-HT), IDO may play a role in these neuropsychiatric side effects by reducing central 5-HT synthesis. Furthermore, kynurenine metabolites such as 3-hydroxy-kynurenine (3-OH-KYN) and quinolinic acid (QUIN) have toxic effects on brain function. 3-OH-KYN is able to produce oxidative stress by increasing the production of reactive oxygen species (ROS), and QUIN may produce overstimulation of hippocampal N-methyl-D-aspartate (NMDA) receptors, which leads to apoptosis and hippocampal atrophy. Both ROS overproduction and hippocampal atrophy caused by NMDA overstimulation have been associated with depression (Wichers and Maes, 2004, *J. Psychiatry Neurosci.*, 29: 11-17). Thus, IDO activity may play a role in depression.

Small molecule inhibitors of IDO are being developed to treat or prevent IDO-related diseases such as those described above. For example, oxadiazole and other heterocyclic IDO inhibitors are reported in US 2006/0258719 and US 2007/0185165. PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

SUMMARY OF THE INVENTION

The present invention provides, inter alia, IDO inhibitors of Formula I:

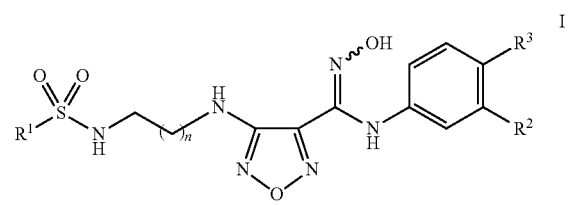

or pharmaceutically acceptable salts thereof, wherein constituent variables are defined herein.

The present invention further provides a pharmaceutical composition comprising a compound of Formula I, and at least one pharmaceutically acceptable carrier.

The present invention further provides a method of inhibiting activity of indoleamine 2,3-dioxygenase comprising contacting the indoleamine 2,3-dioxygenase (IDO) with a compound of Formula I, or a pharmaceutically acceptable salt thereof.

The present invention further provides a method of inhibiting immunosuppression in a patient comprising administering to said patient an effective amount of a compound of Formula I, or a pharmaceutically acceptable salt thereof.

The present invention further provides a method of treating cancer, viral infection, depression, a neurodegenerative disorder, trauma, age-related cataracts, organ transplant rejection, or an autoimmune disease in a patient comprising administering to said patient a therapeutically effective amount of a compound of Formula I, or a pharmaceutically acceptable salt thereof.

The present invention further provides a method of treating melanoma in a patient comprising administering to said patient a therapeutically effective amount of a compound of Formula I, or a pharmaceutically acceptable salt thereof.

The present invention further provides intermediates, processes of preparing the same, and compositions containing the same, which are useful in the preparation of a compound of Formula F15:

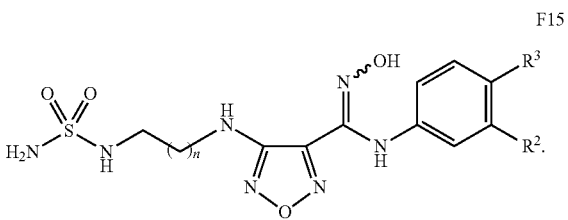

The present invention further provides intermediates, processes of preparing the same, and compositions containing the same, which are useful in the preparation of a compound of Formula F19:

F19

The present invention further provides intermediates, processes of preparing the same, and compositions containing the same, which are useful in the preparation of a compound of Formula F28:

F28

DETAILED DESCRIPTION

The present invention provides, inter alia, IDO inhibitors of Formula I:

I or pharmaceutically acceptable salts thereof; wherein:
$R^1$ is $NH_2$ or $CH_3$;
$R^2$ is Cl, Br, $CF_3$, $CH_3$, or CN;
$R^3$ is H or F; and
n is 1 or 2.
In some embodiments, $R^1$ is $NH_2$.
In some embodiments, $R^1$ is $CH_3$.
In some embodiments, $R^2$ is Cl.
In some embodiments, $R^2$ is Br.
In some embodiments, $R^2$ is $CF_3$.
In some embodiments, $R^2$ is $CH_3$.
In some embodiments, $R^2$ is CN.

In some embodiments, $R^3$ is H.
In some embodiments, $R^3$ is F.
In some embodiments, n is 1.
In some embodiments, n is 2.

The compounds of the present invention can exist in various solid forms. As used herein "solid form" is meant to refer to a solid characterized by one or more properties such as, for example, melting point, solubility, stability, crystallinity, hygroscopicity, water content, TGA features, DSC features, DVS features, XRPD features, etc. Solid forms, for example, can be amorphous, crystalline, or mixtures thereof.

Different crystalline solid forms typically have different crystalline lattices (e.g., unit cells) and, usually as a result, have different physical properties. In some instances, different crystalline solid forms have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the solid form as well as help determine stability and solvent/water content.

Figure 1:
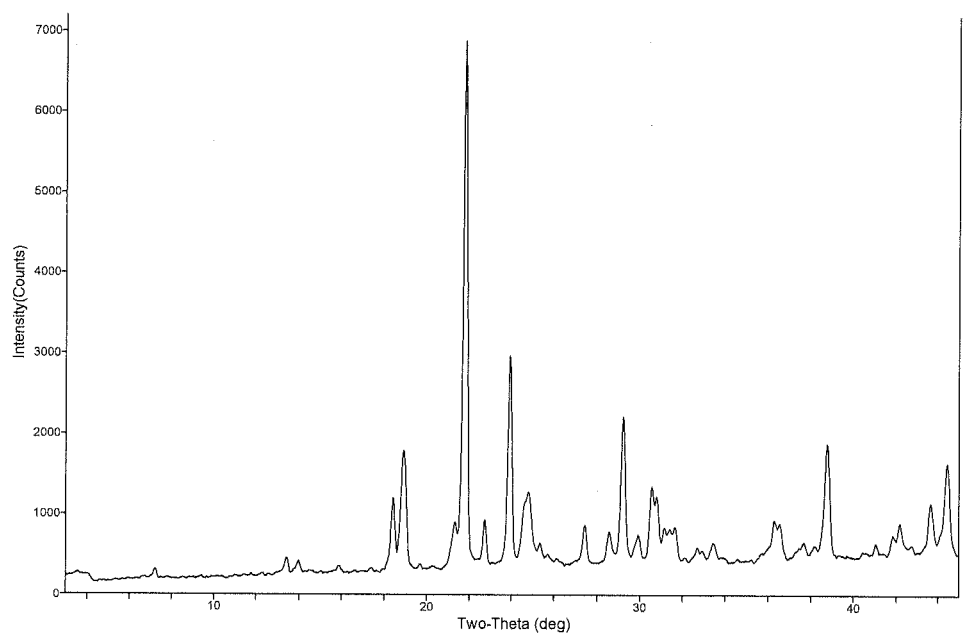
FIG. 1 shows an XRPD pattern characteristic of the compound of the invention prepared in Example 1.
Figure 2:
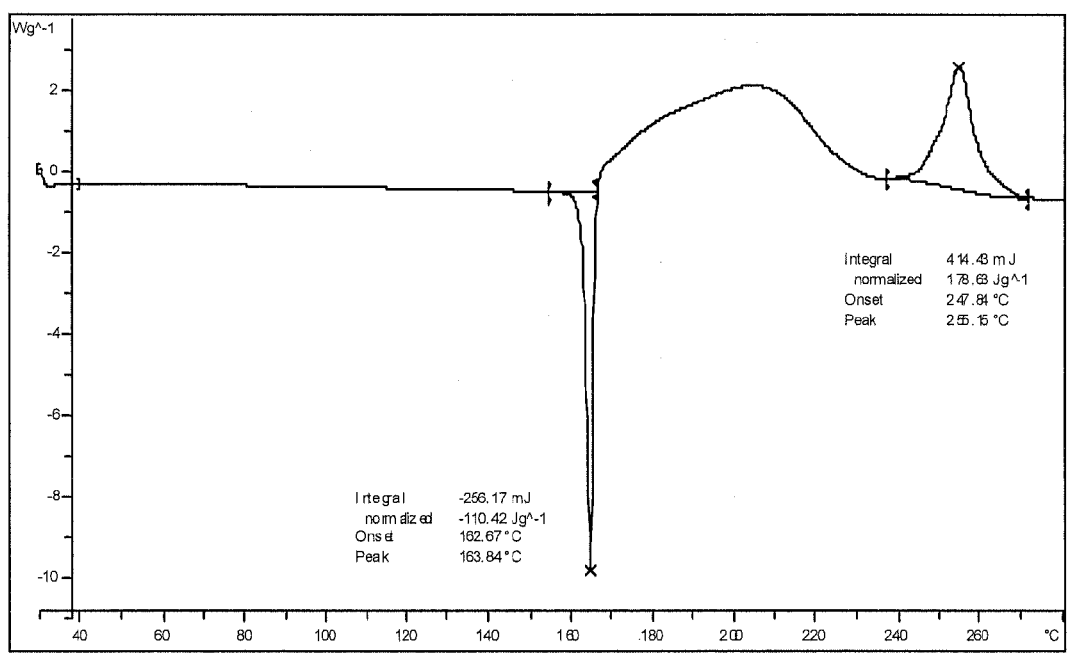
FIG. 2 shows a DSC thermogram characteristic of the compound of the invention prepared in Example 1.

In one aspect, the present invention provides various solid forms of 4-({2-[(aminosulfonyl)amino]ethyl}amino)-N-(3-bromo-4-fluorophenyl)-N'-hydroxy-1,2,5-oxadiazole-3-carboximidamide (see Example 1). In some embodiments, the solid form is a crystalline solid. In some embodiments, the solid form is substantially anhydrous (e.g., contains less than about 1% water, less than about 0.5% water, less than about 1.5% water, less than about 2% water). In some embodiments, the solid form is characterized by a melting point of, or a DSC endotherm centered at, about 162 to about 166° C. In some embodiments, the solid form is characterized by a melting point of, or a DSC endotherm centered at, about 164° C. In some embodiments, the solid form has a DSC thermogram substantially as shown in FIG. 2. In further embodiments, the solid form has at least one, two or three XRPD peaks, in terms of 2-theta, selected from about 18.4°, about 18.9°, about 21.8°, about 23.9°, about 29.2°, and about 38.7°. In further embodiments, the solid form has an XRPD pattern substantially as shown in FIG. 1.

The present invention further provides a composition comprising a solid form of 4-({2-[(aminosulfonyl)amino] ethyl}amino)-N-(3-bromo-4-fluorophenyl)-N'-hydroxy-1,2, 5-oxadiazole-3-carboximidamide (see Example 1). The composition can comprise at least about 50%, at least about 75%, at least about 90%, at least about 95%, or at least about 99% by weight of the solid form. The composition can also contain a pharmaceutically acceptable excipient. In some embodiments, the solid form is substantially purified.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

At various places in the present specification, substituents of compounds of the invention may be disclosed in groups or in ranges. It is specifically intended that the invention include each and every individual subcombination of the members of such groups and ranges.

It is intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The compounds of the invention are further intended to include all possible geometric isomers. Cis and trans geometric isomers of the compounds of the present invention are described and may be isolated as a mixture of isomers or as separated isomeric forms. A bond in a structure diagram represented by a wavy line "∼∼∼" is intended to indicate that the structure represents the cis or the trans isomer, or a mixture of the cis and trans isomers in any proportion.

Compounds of the invention also include tautomeric forms. Tautomeric forms result from the swapping of a single bond with an adjacent double bond together with the concomitant migration of a proton.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, $H_2SO_4$) or organic acid (such as acetic acid, benzoic acid, trifluoroacetic acid) salts of basic residues such as amines; alkali (such as Li, Na, K, Mg, Ca) or organic (such as trialkylammonium) salts of acidic residues such as carboxylic acids; and the like. The salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred.

The "pharmaceutically acceptable salts" of the present invention include a subset of the "salts" described above which are, conventional non-toxic salts of the parent compound formed, for example, from non-toxic inorganic or organic acids. Lists of suitable salts are found in *Remington's Pharmaceutical Sciences,* 17$^{th}$ ed., Mack Publishing Company, Easton, Pa., 1985, p. 1418 and *Journal of Pharmaceutical Science,* 66, 2 (1977), each of which is incorporated herein by reference in its entirety. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Methods of Synthesis

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like) HPLC, or preparative thin layer chromatography; distillation; sublimation, trituration, or recrystallization.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis,* 4$^{th}$ Ed., John Wiley & Sons: New York, 2006, which is incorporated herein by reference in its entirety.

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the reaction step, suitable solvent(s) for that particular reaction step can be selected. Appropriate solvents include water, alkanes (such as pentanes, hexanes, heptanes, cyclohexane, etc., or a mixture thereof), aromatic solvents (such as benzene, toluene, xylene, etc.), alcohols (such as methanol, ethanol, isopropanol, etc.), ethers (such as dialkylethers, methyl tert-butyl ether (MTBE), tetrahydrofuran (THF), dioxane, etc.), esters (such as ethyl acetate, butyl acetate, etc.), halogenated solvents (such as dichloromethane (DCM), chloroform, dichloroethane, tetrachloroethane), dimethylformamide (DMF), dimethylsulfoxide (DMSO), acetone, acetonitrile (ACN), hexamethylphosphoramide (HMPA) and N-methylpyrrolidone (NMP). Such solvents can be used in either their wet or anhydrous forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the invention can be prepared, for example, using the reaction pathways and techniques as described below.

The processes and intermediates of the present invention are useful in the preparation of IDO inhibitors. A general scheme for the preparation of compounds F15 of the invention are described in Scheme 1.

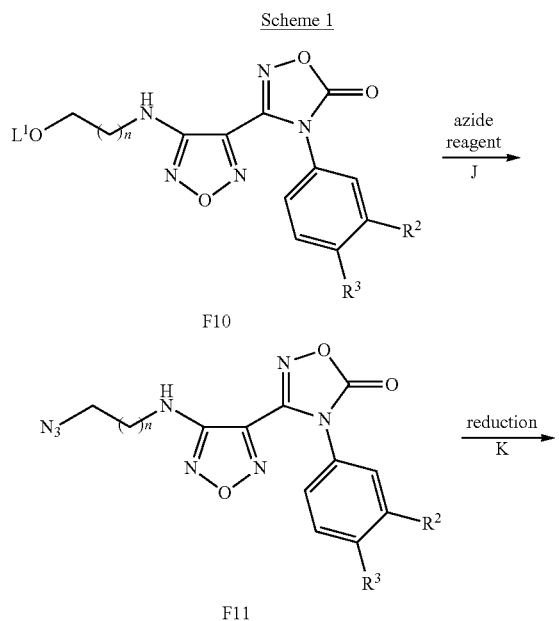

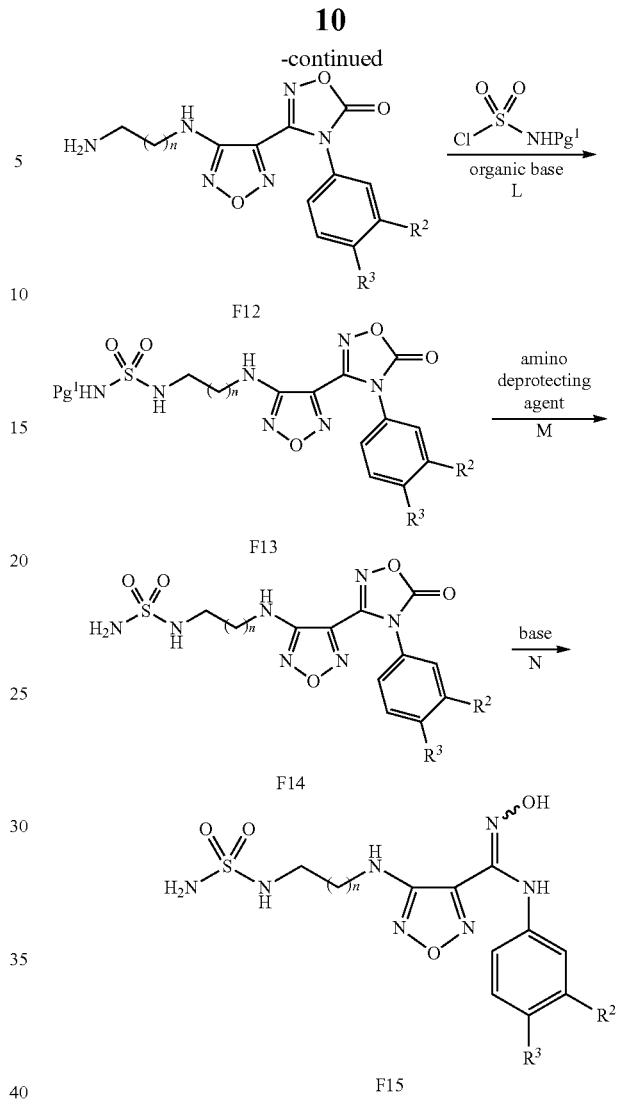

Referring now to Scheme 1, the invention provides a process for preparing a compound of Formula F15, or a salt thereof, wherein $R^2$ is Cl, Br, $CF_3$, $CH_3$, or CN; $R^3$ is H or F; and n is 1 or 2, by reacting a compound of Formula F13, or a salt thereof, wherein $Pg^1$ is an amino protecting group, with an amino deprotecting agent (Step M) to afford a compound of Formula F14, or a salt thereof; and reacting the compound of Formula F14 with a base (Step N) to afford the compound of Formula F15. The compound of Formula F15 can be purified by trituration or recrystallization using solvents such as water, ethanol, MTBE or a combination thereof.

In some embodiments, $R^2$ is Br, $R^3$ is F, and n is 1.
In some embodiments, $R^2$ is Br, $R^3$ is F, and n is 2.
In some embodiments, $R^2$ is Cl, $R^3$ is F, and n is 1.
In some embodiments, $R^2$ is Cl, $R^3$ is F, and n is 2.
In some embodiments, $R^2$ is $CF_3$, $R^3$ is F, and n is 1.
In some embodiments, $R^2$ is $CF_3$, $R^3$ is F, and n is 2.
In some embodiments, $R^2$ is $CF_3$, $R^3$ is H, and n is 1.
In some embodiments, $R^2$ is $CF_3$, $R^3$ is H, and n is 2.
In some embodiments, $R^2$ is CN, $R^3$ is F, and n is 1.

Amino protecting groups are regularly used in organic synthesis to prevent unwanted reactions of an amino group while performing a desired transformation. Amino protecting groups allow easy covalent attachment to a nitrogen atom as well as selective cleavage from the nitrogen atom. Various amino protecting groups, classified broadly as alkoxycarbonyl (such as ethoxycarbonyl, tert-butoxycarbonyl (Boc), benzyloxycarbonyl (Cbz), 9-fluorenylmethyloxycarbonyl (Fmoc), and the like), acyl (such as acetyl (Ac), benzoyl (Bz), and the like), sulfonyl (such as methanesulfonyl, trifluoromethanesulfonyl, and the like), arylalkyl (such as benzyl, diphenylmethyl, triphenylmethyl(trityl), and the like), alkenylalkyl (such as allyl, prenyl, and the like), diarylmethyleneyl (such as $(C_6H_5)_2C=N$, and the like), and silyl (such as tert-butyldimethylsilyl, triisopropylsilyl, and the like), are known to one skilled in the art. The chemistry of amino protecting groups can be found in Wuts and Greene, *Greene's Protective Groups in Organic Synthesis*, 4$^{th}$ Ed., pp 696-926, John Wiley & Sons: New York, 2006. In some embodiments, $Pg^1$ can be alkoxycarbonyl (such as tert-butoxycarbonyl).

The amino protecting groups described above can be conveniently removed using many available amino deprotecting agents that are specific to the various groups mentioned above without affecting other desired portions of the compound. The tert-butoxycarbonyl group can be removed (e.g., hydrolyzed) from the nitrogen atom, for example, by treatment with an acid (such as trifluoroacetic acid, toluenesulfonic acid, hydrochloric acid, and the like); a combination of reagents (e.g., mixture of acetyl chloride and methanol) known to generate an acid; or a Lewis acid (e.g., $BF_3.Et_2O$). The benzyloxycarbonyl group can be removed (e.g., hydrogenolyzed) from the nitrogen atom, for example, by treatment with hydrogen and a catalyst (such as palladium on carbon). In some embodiments, the amino deprotecting agent can be trifluoroacetic acid. In some embodiments, the amino deprotecting agent contains trifluoroacetic acid and >0.5% by volume of water, e.g., >1.0% by volume of water, >1.5% by volume of water, >2.0% by volume of water, from about 2% to about 10% by volume of water, from about 10% to about 20% by volume of water, or from about 20% to about 50% by volume of water. In some embodiments, the amino deprotecting agent can be a mixture of trifluoroacetic acid and water in a volumetric ratio of about 98:2. In some embodiments, the amino deprotecting agent can be hydrochloric acid, optionally in a solvent (such as water, THF, or dioxane). In such embodiments, the hydrochloric acid can be present in a concentration of about 4 N, e.g., about 1 N, about 2 N, about 3 N, about 5 N, about 6 N, about 7 N, about 8 N, about 9 N, or about 10 N. In some embodiments, the deprotection can be performed in an alcohol (such as isopropanol). In some embodiments, the Step M (Scheme 1) can be performed at a temperature from about −10° C. to about 60° C., e.g., from about −10° C. to about 0° C., from about 0° C. to about 25° C., from about 25° C. to about 45° C., or from about 45° C. to about 60° C.

A base can be used for the conversion (e.g., hydrolysis) of the oxadiazolone ring in F14 to reveal the amidoxime in F15, optionally in a solvent (Step N, Scheme 1). The protection of the amidoxime as the oxadiazolone can be useful to prevent adverse reactions of the hydroxyl group or that of the amidoxime as a whole. The base can be either an organic base such as an acyclic amine (e.g., triethylamine, diisopropylethylamine (DIPEA), etc.) or a cyclic amine (e.g., pyrrolidine, piperidine, etc.); or an inorganic base such as alkali (e.g., NaOH, LiOH, KOH, $Mg(OH)_2$, etc.). The base can be made available in the form of a resin (such as Amberlite® and the like). In some further embodiments, the base can be provided in the form of a solution in water such as about 2N solution (e.g., about 0.5N solution, about 1N solution, about 1.5N solution, about 2.5N solution, from about 3N to about 5N solution, from about 5N to about 10N solution). In some embodiments, the base is an alkali metal hydroxide (such as, sodium hydroxide). In some embodiments, the base can be 2N NaOH solution in water. In some embodiments, the solvent can be methanol or tetrahydrofuran (THF). In some embodiments, the Step N (Scheme 1) can be performed at a temperature from about −10° C. to about 60° C., e.g., from about −10° C. to about 0° C., from about 0° C. to about 25° C., from about 25° C. to about 45° C., or from about 45° C. to about 60° C.

In Step L (Scheme 1), the compound of Formula F13 can be obtained by treating a compound of Formula F12, or a salt thereof, with $Pg^1$-NH-sulfonyl chloride, optionally in a solvent, followed by treatment of the resulting mixture with an organic base to afford the compound of Formula F13. This Step L (Scheme 1) transforms a primary amine F12 to a sulfonyl urea F13 using a protected amino-sulfonyl chloride ($Pg^1$-NH—SO$_2$Cl). The protected amino-sulfonyl chloride can be prepared and immediately used in the reaction with F12. The protecting group could be selected from any of the protecting groups known in the art for protecting amines or sulfonamides (supra). In some embodiments, $Pg^1$ can be an alkoxycarbonyl group (such as tert-butoxycarbonyl). In such embodiments, the alkoxycarbonyl NH-sulfonyl chloride can be obtained by the reaction of an alcohol (such as, ethanol, tert-butyl alcohol and the like) with chlorosulfonyl isocyanate (ClS(O)$_2$NCO). Appropriate solvents for this reaction include, but are not limited to, halogenated solvents such as dichloromethane and the like. The organic base can be any base that serves to neutralize the HCl generated during the reaction of the primary amine such as F12 and the protected amino-sulfonyl chloride. The organic base can include acyclic tertiary amines such as tri($C_{1-6}$)alkylamine (e.g., triethylamine, diisopropylethylamine (DIPEA) and the like), cyclic tertiary amines (e.g., N-methyl piperidine, 1,4-diazabicyclo[2.2.2]octane (DABCO) and the like). In some embodiments, the organic base can be triethylamine. In some embodiments, this step can be performed at a temperature from about −10° C. to about 60° C., e.g., from about −10° C. to about 0° C., from about 0° C. to about 25° C., from about 25° C. to about 45° C., or from about 45° C. to about 60° C.

Organic compounds can be reduced to a lower oxidizing state by using reducing agents. Reduction usually involves addition of hydrogen atoms or removal of oxygen atoms from a group. Organic azides such as F11 can be reduced to amines such as F12 (Step K, Scheme 1) by the addition of hydrogen, either in the form of elemental hydrogen or using a hydride reagent (such as NaBH$_4$, LiAlH$_4$ and the like); using triphenylphosphine; or using a combination of sodium iodide, chlorotrimethylsilane, and methanol. In some embodiments, the compound of Formula F12 can be obtained by reducing a compound of Formula F11, or a salt thereof. In some embodiments, the reducing can be carried out in the presence of sodium iodide, chlorotrimethylsilane, and methanol. In some embodiments, the molar ratio of sodium iodide and chlorotrimethylsilane can be about 1.0, e.g., about 0.9, about 0.95, about 1.0, about 1.05, or about 1.1. In some embodiments, chlorotrimethylsilane can be added to the mixture of F11, sodium iodide and methanol as a solution in methanol. In some embodiments, Step K (Scheme 1) can be performed at about room temperature, e.g., from about 10° C. to about 50° C., from about 15° C. to about 40° C., from about 20° C. to about 30° C., or from about 25° C. to about 30° C.

The amino compounds F12, in some cases, may prove challenging to obtain in substantially pure form as determined by HPLC or NMR spectroscopy and the like. While not intending to be bound by theory, it is believed that some of these amines might be difficult to purify by silica gel chromatography due to increased high affinity to silica gel or due to unwanted degradation during purification. In such embodiments, referring now to Scheme 2, the compound of Formula F12 can be purified by reacting the compound of Formula F12 with an amino protecting agent to afford a compound of Formula F12', or a salt thereof, wherein $Pg^2N$ is a protected amine. This protection (Step K') can be followed by purifying the compound of Formula F12' to provide a purified compound of Formula F12' and reacting the purified compound of Formula F12' with an amino deprotecting agent (Step K") to provide a purified compound of Formula F12. Amino protecting agents and amino deprotecting agents are known to one skilled in the art, such as those in Wuts and Greene (ibid). In some embodiments, the amino protecting agent is di-t-butyl dicarbonate ($Boc_2O$). In such embodiments, $Pg^2N$ is tert-butoxy carbonyl-NH. In such embodiments, the amino deprotecting agent is a reagent capable of removing the Boc protecting group (supra). In such embodiments, the amino deprotecting agent is an acid (e.g., hydrochloric acid, trifluoroacetic acid and the like), optionally in a solvent (such as water, THF, or dioxane). In some embodiments, the hydrochloric acid can be present in a concentration of about 4N, e.g., about 1N, about 2N, about 3N, about 5N, about 6N, about 7N, about 8N, about 9N, or about 10N. In some embodiments, the deprotection can be performed in an alcohol (such as isopropanol). In some embodiments, step K' or K" can be performed at a temperature from about −10° C. to about 60° C., e.g., from about −10° C. to about 0° C., from about 0° C. to about 25° C., from about 25° C. to about 45° C., or from about 45° C. to about 60° C. Appropriate purification methods are known to one skilled in the art and can include chromatography, crystallization, sublimation and the like. In some embodiments, purification can be performed by chromatography on silica gel. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

the compound of Formula F11 (Step J). In some embodiments, $L^1$ is alkylsulfonyl. Azide reagents include any reagent capable of producing a nucleophilic azide ion. Examples of azide reagents include alkali metal azides (such as sodium azide, potassium azide, etc.). In some optional embodiments, the azide reagent such as sodium azide can be used in combination with sodium iodide. Appropriate solvents for this transformation are polar solvents including DMF, DMSO, NMP and the like. In some embodiments, Step J can be carried out in DMF. Step J can be carried out at an elevated temperature e.g., from about 40° C. to about 100° C., from about 50° C. to about 90° C., or from about 60° C. to about 80° C. In some embodiments, Step J can be carried out at about 50° C. In some embodiments, Step J can be carried out at about 85° C.

The compound of Formula F10, or a salt thereof, can be obtained in a sequence of steps shown in Scheme 3. The preparation of the intermediate, 4-amino-N'-hydroxy-1,2,5-oxadiazole-3-carboximidamide F2, has been described in *J. Heterocycl. Chem.* (1965), 2, 253, which is incorporated herein by reference in its entirety, and its conversion to the chloro oxime F3 has been described in *Synth. Commun.* (1988), 18, 1427, which is incorporated herein by reference in its entirety. Amines (such as primary or secondary amines including amines that contain protected functionalities, e.g., ethyl amine, 2-methoxyethylamine or dimethylamine) can be coupled to the chloro oxime F3, optionally in a solvent (such as ethyl acetate), followed by addition of an organic base (such as triethylamine or DIPEA to quench the HCl generated in the reaction) to provide amidoxime compounds F4. Rearrangement of the compounds such as F4, to transpose the amino group on the ring carbon and the amino group on the oxime carbon, to provide compounds F5 can be achieved by the treatment of F4 with a base (such as KOH, NaOH, LiOH, $Mg(OH)_2$, $Al(OH)_3$ and the like), optionally in a solvent (such as water, ethanol, ethylene glycol and the like), and refluxing Scheme 2

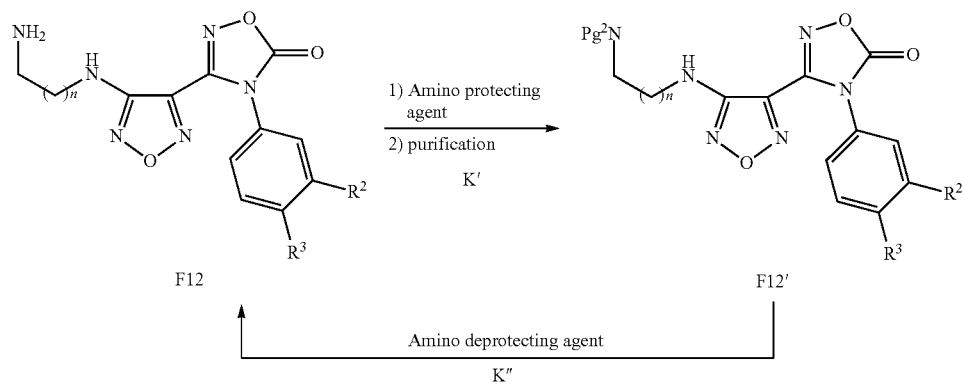

In some embodiments, the compound of Formula F11 (Scheme 1) can be obtained by treating a compound of Formula F10, or a salt thereof, wherein $L^1$ can be selected from alkylsulfonyl (such as methanesulfonyl), haloalkylsulfonyl (such as trifluoromethanesulfonyl), arylsulfonyl (such as toluenesulfonyl) and the like; with an azide reagent to afford the reaction mixture at elevated temperature e.g., about 70° C., about 80° C., about 90° C., about 100° C., about 110° C., about 120° C., about 130° C., about 140° C., about 150° C., about 160° C., about 170° C., about 180° C., about 190° C., or about 200° C. The amidoxime F5 can again be activated as a chloro oxime F6 by the addition of F5 to an aqueous acidic mixture containing hydrochloric acid, optionally including acetic acid. In this process for the conversion of F5 to F6, the acidic mixture of F5 can be heated to a temperature of about 45° C., such as about 30° C., about 40° C., about 50° C., or about 60° C. to achieve dissolution. Sodium chloride can be added to this solution and then treated with a nitrite reagent, which can optionally be provided as an aqueous solution, at a temperature below about 0° C., such as below about –10° C., below about –5° C., below about 5° C., or below about 10° C. The nitrite reagent is one capable of providing a nitrite anion. Nitrite reagents include alkali metal nitrite (e.g., sodium nitrite, potassium nitrite and the like) and organo nitrites (e.g., tetraethylammonium nitrite) which includes an organic cation. In some embodiments, ethyl acetate, THF or dioxane can be used as a co-solvent. The chloro oxime F6 can be coupled with aromatic amines such as anilines, optionally in a polar solvent (such as methanol, water, ethanol and the like) at elevated temperatures such as about 50° C., about 60° C., about 70° C., about 80° C., about 90° C., about 100° C., about 110° C., or about 120° C., optionally in the presence of an inorganic base (such as $KHCO_3$, $NaHCO_3$) to provide arylamidoxime F7. In some embodiments, the inorganic base can be provided in the form of an aqueous solution. In some embodiments, the inorganic base can be added to the reaction mixture at an elevated temperature. The amidoxime functionality of F7 can then be protected as an oxadiazolone using 1,1'-carbonyl diimidazole (CDI) in a solvent (such as ethyl acetate, dioxane, THF and the like) at elevated temperatures such as about 50° C., about 60° C., about 70° C., about 80° C., about 90° C., or about 100° C. The methoxy group of F8 can then be converted to a hydroxyl group in F9 using a methoxy deprotecting agent known to one skilled in the art, such as those in Wuts and Greene, *Greene's Protective Groups in Organic Synthesis*, 4th Ed., pp 24-30, John Wiley & Sons: New York, 2006. For example, by addition of boron tribromide to a cold (such as from about –78° C. to about 25° C., e.g., from about –78° C. to about 10° C., from about –78° C. to about 0° C., from about –78° C. to about –10° C., from about 0° C. to about 25° C., or from about 0° C. to about 10° C.) solution of F8, optionally in a solvent such as a halogenated solvent (e.g., DCM, chloroform and the like) or ethyl acetate. The primary hydroxyl group in F9 can subsequently be activated as a leaving group $L^1O$— (see F10) by sequential treatment with $L^1Cl$, optionally in a solvent (such as ethyl acetate or DCM), and an organic base to mop up the generated HCl (such as triethylamine or DIPEA). $L^1$, for example, can be selected from alkylsulfonyl (e.g., methanesulfonyl), haloalkylsulfonyl (e.g., trifluoromethanesulfonyl), arylsulfonyl (e.g., toluenesulfonyl) and the like. The compound F10 can then be treated with any nucleophile for displacement (such as by $S_N2$ mechanism) of the leaving group $L^1O$.

Scheme 3

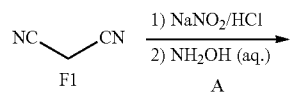

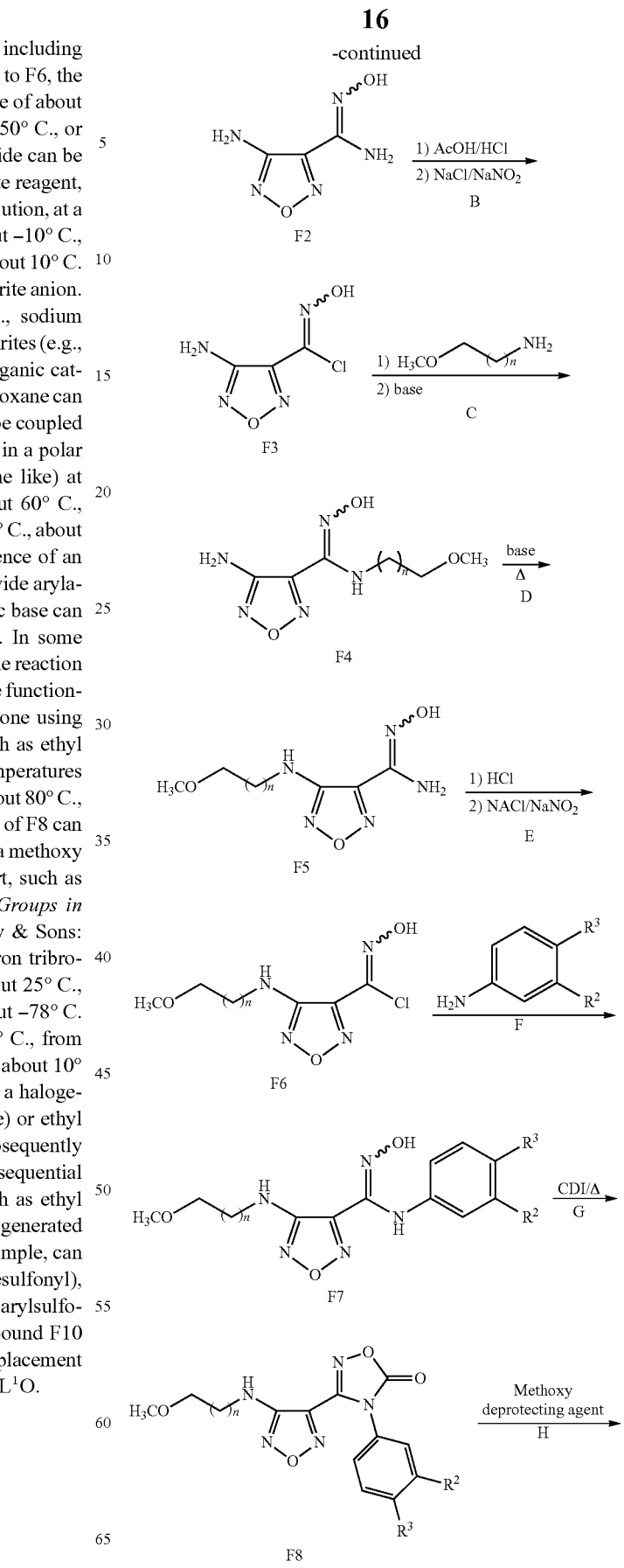

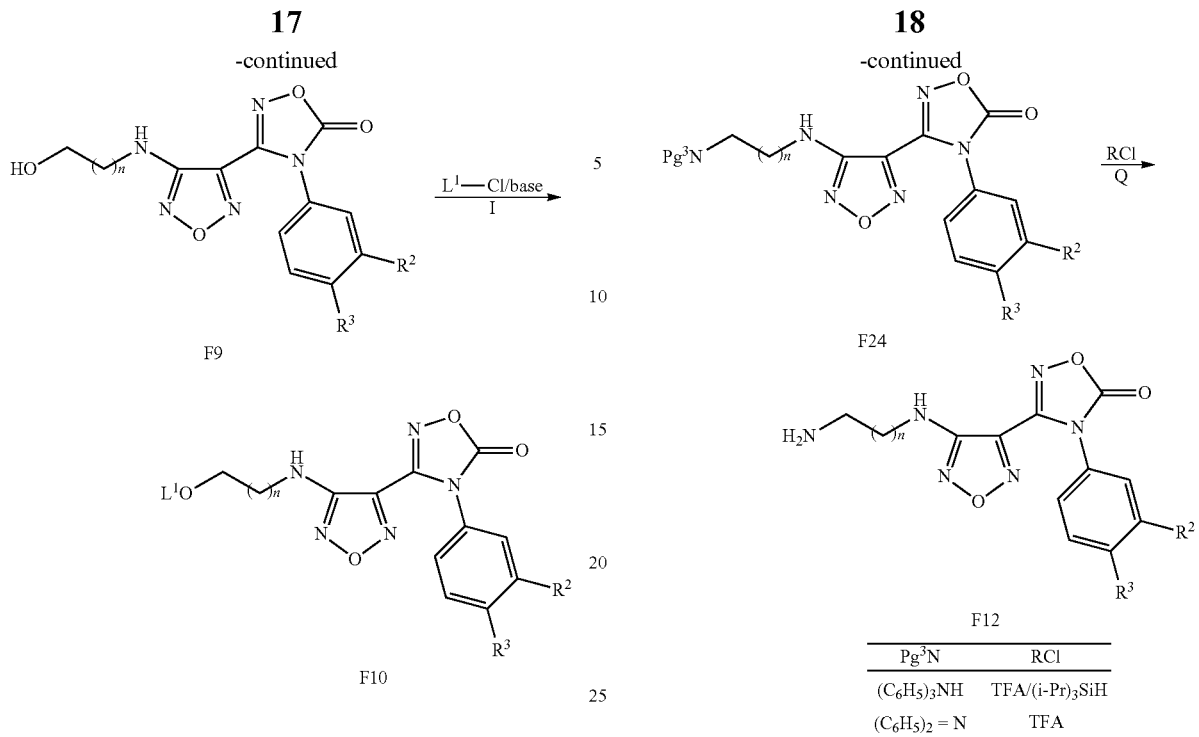

Alternately, the compound of Formula F12 can be obtained through a sequence of steps depicted in Scheme 4.

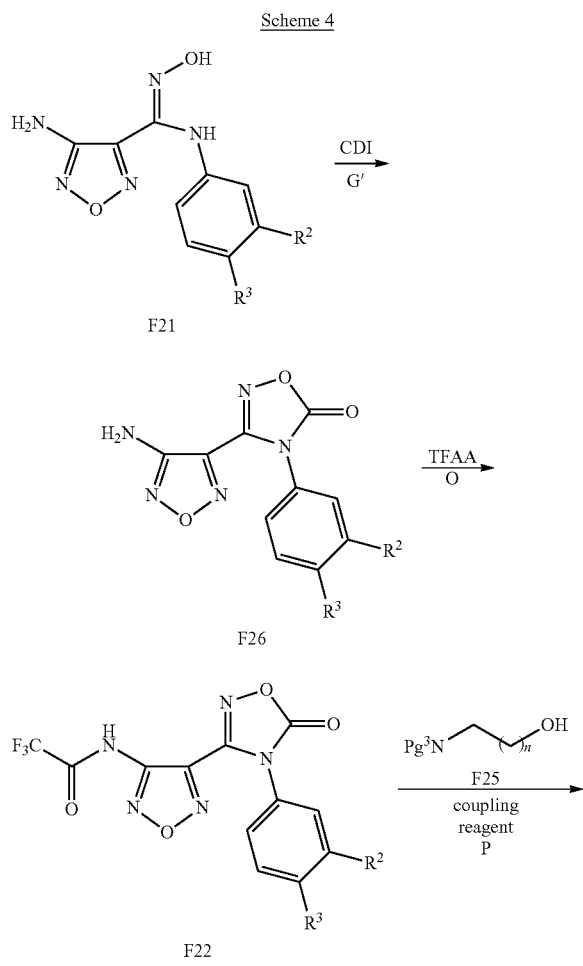

Referring now to Scheme 4, in some embodiments, the compound of Formula F12 can be obtained by reacting a compound of Formula F24, or a salt thereof, wherein $Pg^3N$ is a protected amine (e.g., $(C_6H_5)_3C$—NH, $(C_6H_5)_2C$=N and the like); with an amino deprotecting agent to afford the compound of Formula F12. Treatment of a compound F24 to replace $Pg^3N$ with $NH_2$ (Step Q) can be accomplished by methods for the deprotection of particular amine protecting groups known to one skilled in the art, such as those in Wuts and Greene, *Greene's Protective Groups in Organic Synthesis*, 4$^{th}$ Ed., pp 696-926, John Wiley & Sons: New York, 2006. In some embodiments, when the $Pg^3N$ is $(C_6H_5)_2C$=NH, the deprotecting agent can be: an acid such as an organic acid (e.g., trifluoroacetic acid, methanesulfonic acid and the like) or an inorganic acid (e.g., hydrochloric acid); hydrogen and palladium; or acidic hydroxylamine ($NH_2OH$). In some embodiments, when the $Pg^3N$ is $(C_6H_5)_3C$—NH, the deprotecting agent can include an organic acid (such as trifluoroacetic acid methanesulfonic acid and the like) and optionally an organosilane; hydrogen and palladium; or sodium in liquid ammonia. Organosilanes are compounds that contain at least one Si—H bond and the rest of the groups attached to silicon are alkyl, aryl or a combination thereof. Examples of organosilanes include trialkylsilane (e.g., tri(isopropyl)silane)), triarylsilane (e.g., triphenylsilane) or diphenylmethylsilane. The step Q can be performed at a temperature from about −10° C. to about 60° C., e.g., from about −10° C. to about 0° C., from about 0° C. to about 25° C., from about 25° C. to about 45° C., or from about 45° C. to about 60° C.

Compounds F24 which are protected secondary amines can be prepared by the Mitsunobu reaction of alcohols F25 with protected primary amines F22 in the presence of a coupling reagent (Step P). The coupling reagent can be a combination of a tertiary phosphine such as triarylphosphine (e.g., triphenylphosphine) or trialkylphosphine (e.g., tributylphosphine) and a dialkyl azodicarboxylate. Dialkyl azodicarboxylates possess a general structure: ROOC—N=N—COOR, where R can be an alkyl group (e.g., diisopropyl azodicarboxylate, diethyl azodicarboxylate, or di-p-chlorobenzyl azodicarboxylate). While not intending to be bound by theory, it is believed that amine protection with trifluoroacetyl moiety (such as in F22) prevents side reactions and improves the yield of the secondary amine F24. The hydroxyl group of alcohols such as F25 can be activated in the presence of the coupling reagent. The amine nucleophile can displace the activated hydroxyl group to form the secondary amine. The Mitsunobu reaction can be performed in a solvent such as an ether e.g., THF, dioxane, dialkyl ether and the like; halogenated solvents e.g., dichloromethane, chloroform and the like; non-polar solvents e.g., benzene, toluene and the like; polar-aprotic solvents such as DMF, HMPA and the like. In some embodiments, the compound of Formula F24 can be obtained by treating a compound of Formula F22, or a salt thereof, with a compound of Formula F25, or a salt thereof, and a coupling reagent to provide the compound of Formula F24. In some embodiments, this step can be performed at a temperature from about −10° C. to about 60° C., e.g., from about −10° C. to about 0° C., from about 0° C. to about 25° C., from about 25° C. to about 45° C., or from about 45° C. to about 60° C.

Compounds F22 can be made by a two step process (Steps G' and O) from compounds F21. Compounds F21 can be treated with 1,1'-carbonyl diimidazole (CDI), optionally in a solvent (such as ethyl acetate or THF), at an elevated temperature such as about 50° C., e.g., about 60° C., about 65° C., about 70° C., about 80° C., or about 90° C., to convert the amidoxime in compounds F21 to oxadiazolone present in compounds F26. These compounds F26 in turn can be treated with trifluoroacetic anhydride, optionally in a solvent (such as DCM, THF, dioxane, or ethyl acetate) in the presence of an organic base (such as pyridine, triethylamine, DIPEA and the like) to provide compounds F22. In some embodiments, the compound of Formula F22 can be obtained by treating a compound of Formula F21, or a salt thereof, with carbonyl diimidazole (CDI) to afford a compound of Formula F26, or a salt thereof, and treating the compound of Formula F26 with trifluoroacetic anhydride to afford the compound of Formula F22.

Scheme 5

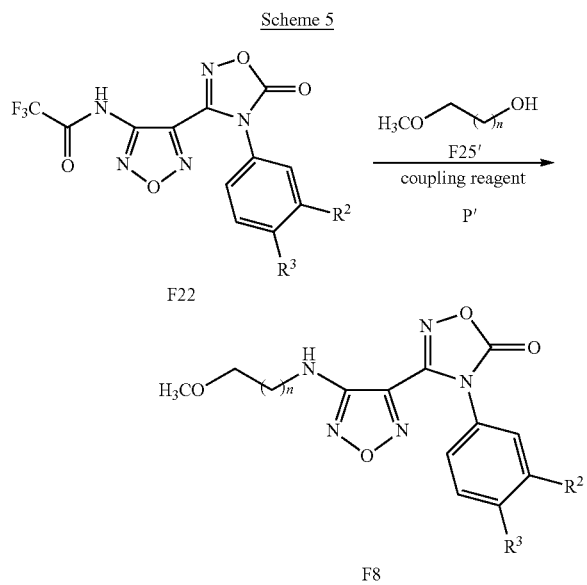

Referring now to Scheme 5 (Step P') and based on the above description of Mitsunobu reaction, another aspect of the invention provides a process for preparing a compound of Formula F8, or a salt thereof, wherein, $R^2$, $R^3$, and n are defined herein; including reacting a compound of Formula F22, or a salt thereof, and a compound of Formula F25', or a salt thereof, with a coupling reagent, optionally in a solvent (such as THF, dialkyl ether, or dichloromethane), to provide the compound of Formula F8. In some embodiments, this step can be performed at a temperature from about −10° C. to about 60° C., e.g., from about −10° C. to about 0° C., from about 0° C. to about 25° C., from about 25° C. to about 45° C., or from about 45° C. to about 60° C.

Scheme 6

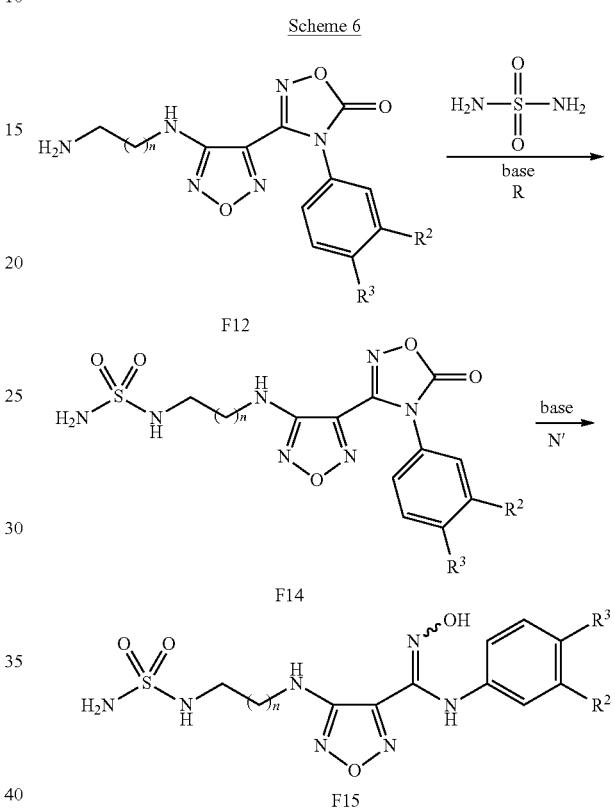

Scheme 6 delineates an alternative route for the introduction of the sulfonamide group to the amino compound F12. Treatment of F12 with sulfamide in the presence of a base (Step R) such as an organic base which can be a heterocyclic base (e.g., pyridine), or a trialkylamine (e.g., triethylamine, DIPEA and the like), each of which can optionally be used as a solvent for this transformation, can provide sulfonyl ureas such as F14. This reaction can be carried out at elevated temperatures such as about 130° C., e.g., about 100° C., about 110° C., about 120° C., about 130° C., or about 140° C. Such heating can be favorably applied using microwave irradiation. Microwave irradiation can be performed in a commercial microwave oven (e.g., the Initiator™, available from Biotage) operating in a single mode fashion. Compounds F14 containing the oxadiazolone ring can be deprotected (e.g., hydrolyzed) to the desired amidoximes F15 in the presence of a base (Step N'). The base can be either an organic base such as an acyclic amine (e.g., triethylamine, diisopropylethylamine (DIPEA), etc.) or a cyclic amine (e.g., pyrrolidine, piperidine, etc.); or an inorganic base such as alkali (e.g., NaOH, LiOH, KOH, Mg(OH)$_2$, etc.). The base can be made available in the form of a resin (such as Amberlite® and the like). In some further embodiments, the base can be provided in the form of a solution in water such as about 2N solution (e.g., about 0.5N solution, about 1N solution, about 1.5N solution, about 2.5N solution, from about 3N to about 5N solution, from about 5N to about 10N solution). In some embodiments, the base can be an alkali metal hydroxide (such as, sodium hydroxide). In some embodiments, the base can be a 2N NaOH solution in water. In some embodiments, the solvent can be methanol or tetrahydrofuran (THF). In some embodiments, the deprotection can be performed at a temperature from about −10° C. to about 60° C., e.g., from about −10° C. to about 0° C., from about 0° C. to about 25° C., from about 25° C. to about 45° C., or from about 45° C. to about 60° C. Hence, this aspect of the invention provides a process for preparing a compound of Formula F15, or a salt thereof, wherein $R^2$, $R^3$, and n, are as defined herein; including reacting a compound of Formula F12, or a salt thereof, with sulfamide and an organic base to afford a compound of Formula F14, or a salt thereof, and reacting the compound of Formula F14, or a salt thereof, with a base to afford the compound of Formula F15.

The present invention further provides a compound of Formula F9, F12, and F14, or a salt thereof, wherein $R^2$ is Cl, Br, $CF_3$, $CH_3$, or CN; $R^3$ is H or F; and n is 1 or 2.

In some embodiments, $R^2$ is Br, $R^3$ is F, and n is 1.
In some embodiments, $R^2$ is Br, $R^3$ is F, and n is 2.
In some embodiments, $R^2$ is Cl, $R^3$ is F, and n is 1.
In some embodiments, $R^2$ is Cl, $R^3$ is F, and n is 2.
In some embodiments, $R^2$ is $CF_3$, $R^3$ is F, and n is 1.
In some embodiments, $R^2$ is $CF_3$, $R^3$ is F, and n is 2.
In some embodiments, $R^2$ is $CF_3$, $R^3$ is H, and n is 1.
In some embodiments, $R^2$ is $CF_3$, $R^3$ is H, and n is 2.
In some embodiments, $R^2$ is $CH_3$, $R^3$ is F, and n is 1.
In some embodiments, $R^2$ is CN, $R^3$ is F, and n is 1.

with methanesulfonyl chloride (Step S), optionally in a solvent such as ethyl acetate, halogenated solvents (e.g., dichloromethane, chloroform and the like) or ethereal solvents (THF, diethyl ether, dioxane and the like), in the presence of an organic base (to mop up the generated HCl) such as tri($C_{1-6}$)alkylamine (e.g., triethylamine, DIPEA and the like), or pyridine to afford sulfonamides F20. The methanesulfonyl group can be replaced with other alkylsulfonyl (e.g., ethylsulfonyl), haloalkylsulfonyl (e.g., trifluoromethanesulfonyl), arylsulfonyl (e.g., toluenesulfonyl) and the like, without altering the procedures. In some embodiments, this step can be performed at a temperature from about −10° C. to about 60° C., e.g., from about −10° C. to about 0° C., from about 0° C. to about 25° C., from about 25° C. to about 45° C., or from about 45° C. to about 60° C. The sulfonamide compounds F20 containing the oxadiazolone ring can be deprotected (e.g., hydrolyzed) to the desired amidoximes F19 in the presence of a base (Step N″). The base can be either an organic base such as an acyclic amine (e.g., triethylamine, diisopropylethylamine (DIPEA), etc.) or a cyclic amine (e.g., pyrrolidine, piperidine, etc.); or an inorganic base such as alkali metal hydroxide or alkaline earth metal hydroxide (e.g., NaOH, LiOH, KOH, $Mg(OH)_2$, etc.). The base can be made available in the form of a resin (such as Amberlite® and the like). In some further embodiments, the base can be provided in the form of a solution in water such as about 2N solution (e.g., about 0.5N solution, about 1N solution, about 1.5N solution, about 2.5N solution, from about 3N to about 5N solution, from about 5N to about 10N solution). In some embodiments, the base is an alkali metal hydroxide (e.g., sodium hydroxide). In some embodiments, the base can be 2N NaOH solution in water. In some embodiments, the solvent can be methanol or tetrahydrofuran (THF). In some embodiments, the deprotection can be performed at a temperature from about −10° C. to about 60° C., e.g., from about −10° C. to about 0° C., from about 0° C. to about 25° C., from about 25° C. to about 45° C., or from about 45° C. to about 60° C. Accordingly, another aspect of the invention provides a process for preparing a compound of Formula F19, or a salt thereof, wherein $R^2$, $R^3$, and n, are as defined herein; including reacting a compound of Formula F12, or a salt thereof, with methanesulfonyl chloride in the presence of an organic base to afford a compound of Formula F20, or a salt thereof, and reacting the compound of Formula F20 with a base to afford the compound of Formula F19. In some embodiments, the base can be an alkali metal hydroxide such as sodium hydroxide (e.g., 2N NaOH).

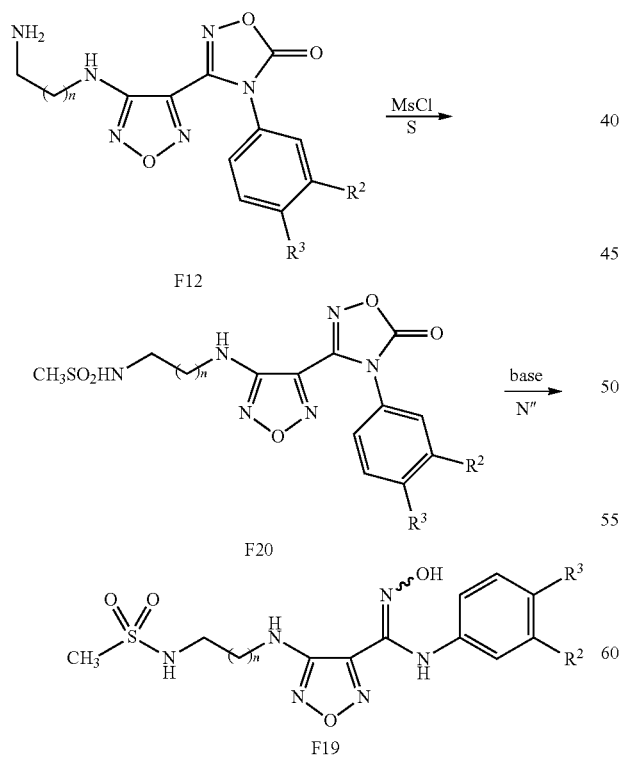

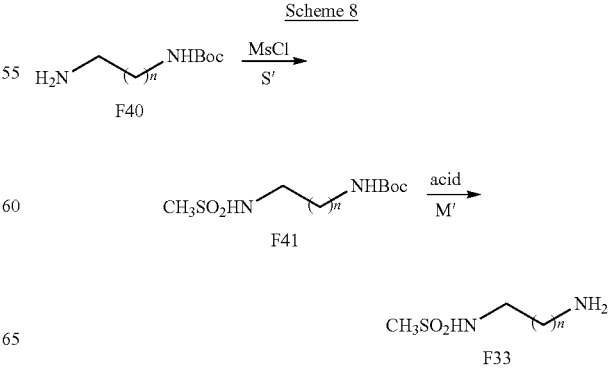

Referring now to Scheme 7, compounds F19 can be obtained from primary amino compounds F12 by treatment

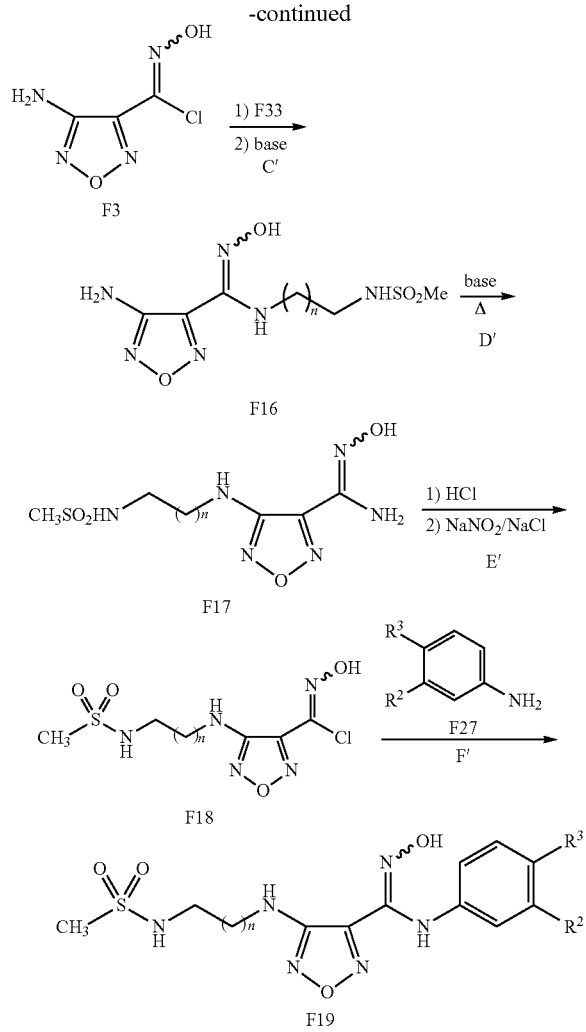

dimethylamine or F33) can be coupled to the chloro oxime F3, optionally in a solvent (such as ethyl acetate or ethanol), followed by addition of an organic base (such as triethylamine or DIPEA to quench the HCl generated in the reaction) to provide amidoxime compounds F16 (Step C'). In some embodiments, this step can be performed at a temperature from about −10° C. to about 60° C., e.g., from about −10° C. to about 0° C., from about 0° C. to about 25° C., from about 25° C. to about 45° C., or from about 45° C. to about 60° C. Rearrangement of the compounds such as F16 to transpose the amino group on the ring carbon and the amino group on the oxime carbon to provide compounds such as F17 (Step D') can be achieved by the treatment of F16 with a base (such as KOH, NaOH, LiOH, Mg(OH)$_2$, Al(OH)$_3$ and the like), optionally in a solvent (such as water, ethanol, ethylene glycol and the like), and refluxing the reaction mixture at elevated temperature e.g., about 70° C., about 80° C., about 90° C., about 100° C., about 110° C., about 120° C., about 130° C., about 140° C., about 150° C., about 160° C., about 170° C., about 180° C., about 190° C., or about 200° C. The amidoxime F17 can again be activated as a chloro oxime F18 by the addition of F17 to an aqueous acidic mixture containing hydrochloric acid, optionally including acetic acid (Step E'). In this process for the conversion of F17 to F18, the acidic mixture of F17 can be heated to temperature about 45° C., such as about 30° C., about 40° C., about 50° C., or about 60° C. to achieve dissolution. Sodium chloride can be added to this solution and treated with a nitrite reagent, which can optionally be provided as an aqueous solution, at a temperature below about 0° C. such as below about −10° C., below about −5° C., below about 5° C., or below about 10° C. The nitrite reagent is one capable of providing a nitrite anion. Nitrite reagents include alkali metal nitrite (e.g., sodium nitrite, potassium nitrite and the like) and organo nitrites (e.g., tetraethylammonium nitrite) which includes an organic cation. In some embodiments, ethyl acetate, THF or dioxane can be used as a co-solvent. The substitution of the chloride in F18 with aromatic amines such as anilines F27, optionally in a polar solvent (such as methanol, water, ethanol and the like), at room temperature can afford methanesulfonamides F19 (Step F'). In some embodiments, temperatures such as about 10° C., about 20° C., about 30° C., about 40° C., or about 50° C. can be employed. This reaction can be optionally carried out in the presence of an inorganic base (such as KHCO$_3$, NaHCO$_3$) which can be provided in the form of an aqueous solution.

Accordingly, in another aspect of the invention provides a process for preparing a compound of Formula F19, or a salt thereof, wherein R$^2$, R$^3$, and n, are as defined herein; including reacting a compound of Formula F17, or a salt thereof, with hydrochloric acid, optionally in a solvent (such as dioxane), followed by treatment with a nitrite reagent (such as, sodium nitrite), optionally in the form of an aqueous solution, to afford a compound of Formula F18, or a salt thereof, and reacting the compound of Formula F18 with a compound of Formula F27, or a salt thereof, to afford the compound of Formula F19.

In some embodiments, the compound of Formula F17 can be obtained by treating a compound of Formula F16, or a salt thereof, with a base (such as potassium hydroxide) in a solvent (such as ethylene glycol) at a temperature sufficient to reflux the solvent (such as 130° C.), to provide a compound of Formula F17.

The present invention further provides a compound of Formula F18, or a salt thereof, wherein n is 1 or 2. In some embodiments, n is 1. In some embodiments, n is 2.

Aryl or alkylsulfonamides (e.g., methanesulfonamides F19) can be obtained by the sequence of steps shown in Scheme 8. Mono-protected 1,n-diamines such as F40 (e.g., commercially available N-(aminoalkyl)(t-butoxy)carboxamide) can be treated with sulfonyl chlorides such as arylsulfonyl chlorides or alkylsulfonyl chlorides (e.g., methanesulfonyl chloride), optionally in a solvent such as ethyl acetate, halogenated solvents (e.g., dichloromethane, chloroform and the like) or ethereal solvents (THF, diethyl ether, dioxane and the like), in the presence of an organic base (to mop up the generated HCl) such as triethylamine, pyridine, DIPEA and the like, to provide sulfonamides F41 (Step S'). The protecting group on mono-protected 1,n-diamines F40 may be selected from the various amino protecting groups and a suitable deprotection conditions can be appropriately selected (supra) to afford amine F33 (Step M'). In some embodiments, protecting group can be alkoxycarbonyl (such as tert-butoxycarbonyl, Boc). In such embodiments, the amino deprotecting agent can be an acid e.g., hydrochloric acid or trifluoroacetic acid, optionally in a solvent (such as dioxane).

The preparation of chloro oxime F3 has been described in Synth. Commun. (1988), 18, 1427, which is incorporated herein by reference in its entirety. Amines (such as primary or secondary amines including amines that contain protected functionalities, e.g., ethyl amine, 2-methoxyethylamine,

Scheme 9

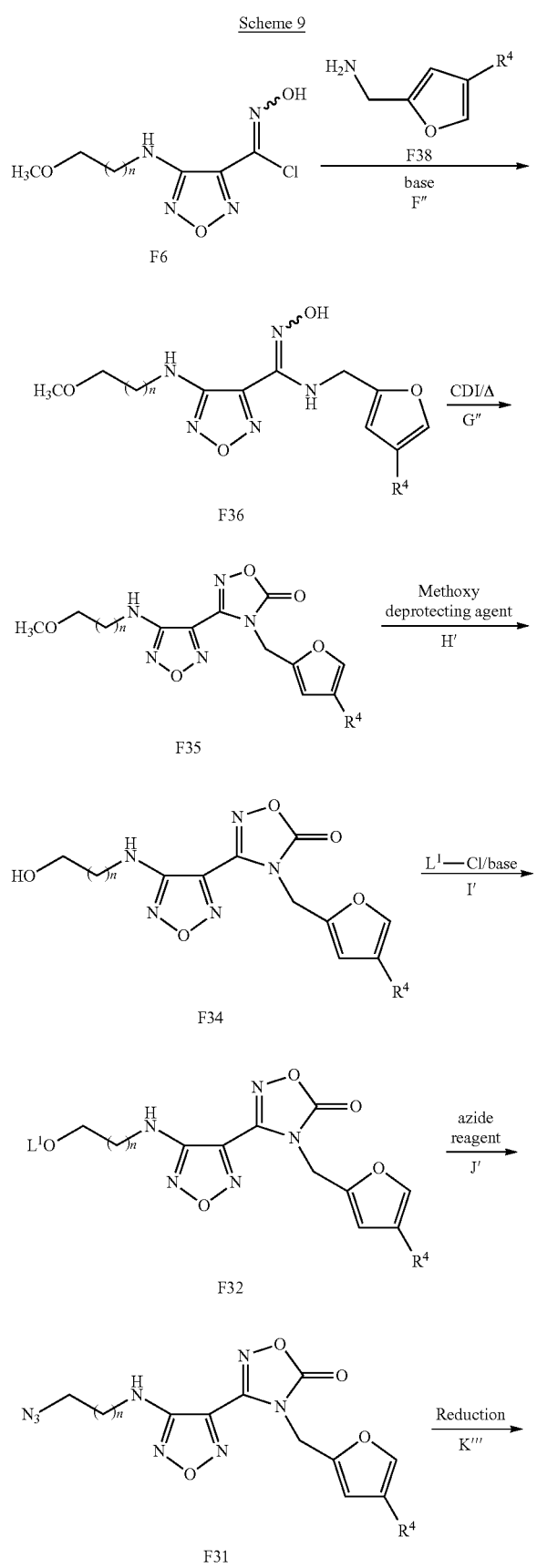

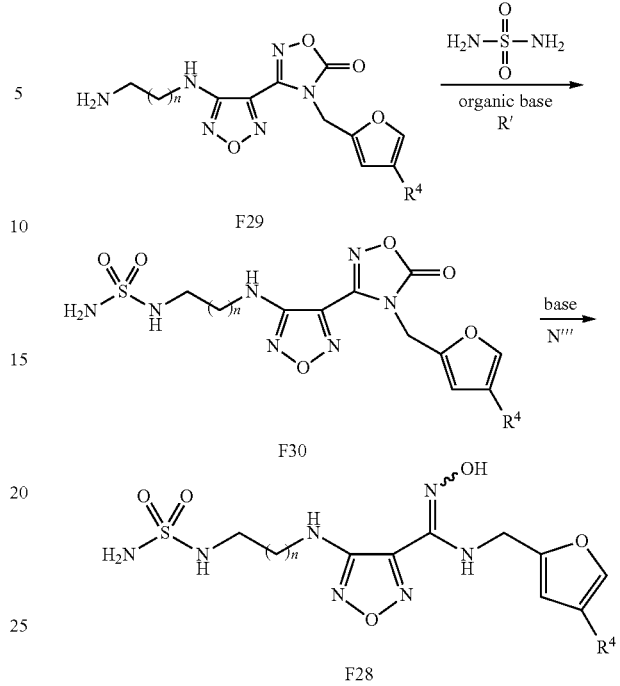

Compounds F28 can be obtained as described in Scheme 9. The chloro oxime F6 (supra, Scheme 1) can be coupled with heterocyclic amines (such as compound of Formula F38), optionally in a polar solvent (such as methanol, water, ethanol and the like), in the presence of a base such as an inorganic base or an organic base (e.g., Et$_3$N, pyridine or DIPEA) to provide arylamidoxime F36 (Step F″). In some embodiments, the conversion of F6 to F36 can be carried out at temperatures such as about 10° C., about 20° C., about 30° C., about 40° C., about 50° C., about 60° C., or about 90° C. In some embodiments, the inorganic base can be provided in the form of an aqueous solution. In some embodiments, the inorganic base can be added to the reaction mixture at an elevated temperature. The amidoxime functionality of F36 can then be protected as an oxadiazolone using 1,1′-carbonyl diimidazole (CDI) in a solvent (such as ethyl acetate, dioxane, THF and the like) at elevated temperatures such as about 50° C., about 60° C., about 70° C., about 80° C., about 90° C., or about 100° C. (Step G″). The methoxy group of F35 can then be converted to a hydroxyl group in F34 by methods known to one skilled in the art for the deprotection of methoxy group (Step H′), such as those in Wuts and Greene, *Greene's Protective Groups in Organic Synthesis,* 4$^{th}$ Ed., pp 24-30, John Wiley & Sons: New York, 2006. For example, by addition of boron tribromide to a cold (such as from about −78° C. to about 25° C., e.g., from about −78° C. to about 10° C., from about −78° C. to about 0° C., from about −78° C. to about −10° C., from about 0° C. to about 25° C., or from about 0° C. to about 10° C.) solution of F35, optionally in a solvent such as a halogenated solvent (e.g., DCM, chloroform and the like) or ethyl acetate. The primary hydroxyl group in F34 can then be subsequently activated as a leaving group L$^1$O— (see Step I′, F32) by sequential treatment with L$^1$Cl, optionally in a solvent (such as ethyl acetate or DCM), and an organic base to mop up the generated HCl (such as triethylamine or DIPEA). In compounds F32, L$^1$ can be selected from alkylsulfonyl (e.g., methanesulfonyl), haloalkylsulfonyl (e.g., trifluoromethanesulfonyl), arylsulfonyl (e.g., toluenesulfonyl) and the like. The compound F32 can then be treated with any nucleophile for $S_N2$ displacement of the leaving group $L^1O$. In some embodiments, this step can be performed at a temperature from about −10° C. to about 60° C., e.g., from about −10° C. to about 0° C., from about 0° C. to about 25° C., from about 25° C. to about 45° C., or from about 45° C. to about 60° C.

When the nucleophile is an azide ion, F32 provides F31 (Step J'). Azide reagents include any reagent capable of producing a nucleophilic azide ion. Examples of azide reagents include alkali metal azides (such as sodium azide, potassium azide). In some optional embodiments, the azide reagent such as sodium azide can be used in combination with sodium iodide. Appropriate solvents for this transformation are polar solvents including DMF, DMSO, NMP and the like. In some embodiments, this step can be carried out in DMF. In some embodiments, this step can be carried out at an elevated temperature e.g., from about 40° C. to about 100° C., from about 50° C. to about 90° C., or from about 60° C. to about 80° C. In some embodiments, this step can be carried out at 50° C. In some embodiments, this step can be carried out at 85° C. Organic azides such as F31 can be reduced to organic amines such as F29 by the addition of hydrogen, either in the form of elemental hydrogen; using a hydride reagent (such as $NaBH_4$, $LiAlH_4$ and the like); using triphenylphosphine; or using a combination of sodium iodide, chlorotrimethylsilane, and methanol (Step K'''). In some embodiments, the reducing can be carried out in the presence of sodium iodide, chlorotrimethylsilane, and methanol. In some embodiments, the reduction can be performed at about room temperature e.g., from about 10° C. to about 50° C., from about 15° C. to about 40° C., from about 20° C. to about 30° C., or from about 25° C. to about 30° C. In some embodiments, the molar ratio of sodium iodide and chlorotrimethylsilane can be about 1.0 e.g., about 0.9, about 0.95, about 1.0, about 1.05, or about 1.1. In some embodiments, chlorotrimethylsilane can be added to the mixture of F31, sodium iodide and methanol as a solution in methanol.

Treatment of F29 with sulfamide in the presence of a base such as an organic base which can be a heterocyclic base (e.g., pyridine), or a trialkylamine (e.g., triethylamine, DIPEA and the like), each of which can optionally be used as a solvent for this transformation to provide the sulfonyl ureas such as F30 (Step R'). This reaction can be carried out at elevated temperatures such as about 130° C., e.g., about 100° C., about 110° C., about 120° C., about 130° C., or about 140° C. Such heating can be favorably applied using microwave irradiation. Microwave irradiation can be performed in a commercial microwave oven (e.g., the Initiator™, available from Biotage) operating in a single mode fashion. Compounds F30 containing the oxadiazolone ring can be deprotected (e.g., hydrolyzed) to the desired amidoximes F28 in the presence of a base (Step N'''). The base can be either an organic base such as acyclic amines (e.g., triethylamine, diisopropylethylamine (DIPEA), etc.) or cyclic amines (e.g., pyrrolidine, piperidine, etc.); or an inorganic base such as alkali (e.g., NaOH, LiOH, KOH, $Mg(OH)_2$, etc.). The base can be made available in the form of a resin (such as Amberlite® and the like). In some further embodiments, the base can be provided in the form of a solution in water (an aqueous base) such as about 2N solution (e.g., about 0.5N solution, about 1N solution, about 1.5N solution, about 2.5N solution, from about 3N to about 5N solution, from about 5N to about 10N solution). In some embodiments, the base can be an alkali metal hydroxide (e.g., sodium hydroxide). In some embodiments, the base can be a 2N NaOH solution in water. In some embodiments, the solvent can be methanol or tetrahydrofuran (THF). In some embodiments, the deprotection can be performed at a temperature from about −10° C. to about 60° C., e.g., from about −10° C. to about 0° C., from about 0° C. to about 25° C., from about 25° C. to about 45° C., or from about 45° C. to about 60° C.

Accordingly, another aspect of the invention provides a process for preparing a compound of Formula F28, or a salt thereof, wherein $R^4$ is F, Cl, Br, or I; and n is 1 or 2; including reacting a compound of Formula F29, or a salt thereof, with sulfamide and an organic base to afford a compound of Formula F30, or a salt thereof, and reacting the compound of Formula F30 with a base to afford the compound of Formula F28.

In some embodiments, $R^4$ is Cl and n is 1.

In some embodiments, $R^4$ is Br and n is 1.

In some embodiments, reacting a compound of Formula F29 further includes heating the reaction (such as using microwave irradiation).

In another aspect, the invention provides a process of obtaining the compound of Formula F29 by reducing a compound of Formula F31, or a salt thereof. In some embodiments, the reducing can be carried out with a combination of sodium iodide, chlorotrimethylsilane, and methanol.

In another aspect of the invention, the compound of Formula F31 can be obtained by treating a compound of Formula F32, or a salt thereof, wherein $L^1$ is selected from alkylsulfonyl, haloalkylsulfonyl, and arylsulfonyl; with an azide reagent to afford the compound of Formula F31.

As used herein, the term "alkyl," when used alone or together with additional moiety terms, refers to a straight-chained or branched, saturated hydrocarbon group having from 1 to 6 carbon atoms, 1 to 4 carbon atoms, or 1 to 3 carbon atoms. Example alkyl groups include methyl, ethyl, n-propyl, isopropyl, n-butyl, isobutyl, sec-butyl, and the like.

As used herein, "alkenyl" refers to an alkyl group having one or more double carbon-carbon bonds. Example alkenyl groups include ethenyl(vinyl), propenyl, and the like.

As used herein, the term "aryl" refers to an aromatic hydrocarbon group which can be mono- or polycyclic having from 6 to 14 carbon atoms. Example aryl groups include phenyl, naphthyl, anthracenyl, phenanthrenyl, indanyl, indenyl, and the like.

As used herein, the term "haloalkyl," when used alone or together with an additional moiety, refers to an alkyl group substituted by one or more halogen atoms independently selected from F, Cl, Br, and I. Example haloalkyl groups include $CF_3$, $CHF_2$, $CH_2CF_3$, and the like.

As used herein, the term "alkoxy" refers to an —O-alkyl group. Example alkoxy groups include methoxy, ethoxy, propoxy (e.g., n-propoxy and isopropoxy), t-butoxy, and the like.

As used herein, "alkylamine" refers to an amino ($NH_2$) group substituted by an alkyl group. Example alkylamine groups include methylamine, hexylamine, and the like.

As used herein, "trialkylamine" refers to a nitrogen atom substituted by three alkyl group. Example trialkylamine groups include trimethylamine, triethylamine, and the like.

As used herein, the term "alkoxycarbonyl" refers to CO substituted by an alkoxy group: —C(O)—O-alkyl. Example alkoxycarbonyl groups include ethoxycarbonyl, tert-butoxycarbonyl (Boc), benzyloxycarbonyl (Cbz), 9-fluorenylmethyloxycarbonyl (Fmoc), and the like.

As used herein, the term "alkylsulfonyl" refers to a sulfonyl group substituted by an alkyl group: $alkylS(O)_2$—. Example alkylsulfonyl groups include, methanesulfonyl, ethanesulfonyl, and the like.

As used herein, the term "haloalkylsulfonyl" refers to a sulfonyl group substituted by a haloalkyl group. Example haloalkylsulfonyl groups include, trifluoromethanesulfonyl, 1,1,1-trifluoroethanesulfonyl, and the like.

As used herein, the term "arylsulfonyl" refers to a sulfonyl group substituted by an aryl group or a substituted aryl group, wherein the substituents on the aryl group are selected from halo, nitro, $C_{1-4}$ alkyl, and $C_{1-4}$ haloalkyl.

As used herein, the term "heterocyclic base" refers to a 4 to 14 membered, optionally substituted, heterocycle wherein at least one ring forming member is a nitrogen atom. The heterocyclic base can be aromatic or non-aromatic. Example heterocyclic bases include pyridine, pyrrolidine, piperidine, morpholine etc. Example substituents on the heterocycle include F, Cl, Br, $C_{1-4}$ alkyl, and $C_{1-4}$ haloalkyl.

Methods of Use

Compounds of the invention can inhibit activity of the enzyme, indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like. The compounds of the invention can also be useful in the treatment of obesity and ischemia.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) (see section on cytokines).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-$\beta$, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which is a combination of a compound of the invention and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the IDO enzyme in tissue samples, including human, and for identifying IDO enzyme ligands by inhibition binding of a labeled compound. Accordingly, the present invention includes IDO enzyme assays that contain such labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radiolabeled compounds will depend on the specific application of that radio-labeled compound. For example, for in vitro IDO enzyme labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the IDO enzyme. Accordingly, the ability of a test compound to compete with the radio-labeled compound for binding to the IDO enzyme directly correlates to its binding affinity.

Kits

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of IDO according to one or more of the assays provided herein.

EXAMPLES

Example 1

4-({2-[(Aminosulfonyl)amino]ethyl}amino)-N-(3-bromo-4-fluorophenyl)-N'-hydroxy-1,2,5-oxadiazole-3-carboximidamide

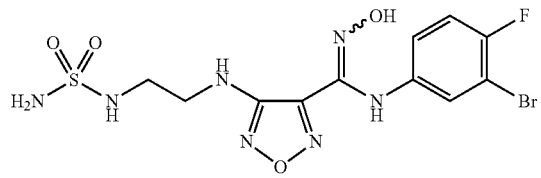 [SMILES: NS(=O)(=O)NCCNc1nonc1C(=NO)Nc1ccc(F)c(Br)c1]

Step A: 4-Amino-N'-hydroxy-1,2,5-oxadiazole-3-carboximidamide

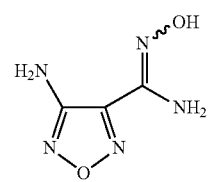

Malononitrile [Aldrich, product #M1407] (320.5 g, 5 mol) was added to water (7 L) preheated to 45° C. and stirred for 5 min. The resulting solution was cooled in an ice bath and sodium nitrite (380 g, 5.5 mol) was added. When the temperature reached 10° C., 6 N hydrochloric acid (55 mL) was added. A mild exothermic reaction ensued with the temperature reaching 16° C. After 15 min the cold bath was removed and the reaction mixture was stirred for 1.5 hrs at 16-18° C. The reaction mixture was cooled to 13° C. and 50% aqueous hydroxylamine (990 g, 15 mol) was added all at once. The temperature rose to 26° C. When the exothermic reaction subsided the cold bath was removed and stirring was continued for 1 hr at 26-27° C., then it was slowly brought to reflux. Reflux was maintained for 2 hrs and then the reaction mixture was allowed to cool overnight. The reaction mixture was stirred in an ice bath and 6 N hydrochloric acid (800 mL) was added in portions over 40 min to pH 7.0. Stirring was continued in the ice bath at 5° C. The precipitate was collected by filtration, washed well with water and dried in a vacuum oven (50° C.) to give the desired product (644 g, 90%). LCMS for $C_3H_6N_5O_2$ (M+H)$^+$: m/z=144.0. $^{13}$C NMR (75 MHz, CD$_3$OD): δ 156.0, 145.9, 141.3.

Step B:
4-Amino-N-hydroxy-1,2,5-oxadiazole-3-carboximidoyl chloride

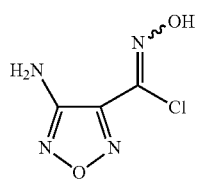

4-Amino-N'-hydroxy-1,2,5-oxadiazole-3-carboximidamide (422 g, 2.95 mol) was added to a mixture of water (5.9 L), acetic acid (3 L) and 6 N hydrochloric acid (1.475 L, 3 eq.) and this suspension was stirred at 42-45° C. until complete solution was achieved. Sodium chloride (518 g, 3 eq.) was added and this solution was stirred in an ice/water/methanol bath. A solution of sodium nitrite (199.5 g, 0.98 eq.) in water (700 mL) was added over 3.5 hrs while maintaining the temperature below 0° C. After complete addition stirring was continued in the ice bath for 1.5 hrs and then the reaction mixture was allowed to warm to 15° C. The precipitate was collected by filtration, washed well with water, taken in ethyl acetate (3.4 L), treated with anhydrous sodium sulfate (500 g) and stirred for 1 hr. This suspension was filtered through sodium sulfate (200 g) and the filtrate was concentrated on a rotary evaporator. The residue was dissolved in methyl t-butyl ether (5.5 L), treated with charcoal (40 g), stirred for 40 min and filtered through Celite. The solvent was removed in a rotary evaporator and the resulting product was dried in a vacuum oven (45° C.) to give the desired product (256 g, 53.4%). LCMS for $C_3H_4ClN_4O_2$ (M+H)$^+$: m/z=162.9. $^{13}$C NMR (100 MHz, CD$_3$OD): δ 155.8, 143.4, 129.7.

Step C: 4-Amino-N'-hydroxy-N-(2-methoxyethyl)-1,2,5-oxadiazole-3-carboximidamide

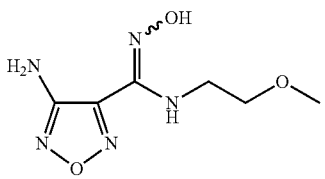

4-Amino-N-hydroxy-1,2,5-oxadiazole-3-carboximidoyl chloride (200.0 g, 1.23 mol) was mixed with ethyl acetate (1.2 L). At 0-5° C. 2-methoxyethylamine [Aldrich, product #143693] (119.0 mL, 1.35 mol) was added in one portion while stirring. The reaction temperature rose to 41° C. The reaction was cooled to 0-5° C. Triethylamine (258 mL, 1.84 mol) was added. After stirring 5 min, LCMS indicated reaction completion. The reaction solution was washed with water (500 mL) and brine (500 mL), dried over sodium sulfate, and concentrated to give the desired product (294 g, 119%) as a crude dark oil. LCMS for $C_6H_{12}N_5O_3$ (M+H)$^+$: m/z=202.3. $^1$H NMR (400 MHz, DMSO-d$_6$): δ 10.65 (s, 1H), 6.27 (s, 2H), 6.10 (t, J=6.5 Hz, 1H), 3.50 (m, 2H), 3.35 (d, J=5.8 Hz, 2H), 3.08 (s, 3H).

Step D: N'-Hydroxy-4-[(2-methoxyethyl)amino]-1,2,5-oxadiazole-3-carboximidamide

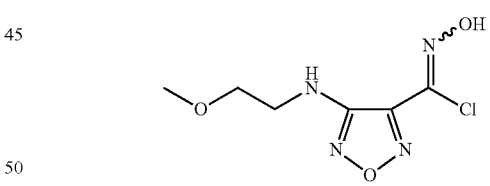

4-Amino-N'-hydroxy-N-(2-methoxyethyl)-1,2,5-oxadiazole-3-carboximidamide (248.0 g, 1.23 mol) was mixed with water (1 L). Potassium hydroxide (210 g, 3.7 mol) was added. The reaction was refluxed at 100° C. overnight (15 hours). TLC with 50% ethyl acetate (containing 1% ammonium hydroxide) in hexane indicated reaction completed (product Rf=0.6, starting material Rf=0.5). LCMS also indicated reaction completion. The reaction was cooled to room temperature and extracted with ethyl acetate (3×1 L). The combined ethyl acetate solution was dried over sodium sulfate and concentrated to give the desired product (201 g, 81%) as a crude off-white solid. LCMS for $C_6H_{12}N_5O_3$ (M+H)$^+$: m/z=202.3 $^1$H NMR (400 MHz, DMSO-d$_6$): δ 10.54 (s, 1H), 6.22 (s, 2H), 6.15 (t, J=5.8 Hz, 1H), 3.45 (t, J=5.3 Hz, 2H), 3.35 (m, 2H), 3.22 (s, 3H).

Step E: N-Hydroxy-4-[(2-methoxyethyl)amino]-1,2,5-oxadiazole-3-carboximidoyl chloride At room temperature N'-hydroxy-4-[(2-methoxyethyl)amino]-1,2,5-oxadiazole-3-carboximidamide (50.0 g, 0.226 mol) was dissolved in 6.0 M hydrochloric acid aqueous solution (250 mL, 1.5 mol). Sodium chloride (39.5 g, 0.676 mol) was added followed by water (250 mL) and ethyl acetate (250 mL). At 3-5° C. a previously prepared aqueous solution (100 mL) of sodium nitrite (15.0 g, 0.217 mol) was added slowly over 1 hr. The reaction was stirred at 3-8° C. for 2 hours and then room temperature over the weekend. LCMS indicated reaction completed. The reaction solution was extracted with ethyl acetate (2×200 mL). The combined ethyl acetate solution was dried over sodium sulfate and concentrated to give the desired product (49.9 g, 126%) as a crude white solid. LCMS for $C_6H_{10}ClN_4O_3$ (M+H)$^+$: m/z=221.0. $^1$H NMR (400 MHz, DMSO-d$_6$): δ 13.43 (s, 1H), 5.85 (t, J=5.6 Hz, 1H), 3.50 (t, J=5.6 Hz, 2H), 3.37 (dd, J=10.8, 5.6 Hz, 2H), 3.25 (s, 3H).

Step F: N-(3-Bromo-4-fluorophenyl)-N'-hydroxy-4-[(2-methoxyethyl)amino]-1,2,5-oxadiazole-3-carboximidamide

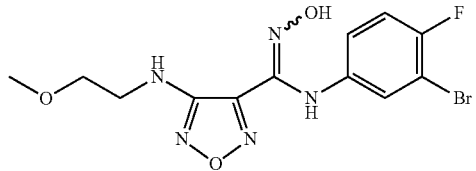 [SMILES: COCCNc1nonc1C(=NO)Nc1ccc(F)c(Br)c1]

N-Hydroxy-4-[(2-methoxyethyl)amino]-1,2,5-oxadiazole-3-carboximidoyl chloride (46.0 g, 0.208 mol) was mixed with water (300 mL). The mixture was heated to 60° C. 3-Bromo-4-fluoroaniline [Oakwood products, product #013091] (43.6 g, 0.229 mol) was added and stirred for 10 min. A warm sodium bicarbonate (26.3 g, 0.313 mol) solution (300 mL water) was added over 15 min. The reaction was stirred at 60° C. for 20 min. LCMS indicated reaction completion. The reaction solution was cooled to room temperature and extracted with ethyl acetate (2×300 mL). The combined ethyl acetate solution was dried over sodium sulfate and concentrated to give the desired product (76.7 g, 98%) as a crude brown solid. LCMS for $C_{12}H_{14}BrFN_5O_3$ (M+H)$^+$: m/z=374.0, 376.0. $^1$H NMR (400 MHz, DMSO-d$_6$): δ 11.55 (s, 1H), 8.85 (s, 1H), 7.16 (t, J=8.8 Hz, 1H), 7.08 (dd, J=6.1, 2.7 Hz, 1H), 6.75 (m, 1H), 6.14 (t, J=5.8 Hz, 1H), 3.48 (t, J=5.2 Hz, 2H), 3.35 (dd, J=10.8, 5.6 Hz, 2H), 3.22 (s, 3H).

Step G: 4-(3-Bromo-4-fluorophenyl)-3-{4-[(2-methoxyethyl)amino]-1,2,5-oxadiazol-3-yl}-1,2,4-oxadiazol-5(4H)-one

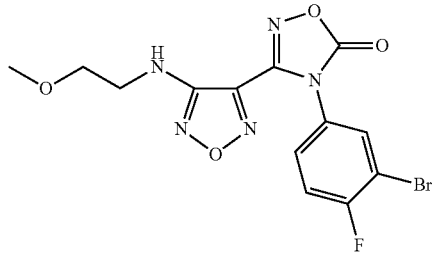 [SMILES: COCCNc1nonc1-c1noc(=O)n1-c1ccc(F)c(Br)c1]

A mixture of N-(3-bromo-4-fluorophenyl)-N'-hydroxy-4-[(2-methoxyethyl)amino]-1,2,5-oxadiazole-3-carboximidamide (76.5 g, 0.204 mol), 1,1'-carbonyldiimidazole (49.7 g, 0.307 mol), and ethyl acetate (720 mL) was heated to 60° C. and stirred for 20 min. LCMS indicated reaction completed. The reaction was cooled to room temperature, washed with 1 N HCl (2×750 mL), dried over sodium sulfate, and concentrated to give the desired product (80.4 g, 98%) as a crude brown solid. LCMS for $C_{13}H_{12}BrFN_5O_4$ (M+H)$^+$: m/z=400.0, 402.0. $^1$H NMR (400 MHz, DMSO-d$_6$): δ 7.94 (t, J=8.2 Hz, 1H), 7.72 (dd, J=9.1, 2.3 Hz, 1H), 7.42 (m, 1H), 6.42 (t, J=5.7 Hz, 1H), 3.46 (t, J=5.4 Hz, 2H), 3.36 (t, J=5.8 Hz, 2H), 3.26 (s, 3H).

Step H: 4-(3-Bromo-4-fluorophenyl)-3-{4-[(2-hydroxyethyl)amino]-1,2,5-oxadiazol-3-yl}-1,2,4-oxadiazol-5(4H)-one

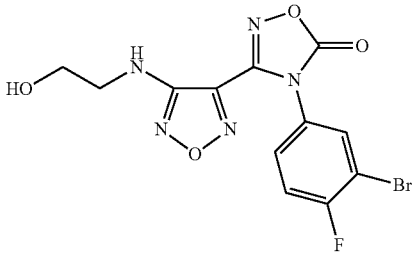 [SMILES: [N-]=[N+]=NCCNc1nonc1-c1noc(=O)n1-c1ccc(F)c(Br)c1]

4-(3-Bromo-4-fluorophenyl)-3-{4-[(2-methoxyethyl)amino]-1,2,5-oxadiazol-3-yl}-1,2,4-oxadiazol-5(4H)-one (78.4 g, 0.196 mol) was dissolved in dichloromethane (600 mL). At −67° C. boron tribromide (37 mL, 0.392 mol) was added over 15 min. The reaction was warmed up to −10° C. in 30 min. LCMS indicated reaction completed. The reaction was stirred at room temperature for 1 hour. At 0-5° C. the reaction was slowly quenched with saturated sodium bicarbonate solution (1.5 L) over 30 min. The reaction temperature rose to 25° C. The reaction was extracted with ethyl acetate (2×500 mL, first extraction organic layer is on the bottom and second extraction organic lager is on the top). The combined organic layers were dried over sodium sulfate and concentrated to give the desired product (75 g, 99%) as a crude brown solid. LCMS for $C_{12}H_{10}BrFN_5O_4$ (M+H)$^+$: m/z=386.0, 388.0. $^1$H NMR (400 MHz, DMSO-d$_6$): δ 8.08 (dd, J=6.2, 2.5 Hz, 1H), 7.70 (m, 1H), 7.68 (t, J=8.7 Hz, 1H), 6.33 (t, J=5.6 Hz, 1H), 4.85 (t, J=5.0 Hz, 1H), 3.56 (dd, J=10.6, 5.6 Hz, 2H), 3.29 (dd, J=11.5, 5.9 Hz, 2H).

Step I: 2-({4-[4-(3-Bromo-4-fluorophenyl)-5-oxo-4,5-dihydro-1,2,4-oxadiazol-3-yl]-1,2,5-oxadiazol-3-yl}amino)ethyl methanesulfonate

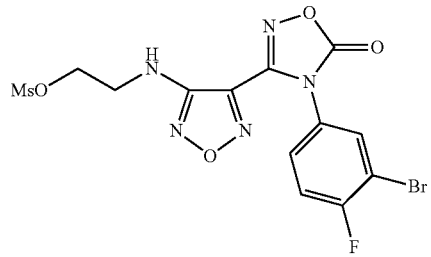

To a solution of 4-(3-bromo-4-fluorophenyl)-3-{4-[(2-hydroxyethyl)amino]-1,2,5-oxadiazol-3-yl}-1,2,4-oxadiazol-5(4H)-one (1.5 kg, 3.9 mol, containing also some of the corresponding bromo-compound) in ethyl acetate (12 L) was added methanesulfonyl chloride (185 mL, 2.4 mol) dropwise over 1 h at room temperature. Triethylamine (325 mL, 2.3 mol) was added dropwise over 45 min, during which time the reaction temperature increased to 35° C. After 2 h, the reaction mixture was washed with water (5 L), brine (1 L), dried over sodium sulfate, combined with 3 more reactions of the same size, and the solvents removed in vacuo to afford the desired product (7600 g, quantitative yield) as a tan solid. LCMS for $C_{13}H_{11}BrFN_5O_6SNa$ (M+Na)$^+$: m/z=485.9, 487.9. $^1$H NMR (400 MHz, DMSO-d$_6$): δ 8.08 (dd, J=6.2, 2.5 Hz, 1H), 7.72 (m, 1H), 7.58 (t, J=8.7 Hz, 1H), 6.75 (t, J=5.9 Hz, 1H), 4.36 (t, J=5.3 Hz, 2H), 3.58 (dd, J=11.2, 5.6 Hz, 2H), 3.18 (s, 3H).

Step J: 3-{4-[(2-Azidoethyl)amino]-1,2,5-oxadiazol-3-yl}-4-(3-bromo-4-fluorophenyl)-1,2,4-oxadiazol-5(4H)-one

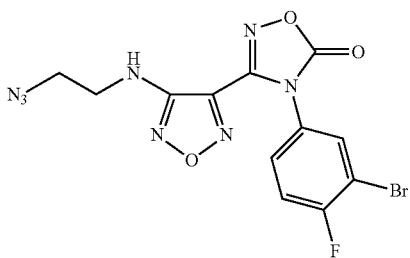

To a solution of 2-({4-[4-(3-bromo-4-fluorophenyl)-5-oxo-4,5-dihydro-1,2,4-oxadiazol-3-yl]-1,2,5-oxadiazol-3-yl}amino)ethyl methanesulfonate (2.13 kg, 4.6 mol, containing also some of the corresponding bromo-compound) in dimethylformamide (4 L) stirring in a 22 L flask was added sodium azide (380 g, 5.84 mol). The reaction was heated at 50° C. for 6 h, poured into ice/water (8 L), and extracted with 1:1 ethyl acetate:heptane (20 L). The organic layer was washed with water (5 L) and brine (5 L), and the solvents removed in vacuo to afford the desired product (1464 g, 77%) as a tan solid. LCMS for $C_{12}H_8BrFN_8O_3Na$ (M+Na)$^+$: m/z=433.0, 435.0. $^1$H NMR (400 MHz, DMSO-d$_6$): δ 8.08 (dd, J=6.2, 2.5 Hz, 1H), 7.72 (m, 1H), 7.58 (t, J=8.7 Hz, 1H), 6.75 (t, J=5.7 Hz, 1H), 3.54 (t, J=5.3 Hz, 2H), 3.45 (dd, J=11.1, 5.2 Hz, 2H).

Step K: 3-{4-[(2-Aminoethyl)amino]-1,2,5-oxadiazol-3-yl}-4-(3-bromo-4-fluorophenyl)-1,2,4-oxadiazol-5(4H)-one hydrochloride

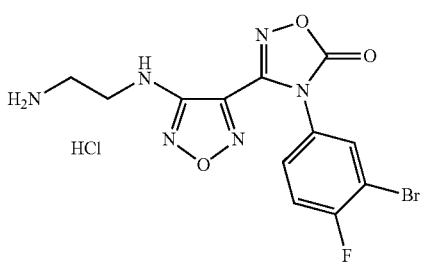 [SMILES: NCCNc1nonc1-c1noc(=O)n1-c1ccc(F)c(Br)c1 ; Cl]

Sodium iodide (1080 g, 7.2 mol) was added to 3-{4-[(2-azidoethyl)amino]-1,2,5-oxadiazol-3-yl}-4-(3-bromo-4-fluorophenyl)-1,2,4-oxadiazol-5(4H)-one (500 g, 1.22 mol) in methanol (6 L). The mixture was allowed to stir for 30 min during which time a mild exotherm was observed. Chlorotrimethylsilane (930 mL, 7.33 mol) was added as a solution in methanol (1 L) dropwise at a rate so that the temperature did not exceed 35° C., and the reaction was allowed to stir for 3.5 h at ambient temperature. The reaction was neutralized with 33 wt % solution of sodium thiosulfate pentahydrate in water (~1.5 L), diluted with water (4 L), and the pH adjusted to 9 carefully with solid potassium carbonate (250 g—added in small portions: watch foaming). Di-tert-butyl dicarbonate (318 g, 1.45 mol) was added and the reaction was allowed to stir at room temperature. Additional potassium carbonate (200 g) was added in 50 g portions over 4 h to ensure that the pH was still at or above 9. After stirring at room temperature overnight, the solid was filtered, triturated with water (2 L), and then MTBE (1.5 L). A total of 11 runs were performed (5.5 kg, 13.38 mol). The combined solids were triturated with 1:1 THF:dichloromethane (24 L, 4 runs in a 20 L rotary evaporator flask, 50° C., 1 h), filtered, and washed with dichloromethane (3 L each run) to afford an off-white solid. The crude material was dissolved at 55° C. tetrahydrofuran (5 mL/g), treated with decolorizing carbon (2 wt %) and silica gel (2 wt %), and filtered hot through celite to afford the product as an off-white solid (5122 g). The combined MTBE, THF, and dichloromethane filtrates were concentrated in vacuo and chromatographed (2 kg silica gel, heptane with a 0-100% ethyl acetate gradient, 30 L) to afford more product (262 g). The combined solids were dried to a constant weight in a convection oven (5385 g, 83%).

In a 22 L flask was charged hydrogen chloride (4 N solution in 1,4-dioxane, 4 L, 16 mol). tert-Butyl [2-({4-[4-(3-bromo-4-fluorophenyl)-5-oxo-4,5-dihydro-1,2,4-oxadiazol-3-yl]-1,2,5-oxadiazol-3-yl}amino)ethyl]carbamate (2315 g, 4.77 mol) was added as a solid in portions over 10 min. The slurry was stirred at room temperature and gradually became a thick paste that could not be stirred. After sitting overnight at room temperature, the paste was slurried in ethyl acetate (10 L), filtered, re-slurried in ethyl acetate (5 L), filtered, and dried to a constant weight to afford the desired product as a white solid (combined with other runs, 5 kg starting material charged, 4113 g, 95%). LCMS for $C_{12}H_{11}BrFN_6O_3$ (M+H)$^+$: m/z=384.9, 386.9. $^1$H NMR (400 MHz, DMSO-d$_6$): δ 8.12 (m, 4H), 7.76 (m, 1H), 7.58 (t, J=8.7 Hz, 1H), 6.78 (t, J=6.1 Hz, 1H), 3.51 (dd, J=11.8, 6.1 Hz, 2H), 3.02 (m, 2H).

Step L: tert-Butyl({[2-({4-[4-(3-bromo-4-fluorophenyl)-5-oxo-4,5-dihydro-1,2,4-oxadiazol-3-yl]-1,2,5-oxadiazol-3-yl}amino)ethyl}amino]sulfonyl)carbamate

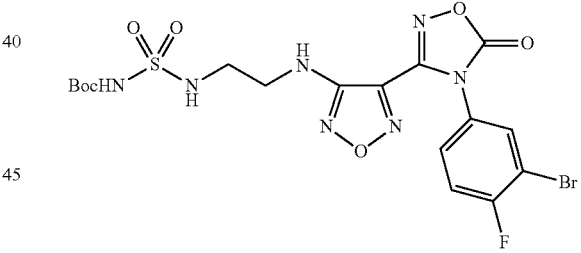

A 5 L round bottom flask was charged with chlorosulfonyl isocyanate [Aldrich, product #142662] (149 mL, 1.72 mol) and dichloromethane (1.5 L) and cooled using an ice bath to 2° C. tert-Butanol (162 mL, 1.73 mol) in dichloromethane (200 mL) was added dropwise at a rate so that the temperature did not exceed 10° C. The resulting solution was stirred at room temperature for 30-60 min to provide tert-butyl [chlorosulfonyl]carbamate.

A 22 L flask was charged with 3-{4-[(2-aminoethyl)amino]-1,2,5-oxadiazol-3-yl}-4-(3-bromo-4-fluorophenyl)-1,2,4-oxadiazol-5(4H)-one hydrochloride (661 g, 1.57 mol) and 8.5 L dichloromethane. After cooling to −15° C. with an ice/salt bath, the solution of tert-butyl [chlorosulfonyl]carbamate (prepared as above) was added at a rate so that the temperature did not exceed −10° C. (addition time 7 min). After stirring for 10 min, triethylamine (1085 mL, 7.78 mol) was added at a rate so that the temperature did not exceed −5° C. (addition time 10 min). The cold bath was removed, the reaction was allowed to warm to 10° C., split into two portions, and neutralized with 10% conc HCl (4.5 L each portion). Each portion was transferred to a 50 L reparatory funnel and diluted with ethyl acetate to completely dissolve the white solid (~25 L). The layers were separated, and the organic layer was washed with water (5 L), brine (5 L), and the solvents removed in vacuo to afford an off-white solid. The solid was triturated with MTBE (2×1.5 L) and dried to a constant weight to afford a white solid. A total of 4113 g starting material was processed in this manner (5409 g, 98%), $^1$H NMR (400 MHz, DMSO-d$_6$): δ 10.90 (s, 1H), 8.08 (dd, J=6.2, 2.5 Hz, 1H), 7.72 (m, 1H), 7.59 (t, J=8.6 Hz, 1H), 6.58 (t, J=5.7 Hz, 1H), 3.38 (dd, J=12.7, 6.2 Hz, 2H), 3.10 (dd, J=12.1, 5.9 Hz, 2H), 1.41 (s, 9H).

Step M: N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide

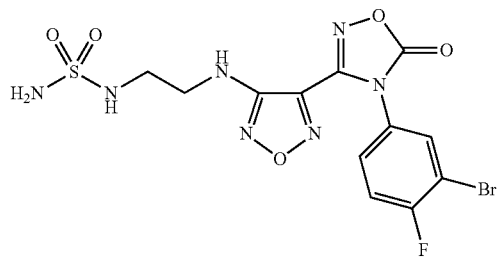 [SMILES: NS(=O)(=O)NCCNc1nonc1-c1noc(=O)n1-c1ccc(F)c(Br)c1]

To a 22 L flask containing 98:2 trifluoroacetic acid:water (8.9 L) was added tert-butyl({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (1931 g, 3.42 mol) in portions over 10 minutes. The resulting mixture was stirred at room temperature for 1.5 h, the solvents removed in vacuo, and chased with dichloromethane (2 L). The resulting solid was treated a second time with fresh 98:2 trifluoroacetic acid:water (8.9 L), heated for 1 h at 40-50° C., the solvents removed in vacuo, and chased with dichloromethane (3×2 L). The resulting white solid was dried in a vacuum drying oven at 50° C. overnight. A total of 5409 g was processed in this manner (4990 g, quant. yield). LCMS for $C_{12}H_{12}BrFN_7O_5S$ (M+H)$^+$: m/z=463.9, 465.9. $^1$H NMR (400 MHz, DMSO-d$_6$): δ 8.08 (dd, J=6.2, 2.5 Hz, 1H), 7.72 (m, 1H), 7.59 (t, J=8.7 Hz, 1H), 6.67 (t, J=5.9 Hz, 1H), 6.52 (t, J=6.0 Hz, 1H), 3.38 (dd, J=12.7, 6.3 Hz, 2H), 3.11 (dd, J=12.3, 6.3 Hz).

Step N: 4-({2-[(Aminosulfonyl)amino]ethyl}amino)-N-(3-bromo-4-fluorophenyl)-N'-hydroxy-1,2,5-oxadiazole-3-carboximidamide To a crude mixture of N-[2-({4-[4-(3-bromo-4-fluorophenyl)-5-oxo-4,5-dihydro-1,2,4-oxadiazol-3-yl]-1,2,5-oxadiazol-3-yl}amino)ethyl]sulfamide (2.4 mol) containing residual amounts of trifluoroacetic acid stirring in a 22 L flask was added THF (5 L). The resulting solution was cooled to 0° C. using an ice bath and 2 N NaOH (4 L) was added at a rate so that the temperature did not exceed 10° C. After stirring at ambient temperature for 3 h (LCMS indicated no starting material remained), the pH was adjusted to 3-4 with concentrated HCl (~500 mL). The THF was removed in vacuo, and the resulting mixture was extracted with ethyl acetate (15 L). The organic layer was washed with water (5 L), brine (5 L), and the solvents removed in vacuo to afford a solid. The solid was triturated with MTBE (2×2 L), combined with three other reactions of the same size, and dried overnight in a convection oven to afford a white solid (3535 g). The solid was recrystallized (3×22 L flasks, 2:1 water:ethanol, 14.1 L each flask) and dried in a 50° C. convection oven to a constant weight to furnish the title compound as an off-white solid (3290 g, 78%). LCMS for $C_{11}H_{14}BrFN_7O_4S$ (M+H)$^+$: m/z=437.9, 439.9. $^1$H NMR (400 MHz, DMSO-d$_6$): δ 11.51 (s, 1H), 8.90 (s, 1H), 7.17 (t, J=8.8 Hz, 1H), 7.11 (dd, J=6.1, 2.7 Hz, 1H), 6.76 (m, 1H), 6.71 (t, J=6.0 Hz, 1H), 6.59 (s, 2H), 6.23 (t, J=6.1 Hz, 1H), 3.35 (dd, J=10.9, 7.0 Hz, 2H), 3.10 (dd, J=12.1, 6.2 Hz, 2H).

Figure 3:
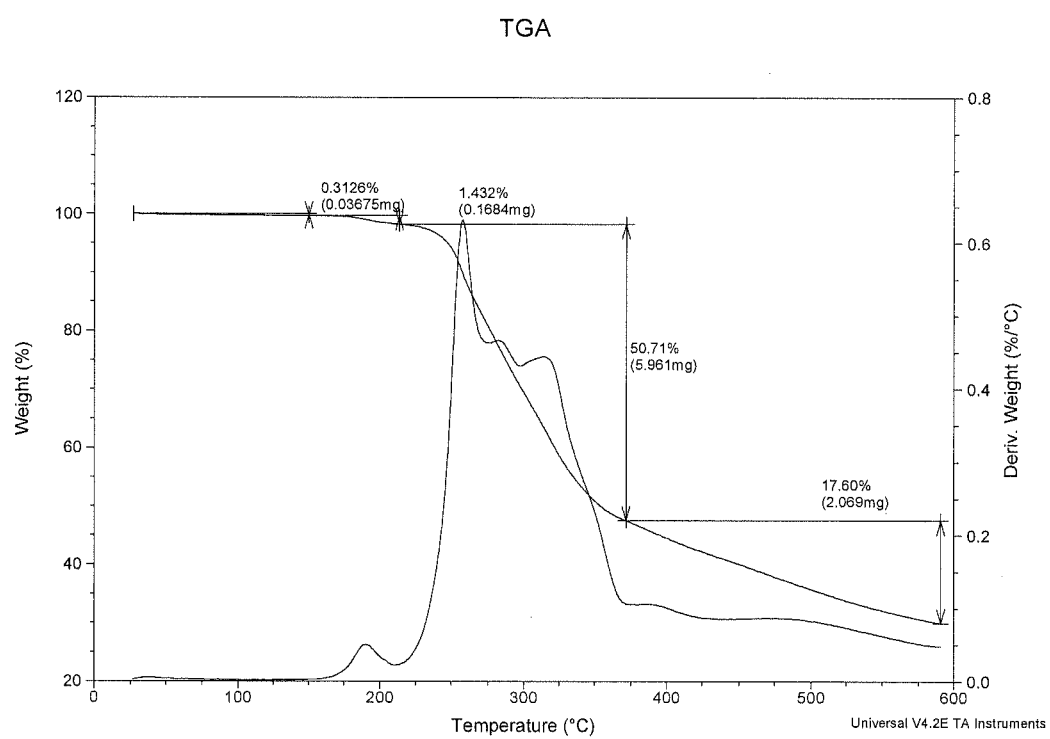
FIG. 3 shows TGA data characteristic of the compound of the invention prepared in Example 1.

The final product was an anhydrous crystalline solid. The water content was determined to be less than 0.1% by Karl Fischer titration. The X-ray powder diffraction (XRPD) pattern was determined (Rigaku MiniFlex Powder Diffractometer; Cu at 1.054056 Å with Kβ filter; start angle=3, stop angle=45, sampling=0.02, scan speed=2) and is shown in FIG. 1. A list of 2-theta peaks is provided in Table 1 below. The melting range of the solid was determined on a Mettler Toledo Differential Scanning Caloimetry (DSC) 822 instrument. The sample was heated from 40° C. to 240° C. at a heating rate of 10° C. per min. The DSC thermogram (FIG. 2) showed a $T_{onset}$ at 162.7° C. and $T_{peak}$ at 163.8° C. Thermogravimetric analysis (TGA) (FIG. 3) showed weight loss of 0.3%, heating from 20° C. to 150° C. at a heating rate of 10° C./min using a TA Instrument Q500.

TABLE 1

| 2-Theta | Height | H % |
|---|---|---|
| 3.9 | 74 | 1.1 |
| 7.2 | 119 | 1.8 |
| 13.4 | 180 | 2.8 |
| 14.0 | 150 | 2.3 |
| 15.9 | 85 | 1.3 |
| 18.4 | 903 | 13.9 |
| 18.9 | 1469 | 22.7 |
| 21.3 | 519 | 8 |
| 21.8 | 6472 | 100 |
| 22.7 | 516 | 8 |
| 23.9 | 2515 | 38.9 |
| 24.8 | 804 | 12.4 |
| 25.3 | 182 | 2.8 |
| 27.4 | 476 | 7.4 |
| 28.6 | 354 | 5.5 |
| 29.2 | 1767 | 27.3 |
| 29.9 | 266 | 4.1 |
| 30.6 | 773 | 11.9 |
| 31.2 | 379 | 5.8 |
| 31.6 | 291 | 4.5 |
| 32.7 | 144 | 2.2 |
| 33.5 | 221 | 3.4 |
| 36.4 | 469 | 7.2 |
| 37.6 | 152 | 2.3 |
| 38.7 | 1381 | 21.3 |
| 41.0 | 153 | 2.4 |
| 42.1 | 382 | 5.9 |
| 43.6 | 527 | 8.1 |
| 44.4 | 1080 | 16.7 |

Example 2

N-(3-Bromo-4-fluorophenyl)-N'-hydroxy-4-({2-[(methylsulfonyl)amino]ethyl}amino)-1,2,5-oxadiazole-3-carboximidamide

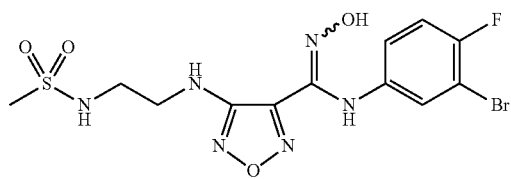 [SMILES: CS(=O)(=O)NCCNc1nonc1C(=NO)Nc1ccc(F)c(Br)c1]

The title compound was prepared according to the procedure of Example 17 step E, using N'-hydroxy-4-({2-[(methylsulfonyl)amino]ethyl}amino)-1,2,5-oxadiazole-3-carboximidamide and 3-bromo-4-fluoroaniline [Oakwood Products, Inc., product #013091] as the starting materials. LCMS for $C_{12}H_{15}BrFN_6O_4S$ (M+H)$^+$: m/z=437.0, 439.0. $^1$H NMR (400 MHz, DMSO-$d_6$): δ 11.49 (s, 1H), 8.90 (s, 1H), 7.17 (m, 2H), 7.09 (dd, J=6.3, 2.5 Hz, 1H), 6.26 (t, J=6.1 Hz, 1H), 3.33 (m, 2H), 3.13 (q, J=6.0 Hz, 2H), 2.89 (s, 3H).

Example 3

4-({3-[(Aminosulfonyl)amino]propyl}amino)-N-(3-bromo-4-fluorophenyl)-N'-hydroxy-1,2,5-oxadiazole-3-carboximidamide

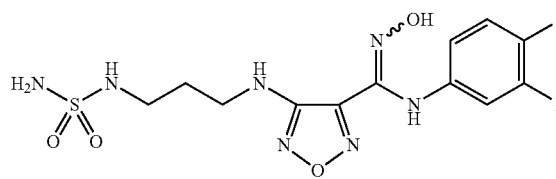

Step A: 3-(4-Amino-1,2,5-oxadiazol-3-yl)-4-(3-bromo-4-fluorophenyl)-1,2,4-oxadiazol-5(4H)-one

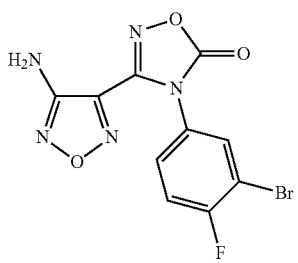 [SMILES: Nc1nonc1-c1noc(=O)n1-c1ccc(F)c(Br)c1]

The desired compound was prepared according to the procedure of Example 5, step A, using 4-amino-N-(3-bromo-4-fluorophenyl)-N'-hydroxy-1,2,5-oxadiazole-3-carboximidamide [see U.S. Pat. App. Pub. No. 2006/0258719] as the starting material in 98% yield. LCMS for $C_{10}H_6BrFN_5O_3$ (M+H)$^+$: m/z=342.0, 344.0. $^1$H NMR (400 MHz, DMSO-$d_6$): δ 8.06 (dd, J=6.2, 2.5 Hz, 1H), 7.72-7.67 (m, 1H), 7.58 (dd, J=8.7, 8.7 Hz, 1H), 6.60 (s, 2H).

Step B: N-{4-[4-(3-Bromo-4-fluorophenyl)-5-oxo-4,5-dihydro-1,2,4-oxadiazol-3-yl]-1,2,5-oxadiazol-3-yl}-2,2,2-trifluoroacetamide

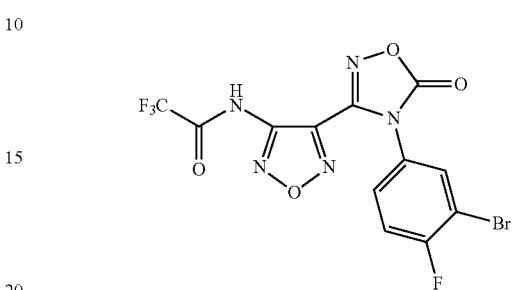

The desired compound was prepared according to the procedure of Example 5, step B, using 3-(4-amino-1,2,5-oxadiazol-3-yl)-4-(3-bromo-4-fluorophenyl)-1,2,4-oxadiazol-5(4H)-one as the starting material in 81% yield. LCMS for $C_{12}H_5BrF_4N_5O_4$ (M+H)$^+$: m/z=437.9, 439.9, $^1$H NMR (400 MHz, DMSO-$d_6$): δ 7.92-7.89 (m, 1H), 7.54-7.52 (m, 2H).

Step C: 4-(3-Bromo-4-fluorophenyl)-3-{4-[(3-methoxypropyl)amino]-1,2,5-oxadiazol-3-yl}-1,2,4-oxadiazol-5(4H)-one

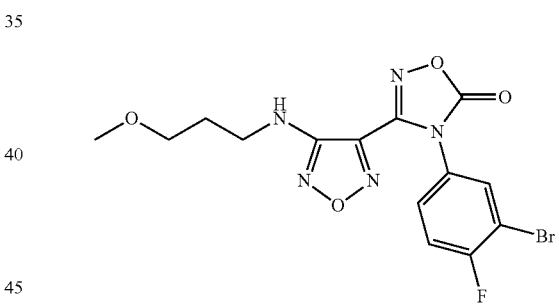

A solution of 3-methoxypropan-1-ol [Fluka product #38457] (3.1 mL, 32 mmol) and triphenylphosphine (8.4 g, 32 mmol) in tetrahydrofuran (93 mL) at 0° C. was treated with diisopropyl azodicarboxylate (6.7 mL, 34 mmol) dropwise. The reaction mixture was stirred at 0° C. for 15 min, treated with a solution of N-{4-[4-(3-bromo-4-fluorophenyl)-5-oxo-4,5-dihydro-1,2,4-oxadiazol-3-yl]-1,2,5-oxadiazol-3-yl}-2,2,2-trifluoroacetamide (10 g, 23 mmol) in tetrahydrofuran (47 mL), and stirred at 25° C. for 72 h. The reaction mixture was concentrated, diluted with ethyl acetate (200 mL), treated with trifluoroacetic acid (20 mL) and water (20 mL), and heated at 50° C. for 6 h. The reaction mixture was concentrated, rediluted with ethyl acetate (200 mL) and washed with water (3×80 mL), saturated sodium bicarbonate (2×80 mL) and brine (80 mL), dried over anhydrous sodium sulfate, filtered, and concentrated to a crude residue. This material was purified on silica gel to give the desired product (6.4 g, 54%) as a white solid. LCMS for $C_{14}H_{14}BrFN_5O_4$ (M+H)$^+$: m/z=414.0, 416.0.

Step D: 4-(3-Bromo-4-fluorophenyl)-3-{4-[(3-hydroxypropyl)amino]-1,2,5-oxadiazol-3-yl}-1,2,4-oxadiazol-5(4H)-one

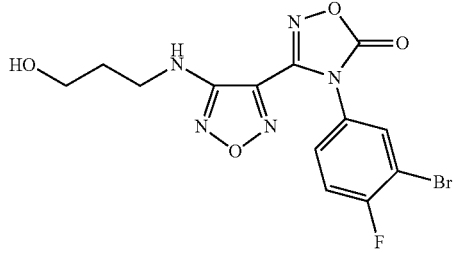 [SMILES: O=c1onc(-c2nonc2NCCCO)n1-c1ccc(F)c(Br)c1]

A solution of 4-(3-bromo-4-fluorophenyl)-3-{4-[(3-methoxypropyl)amino]-1,2,5-oxadiazol-3-yl}-1,2,4-oxadiazol-5(4H)-one (6.3 g, 14 mmol) in dichloromethane (60 mL) at −78° C. was treated with 1 M boron tribromide in dichloromethane (28 mL, 28 mmol) and stirred at 25° C. for 2 h. The reaction mixture was cooled to 0° C. and quenched with saturated sodium bicarbonate (100 mL). The aqueous layer was separated and extracted with dichloromethane (2×150 mL). The combined organic layers were washed with brine (100 mL), dried over anhydrous sodium sulfate, filtered, and concentrated to a crude off-white solid. This material was purified on silica gel to give the desired product (4.0 g, 73%) as a white solid. LCMS for $C_{13}H_{12}BrFN_5O_4$ (M+H)$^+$: m/z=400.0, 402.0. $^1$H NMR (400 MHz, DMSO-$d_6$): δ 8.07 (dd, J=6.2, 2.5 Hz, 1H), 7.72-7.68 (m, 1H), 7.59 (dd, J=8.8, 8.6 Hz, 1H), 6.54 (t, J=5.7 Hz, 1H), 4.60 (t, J=5.1 Hz, 1H), 3.48-3.43 (m, 2H), 3.32-3.26 (m, 2H), 1.74-1.67 (m, 2H).

Step E: 3-{4-[(3-Azidopropyl)amino]-1,2,5-oxadiazol-3-yl}-4-(3-bromo-4-fluorophenyl)-1,2,4-oxadiazol-5(4H)-one

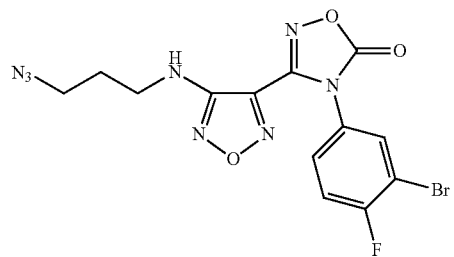 [SMILES: [N-]=[N+]=NCCCNc1nonc1-c1noc(=O)n1-c1ccc(F)c(Br)c1]

A solution of 4-(3-bromo-4-fluorophenyl)-3-{4-[(3-hydroxypropyl)amino]-1,2,5-oxadiazol-3-yl}-1,2,4-oxadiazol-5(4H)-one (3.0 g, 7.5 mmol) in dichloromethane (27 mL) was treated with methanesulfonyl chloride (0.75 mL, 9.7 mmol) and N,N-diisopropylethylamine (2.6 mL, 15 mmol) and stirred at 25° C. for 2 h. The reaction mixture was diluted with water (20 mL) and extracted with dichloromethane (20 mL). The organic layer was separated, dried over anhydrous sodium sulfate, filtered, and concentrated to give the mesylate which was used without further purification. A solution of the crude mesylate in N,N-dimethylformamide (24 mL) was treated with sodium azide (0.73 g, 11 mmol) and heated at 85° C. for 2 h. The reaction mixture was diluted with ethyl acetate (300 mL) and washed with water (100 mL), saturated sodium bicarbonate (100 mL), and brine (100 mL), dried over anhydrous sodium sulfate, filtered, and concentrated to give the desired product (3.2 g, 99%). This material was used without further purification. LCMS for $C_{13}H_{10}BrFN_8O_3Na$ (M+Na)$^+$: m/z=446.9, 448.9.

Step F: 3-{4-[(3-Aminopropyl)amino]-1,2,5-oxadiazol-3-yl}-4-(3-bromo-4-fluorophenyl)-1,2,4-oxadiazol-5(4H)-one hydroiodide

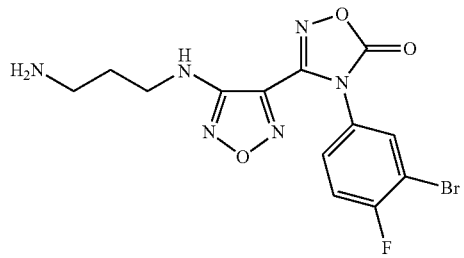

A solution of 3-{4-[(3-azidopropyl)amino]-1,2,5-oxadiazol-3-yl}-4-(3-bromo-4-fluorophenyl)-1,2,4-oxadiazol-5(4H)-one (2.0 g, 4.7 mmol) in methanol (36 mL) was treated with sodium iodide (4.2 g, 28 mmol) and stirred at 25° C. for 5 min. The reaction mixture was treated with a solution of chlorotrimethylsilane (3.6 mL, 28 mmol) in methanol (7 mL) dropwise and stirred at 25° C. for 40 min. The reaction mixture was slowly poured into a solution of sodium thiosulfate (5.0 g, 32 mmol) in water (200 mL) that was cooled at 0° C. The solid that precipitated was filtered, washed with water, and dried to give the desired product (2.3 g, 93%) as a solid. LCMS for $C_{13}H_{13}BrFN_6O_3$ (M+H)$^+$: m/z=399.0, 401.0. $^1$H NMR (400 MHz, DMSO-$d_6$): δ 8.08 (dd, J=6.1, 2.3 Hz, 1H), 7.74-7.70 (m, 1H), 7.60 (dd, J=8.8, 8.6 Hz, 1H), 7.22 (br s, 2H), 6.69 (br s, 1H), 2.81-2.77 (m, 2H), 1.86-1.79 (m, 2H).

Step G: N-[3-({4-[4-(3-Bromo-4-fluorophenyl)-5-oxo-4,5-dihydro-1,2,4-oxadiazol-3-yl]-1,2,5-oxadiazol-3-yl}amino)propyl]sulfamide

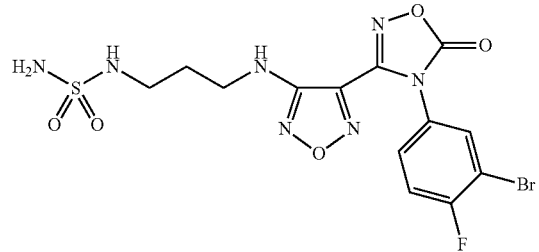 [SMILES: NS(=O)(=O)NCCCNc1nonc1-c1noc(=O)n1-c1ccc(F)c(Br)c1]

A solution of 3-{4-[(3-aminopropyl)amino]-1,2,5-oxadiazol-3-yl}-4-(3-bromo-4-fluorophenyl)-1,2,4-oxadiazol-5(4H)-one hydroiodide (150 mg, 0.28 mmol) and sulfamide (160 mg, 1.7 mmol) in pyridine (2.5 mL) was heated in a microwave at 130° C. for 10 min. The reaction mixture was concentrated to give a crude residue. This material was purified by preparative LCMS to give the desired product (96 mg, 71%) as a solid. LCMS for $C_{13}H_{14}BrFN_7O_5S$ (M+H)$^+$: m/z=478.0, 480.0. $^1$H NMR (400 MHz, DMSO-$d_6$): δ 8.07 (dd, J=6.2, 2.5 Hz, 1H), 7.73-7.69 (m, 1H), 7.59 (dd, J=8.8, 8.6 Hz, 1H), 6.57-6.51 (m, 4H), 3.31-3.26 (m, 2H), 2.92-2.87 (m, 2H), 1.79-1.72 (m, 2H).

Step H: 4-({3-[(Aminosulfonyl)amino]propyl}amino)-N-(3-bromo-4-fluorophenyl)-N'-hydroxy-1,2,5-oxadiazole-3-carboximidamide A solution of N-[3-({4-[4-(3-bromo-4-fluorophenyl)-5-oxo-4,5-dihydro-1,2,4-oxadiazol-3-yl]-1,2,5-oxadiazol-3-yl}amino)propyl]sulfamide (35 mg, 73 μmol) in methanol (1 mL) was treated with 2 M NaOH (0.3 mL, 0.6 mmol) and stirred at 25° C. for 30 min. The reaction mixture was treated with acetic acid (50 μL, 0.9 mmol), filtered, and purified by preparative LCMS to give the desired product (14 mg, 42%) as a solid. LCMS for $C_{12}H_{16}BrFN_7O_4S$ (M+H)$^+$: m/z=451.8, 453.9, $^1$H NMR (400 MHz, DMSO-$d_6$): δ 11.5 (s, 1H), 8.89 (s, 1H), 7.17 (dd, J=8.8, 8.6 Hz, 1H), 7.09 (dd, J=6.1, 2.7 Hz, 1H), 6.76-6.72 (m, 1H), 6.56 (dd, J=6.1, 6.1 Hz, 1H), 6.51 (s, 2H), 6.17 (dd, J=5.9, 5.9 Hz, 1H), 3.27-3.21 (m, 2H), 2.94-2.88 (m, 2H), 1.78-1.71 (m, 2H).

Example 4

N-(3-Bromo-4-fluorophenyl)-N'-hydroxy-4-({3-[(methylsulfonyl)amino]propyl}amino)-1,2,5-oxadiazole-3-carboximidamide

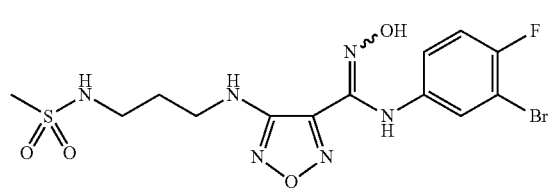 [SMILES: CS(=O)(=O)NCCCNc1nonc1C(=NO)Nc1ccc(F)c(Br)c1]

Step A: tert-Butyl {3-[(methylsulfonyl)amino]propyl}carbamate

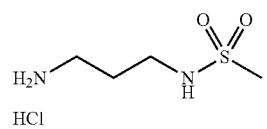

The desired compound was prepared according to the procedure of Example 17, step A, using N-(3-aminopropyl)(tert-butoxy)carboxamide [Aldrich product #436992] as the starting material in 70% yield. LCMS for $C_4H_{13}N_2O_2S$ ([M-Boc+H]+H)$^+$: m/z=153.1.

Step B: N-(3-Aminopropyl)methanesulfonamide hydrochloride

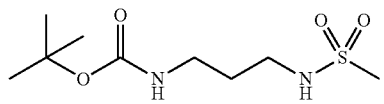 [SMILES: CC(C)(C)OC(=O)NCCCNS(C)(=O)=O]

The desired compound was prepared according to the procedure of Example 17, step B, using tert-butyl {3-[(methylsulfonyl)amino]propyl}carbamate as the starting material. LCMS for $C_4H_{13}N_2O_2S$ (M+H)$^+$: m/z=153.1.

Step C: 4-Amino-N'-hydroxy-N-{3-[(methylsulfonyl)amino]propyl}-1,2,5-oxadiazole-3-carboximidamide

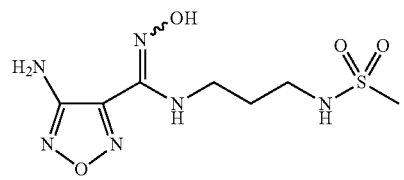 [SMILES: CS(=O)(=O)NCCCNC(=NO)c1nonc1N]

The desired compound was prepared according to the procedure of Example 17, step C, using N-(3-aminopropyl)methanesulfonamide hydrochloride and 4-amino-N-hydroxy-1,2,5-oxadiazole-3-carboximidoyl chloride [made according to Example 1, steps A through B] as the starting materials in 19% yield.

Step D: N'-Hydroxy-4-({3-[(methylsulfonyl)amino]propyl}amino)-1,2,5-oxadiazole-3-carboximidamide

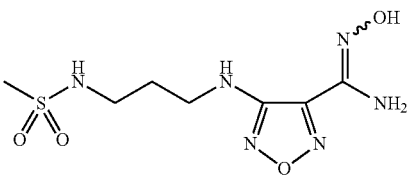 [SMILES: CS(=O)(=O)NCCCNc1nonc1C(N)=NO]

The desired compound was prepared according to the procedure of Example 17, step D, using 4-amino-N'-hydroxy-N-{3-[(methylsulfonyl)amino]propyl}-1,2,5-oxadiazole-3-carboximidamide as the starting material. LCMS for $C_7H_{15}N_6O_4S$ (M+H)$^+$: m/z=279.0.

Step E: N-(3-Bromo-4-fluorophenyl)-N'-hydroxy-4-({3-[(methylsulfonyl)amino]propyl}amino)-1,2,5-oxadiazole-3-carboximidamide The title compound was prepared according to the procedure of Example 17, step E, using N'-hydroxy-4-({3-[(methylsulfonyl)amino]propyl}amino)-1,2,5-oxadiazole-3-carboximidamide and 3-bromo-4-fluoroaniline [Oakwood Products, Inc., product #013091] as the starting materials in 12% yield. LCMS for $C_{13}H_{17}BrFN_6O_4S$ (M+H)$^+$: m/z=451.0, 453.0. $^1$H NMR (400 MHz, CD$_3$OD): δ 7.12 (dd, J=5.9, 2.4 Hz, 1H), 7.05 (t, J=8.7 Hz, 1H), 6.83 (m, 1H), 3.39 (t, J=6.8 Hz, 2H), 3.14 (t, J=6.6 Hz, 2H), 2.94 (s, 3H), 1.87 (m, 2H).

Example 5

4-({2-[(Aminosulfonyl)amino]ethyl}amino)-N-(3-chloro-4-fluorophenyl)-N'-hydroxy-1,2,5-oxadiazole-3-carboximidamide

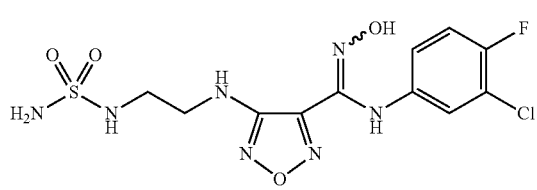

Step A: 3-(4-Amino-1,2,5-oxadiazol-3-yl)-4-(3-chloro-4-fluorophenyl)-1,2,4-oxadiazol-5(4H)-one

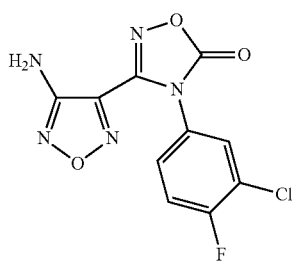 [SMILES: Nc1nonc1-c1noc(=O)n1-c1ccc(F)c(Cl)c1]

A solution of 4-amino-N-(3-chloro-4-fluorophenyl)-N'-hydroxy-1,2,5-oxadiazole-3-carboximidamide (80 g, 0.29 mol) [see US Pat. App. Pub. No. 2006/0258719] in tetrahydrofuran (500 mL) was treated with a solution of 1,1'-carbonyldiimidazole (53 g, 0.32 mol) in tetrahydrofuran (200 mL) and heated at reflux for 1 h. The reaction mixture was cooled to 25° C. and concentrated to the point where a large amount of solid precipitated. The heterogeneous mixture was diluted with ethyl acetate (1.5 L) and washed with 1 N HCl (2×300 mL), water (300 mL), and brine (200 mL). The organic layer was separated, dried over anhydrous sodium sulfate, filtered, and concentrated to give the desired product (88 g, quantitative) as an off-white solid. This material was used without further purification. LCMS for $C_{10}H_6ClFN_5O_3$ (M+H)$^+$: m/z=298.0. $^1$H NMR (400 MHz, DMSO-d$_6$): δ 7.96 (dd, J=6.6, 2.3 Hz, 1H), 7.69-7.60 (m, 2H), 6.60 (s, 2H).

Step B: N-{4-[4-(3-Chloro-4-fluorophenyl)-5-oxo-4,5-dihydro-1,2,4-oxadiazol-3-yl]-1,2,5-oxadiazol-3-yl}-2,2,2-trifluoroacetamide

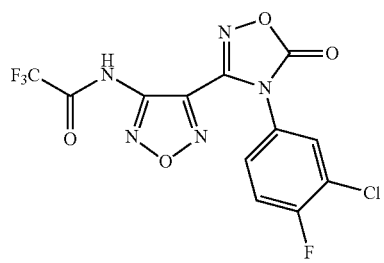 [SMILES: O=C(Nc1nonc1-c1noc(=O)n1-c1ccc(F)c(Cl)c1)C(F)(F)F]

A solution of 3-(4-amino-1,2,5-oxadiazol-3-yl)-4-(3-chloro-4-fluorophenyl)-1,2,4-oxadiazol-5(4H)-one (15 g, 50 mmol) in dichloromethane (120 mL) was treated with trifluoroacetic anhydride (14 mL, 100 mmol), cooled to 0° C., and treated with pyridine (8.2 mL, 100 mmol). The reaction mixture was stirred at 25° C. for 10 min, cooled to 0° C., and quenched with water (10 mL). The reaction mixture was diluted with ethyl acetate (500 mL) and washed with 1 N HCl (300 mL), water (2×200 mL), and brine (200 mL). The organic layer was separated, dried over anhydrous sodium sulfate, filtered, and concentrated to ~50 mL volume. This solution was warmed (~40-50° C.) and treated with hexanes (600 mL) under vigorous stirring, followed by petroleum ether (200 mL). The mixture was stirred at 0° C. for 30 min and the solid was collected by filtration, washed with hexanes, and dried to give the desired product (19.7 g, 99%) as a white solid. LCMS for $C_{12}H_5ClF_4N_5O_4$ (M+H)$^+$: m/z=394.0. $^1$H NMR (400 MHz, DMSO-d$_6$): δ 7.82 (dd, J=6.6, 2.5 Hz, 1H), 7.59 (dd, J=9.0, 9.0 Hz, 1H), 7.52-7.47 (m, 1H).

Step C: 4-(3-Chloro-4-fluorophenyl)-3-(4-{[2-(tritylamino)ethyl]amino}-1,2,5-oxadiazol-3-yl)-1,2,4-oxadiazol-5(4H)-one

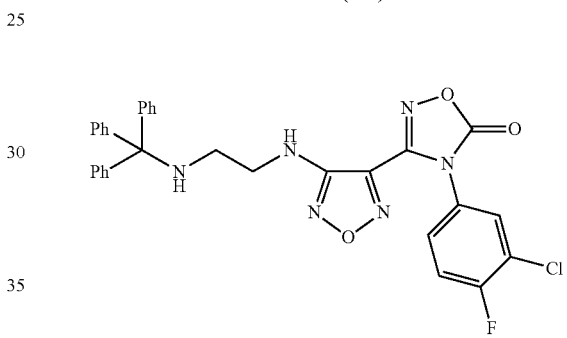

A solution of 2-(tritylamino)ethanol (10 g, 33 mmol) [EP599220 and J. Org. Chem. (2001), 66, 7615] and triphenylphosphine (8.7 g, 33 mmol) in tetrahydrofuran (65 mL) at 0° C. was treated with diisopropyl azodicarboxylate (7.0 mL, 35 mmol) dropwise. The reaction mixture was stirred at 0° C. for 15 min, treated with a solution of N-{4-[4-(3-chloro-4-fluorophenyl)-5-oxo-4,5-dihydro-1,2,4-oxadiazol-3-yl]-1,2,5-oxadiazol-3-yl}-2,2,2-trifluoroacetamide (9.3 g, 24 mmol) in tetrahydrofuran (28 mL), and stirred at 25° C. for 16 h. The reaction mixture was concentrated, diluted with ethyl acetate (350 mL), cooled to 0° C., treated with 1 N HCl (200 mL), and stirred at 25° C. for 1 h. The reaction mixture was treated with additional 1 N HCl (150 mL) and stirred at 25° C. for 3 h. The organic layer was separated, washed with saturated sodium bicarbonate (200 mL) and brine (100 mL), dried over anhydrous sodium sulfate, filtered, and concentrated to a yellow foam which was reconcentrated from hexanes to give an oily solid. The oily solid was treated with methyl tert-butyl ether (50 mL) and stirred to give a heterogeneous mixture. The solid was filtered, washed with methyl tert-butyl ether (30 mL), and dried to give the desired product (10 g, 74%) as a white solid. LCMS for $C_{31}H_{24}ClFN_6O_3Na$ (M+Na)$^+$: m/z=605.2. $^1$H NMR (300 MHz, DMSO-d$_6$): δ 7.97 (dd, J=6.7, 2.6 Hz, 1H), 7.71-7.66 (m, 1H), 7.60 (dd, J=9.1, 8.8 Hz, 1H), 7.40-7.37 (m, 6H), 7.28-7.23 (m, 6H), 7.18-7.12 (m, 3H), 6.59 (dd, J=5.9, 5.6 Hz, 1H), 3.37-3.31 (m, 2H), 2.96 (dd, J=7.6, 7.6 Hz, 1H), 2.27-2.19 (m, 2H).

Step D: 3-{4-[(2-Aminoethyl)amino]-1,2,5-oxadiazol-3-yl}-4-(3-chloro-4-fluorophenyl)-1,2,4-oxadiazol-5(4H)-one hydrochloride

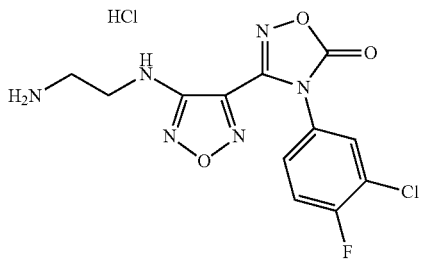 [SMILES: Cl ; NCCNc1nonc1-c1noc(=O)n1-c1ccc(F)c(Cl)c1]

A premixed solution of triisopropylsilane (3.4 mL, 17 mmol) and trifluoroacetic acid (44 mL, 570 mmol) was added to 4-(3-chloro-4-fluorophenyl)-3-(4-{[2-(tritylamino)ethyl]amino}-1,2,5-oxadiazol-3-yl)-1,2,4-oxadiazol-5(4H)-one (6.5 g, 11 mmol) and the resulting suspension was stirred at 25° C. for 30 min. The reaction mixture was filtered and washed with trifluoroacetic acid. The filtrate was concentrated to an oil which was diluted with methanol (25 mL), cooled to 0° C., treated with 4 M HCl in 1,4-dioxane (14 mL), and stirred at 25° C. for 15 min. The mixture was concentrated to a solid that was treated with diethyl ether (50 mL) and filtered. The solid was washed with diethyl ether (50 mL) and dried to give the desired product (4.1 g, 98%) as a white solid. LCMS for $C_{12}H_{11}ClFN_6O_3$ (M+H)$^+$: m/z=341.1. $^1$H NMR (300 MHz, DMSO-d$_6$): δ 8.05-8.00 (m, 4H), 7.75-7.69 (m, 1H), 7.64 (dd, J=9.1, 8.8 Hz, 1H), 6.77 (dd, J=5.9, 5.9 Hz, 1H), 3.54-3.47 (m, 2H), 3.04-2.99 (m, 2H).

Step E: N-[2-({4-[4-(3-Chloro-4-fluorophenyl)-5-oxo-4,5-dihydro-1,2,4-oxadiazol-3-yl]-1,2,5-oxadiazol-3-yl}amino)ethyl]sulfamide

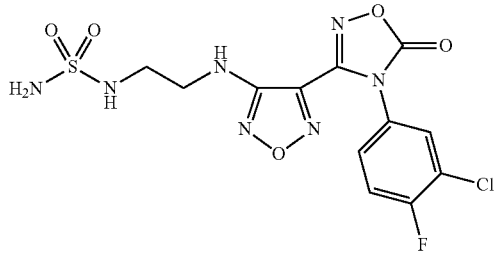

A solution of chlorosulfonyl isocyanate (2.0 mL, 23 mmol) in dichloromethane (70 mL) was treated with t-butyl alcohol (2.2 mL, 23 mmol) at 0° C. and stirred at 25° C. for 1 h. This mixture was added to a suspension of 3-{4-[(2-aminoethyl)amino]-1,2,5-oxadiazol-3-yl}-4-(3-chloro-4-fluorophenyl)-1,2,4-oxadiazol-5(4H)-one hydrochloride (4.3 g, 11 mmol) in dichloromethane (70 mL). The reaction mixture was treated with a solution of triethylamine (6.3 mL, 45 mmol) in dichloromethane (20 mL) at 0° C. and stirred at 25° C. for 3 h. The reaction mixture was diluted with 0.1 N HCl and extracted with ethyl acetate (2×100 mL). The combined organic layers were washed with brine (100 mL), dried over anhydrous sodium sulfate, filtered, and concentrated to a white solid. The white solid was diluted with dichloromethane (100 mL), treated with trifluoroacetic acid (20 mL), and stirred at 25° C. for 3 h. The reaction mixture was concentrated to a crude residue that was purified by silica gel chromatography to give the desired product (3.7 g, 78%) as a white solid. LCMS for $C_{12}H_{12}ClFN_7O_5S$ (M+H)$^+$: m/z=420.0. $^1$H NMR (300 MHz, DMSO-d$_6$): δ 7.98 (dd, J=6.4, 2.1 Hz, 1H), 7.70-7.60 (m, 2H), 6.66 (t, J=5.9 Hz, 1H), 6.57 (s, 2H), 6.52 (t, J=5.9 Hz, 1H), 3.42-3.35 (m, 2H), 3.13-3.06 (m, 2H).

Step F: 4-({2-[(Aminosulfonyl)amino]ethyl}amino)-N-(3-chloro-4-fluorophenyl)-N'-hydroxy-1,2,5-oxadiazole-3-carboximidamide A solution of N-[2-({4-[4-(3-chloro-4-fluorophenyl)-5-oxo-4,5-dihydro-1,2,4-oxadiazol-3-yl]-1,2,5-oxadiazol-3-yl}amino)ethyl]sulfamide (3.7 g, 8.8 mmol) in methanol (70 mL) was treated with 2 M NaOH (18 mL, 35 mmol) and stirred at 25° C. for 2 h. The reaction mixture was quenched with 6 N HCl to pH~7 and the methanol was removed under reduced pressure. The solid that precipitated was filtered and washed with water to give the desired product (3.2 g, 92%) as a white solid. LCMS for $C_{11}H_{14}ClFN_7O_4S$ (M+H)$^+$: m/z=394.0. $^1$H NMR (400 MHz, DMSO-d$_6$): δ 7.96 (dd, J=6.8, 2.1 Hz, 0.05H), 7.32-7.29 (m, 0.1H), 7.18 (dd, J=9.1, 9.1 Hz, 0.95H), 6.93 (dd, J=6.4, 2.7 Hz, 0.95H), 6.71-6.66 (m, 0.95H), 6.33 (br s, 1H), 3.35-3.27 (m, 2H), 3.10-3.06 (m, 2H).

Example 6

N-(3-Chloro-4-fluorophenyl)-N'-hydroxy-4-({2-[(methylsulfonyl)amino]ethyl}amino)-1,2,5-oxadiazole-3-carboximidamide

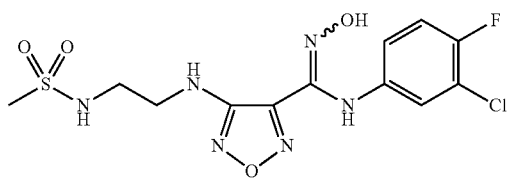 [SMILES: CS(=O)(=O)NCCNc1nonc1C(=NO)Nc1ccc(F)c(Cl)c1]

The title compound was prepared according to the procedure of Example 17 step E, using N'-hydroxy-4-({2-[(methylsulfonyl)amino]ethyl}amino)-1,2,5-oxadiazole-3-carboximidamide and 3-chloro-4-fluoroaniline [Aldrich, product #228583] as the starting materials. LCMS for $C_{12}H_{15}ClFN_6O_4S$ (M+H)$^+$: m/z=393.0. $^1$H NMR (400 MHz, DMSO-d$_6$): δ 11.50 (s, 1H), 8.91 (s, 1H), 7.19 (m, 2H), 6.96 (dd, J=6.7, 2.5 Hz, 1H), 6.71 (m, 1H), 6.26 (t, J=6.4 Hz, 1H), 3.32 (m, 2H), 3.13 (q, J=5.8 Hz, 2H), 2.89 (s, 3H).

Example 7

4-({3-[(Aminosulfonyl)amino]propyl}amino)-N-(3-chloro-4-fluorophenyl)-N'-hydroxy-1,2,5-oxadiazole-3-carboximidamide

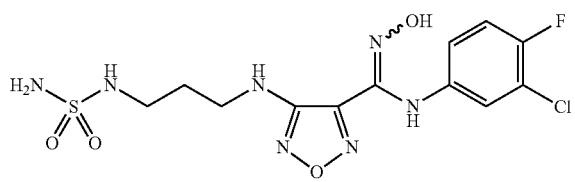 [SMILES: NS(=O)(=O)NCCCNc1nonc1C(=NO)Nc1ccc(F)c(Cl)c1]

Step A: 3-[(Diphenylmethylene)amino]propan-1-ol

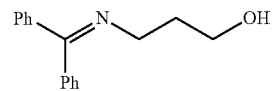 [SMILES: OCCCN=C(c1ccccc1)c1ccccc1]

A solution of 3-amino-1-propanol [Aldrich product # A76400] (2.0 mL, 26 mmol) in dichloromethane (79 mL) was treated with benzophenone imine (4.4 mL, 26 mmol) and stirred at 25° C. for 16 h. The reaction mixture was filtered and the filtrate was concentrated to give the desired product (6.3 g, quantitative) as an oil. This material was used without further purification. LCMS for $C_{16}H_{18}NO$ (M+H)$^+$: m/z=240.2.

Step B: 3-{4-[(3-Aminopropyl)amino]-1,2,5-oxadiazol-3-yl}-4-(3-chloro-4-fluorophenyl)-1,2,4-oxadiazol-5(4H)-one trifluoroacetate

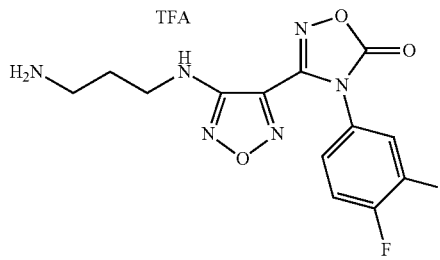

A solution of 3-[(diphenylmethylene)amino]propan-1-ol (80 mg, 0.33 mmol) and triphenylphosphine (93 mg, 0.36 mmol) in tetrahydrofuran (1 mL) at 0° C. was treated with diisopropyl azodicarboxylate (75 μL, 0.38 mmol) dropwise. The reaction mixture was stirred at 0° C. for 15 min, treated with a solution of N-{4-[4-(3-chloro-4-fluorophenyl)-5-oxo-4,5-dihydro-1,2,4-oxadiazol-3-yl]-1,2,5-oxadiazol-3-yl}-2,2,2-trifluoroacetamide (100 mg, 0.25 mmol) in tetrahydrofuran (0.5 mL), and stirred at 25° C. for 16 h. The reaction mixture was treated with trifluoroacetic acid (1 mL), stirred at 25° C. for 3 h, and concentrated to a crude residue. This material was purified by preparative LCMS to give the desired product (18 mg, 15%). LCMS for $C_{13}H_{13}ClFN_6O_3$ (M+H)$^+$: m/z=355.1

Step C: 4-({3-[(Aminosulfonyl)amino]propyl}amino)-N-(3-chloro-4-fluorophenyl)-N'-hydroxy-1,2,5-oxadiazole-3-carboximidamide The desired compound was prepared according to the procedure of Example 15, step G, using 3-{4-[(3-aminopropyl)amino]-1,2,5-oxadiazol-3-yl}-4-(3-chloro-4-fluorophenyl)-1,2,4-oxadiazol-5(4H)-one trifluoroacetate as the starting material in 34% yield. LCMS for $C_{12}H_{16}ClFN_7O_4S$ (M+H)$^+$: m/z=408.1. $^1$H NMR (400 MHz, DMSO-d$_6$): δ 8.90 (s, 1H), 7.20 (dd, J=9.2, 9.0 Hz, 1H), 6.96 (dd, J=6.4, 2.7 Hz, 1H), 6.72-6.69 (m, 1H), 6.55 (t, J=6.0 Hz, 1H), 6.51 (s, 2H), 6.16 (t, J=5.9 Hz, 1H), 3.28-3.21 (m, 2H), 2.93-2.87 (m, 2H), 1.76-1.72 (m, 2H).

Example 8

N-(3-Chloro-4-fluorophenyl)-N'-hydroxy-4-({3-[(methylsulfonyl)amino]propyl}amino)-1,2,5-oxadiazole-3-carboximidamide

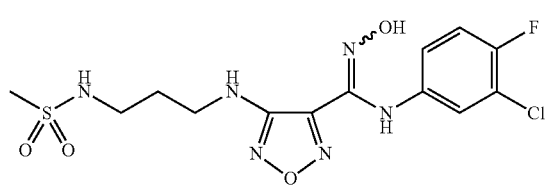 [SMILES: CS(=O)(=O)NCCCNc1nonc1C(=NO)Nc1ccc(F)c(Cl)c1]

The title compound was prepared according to the procedure of Example 4, step E, using N'-hydroxy-4-({3-[(methylsulfonyl)amino]propyl}amino)-1,2,5-oxadiazole-3-carboximidamide [made according to Example 4, steps A through D] and 3-chloro-4-fluoroaniline [Aldrich, product #228583] as the starting materials in 10% yield. LCMS for $C_{13}H_{17}ClFN_6O_4S$ (M+H)$^+$: m/z=407.1. $^1$H NMR (400 MHz, CD$_3$OD): δ 7.06 (t, J=8.9 Hz, 1H), 6.98 (m, 1H), 6.80 (m, 1H), 3.73 (m, 2H), 3.28 (m, 2H), 2.94 (s, 3H), 1.28 (m, 2H).

Example 9

4-({2-[(Aminosulfonyl)amino]ethyl}amino)-N-[4-fluoro-3-(trifluoromethyl)phenyl]-N'-hydroxy-1,2,5-oxadiazole-3-carboximidamide

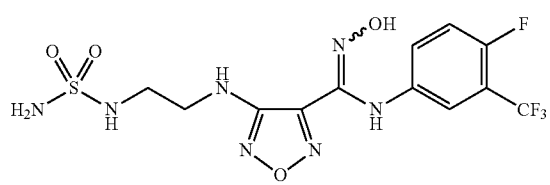 [SMILES: NS(=O)(=O)NCCNc1nonc1C(=NO)Nc1ccc(F)c(C(F)(F)F)c1]

Step A: N-[4-Fluoro-3-(trifluoromethyl)phenyl]-N'-hydroxy-4-[(2-methoxyethyl)amino]-1,2,5-oxadiazole-3-carboximidamide

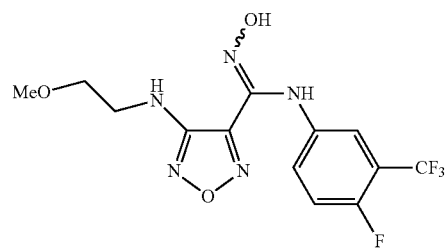 [SMILES: COCCNc1nonc1C(=NO)Nc1ccc(F)c(C(F)(F)F)c1]

The desired compound was prepared according to the procedure of Example 13, step A, using N-hydroxy-4-[(2-methoxyethyl)amino]-1,2,5-oxadiazole-3-carboximidoyl chloride [made according to Example 1, steps A through E] and 3-trifluoromethyl-4-fluoroaniline [Aldrich, product #217778] as the starting materials in quantitative yield. LCMS for $C_{13}H_{14}F_4N_5O_3$ (M+H)$^+$: m/z=364.0. $^1$H NMR (400 MHz, CD$_3$OD): δ 7.15 (m, 2H), 7.08 (m, 1H), 3.60 (t, J=5.3 Hz, 2H), 3.46 (t, J=5.3 Hz, 2H), 3.38 (s, 3H).

Step B: 4-[4-Fluoro-3-(trifluoromethyl)phenyl]-3-{4-[(2-methoxyethyl)amino]-1,2,5-oxadiazol-3-yl}-1,2,4-oxadiazol-5(4H)-one

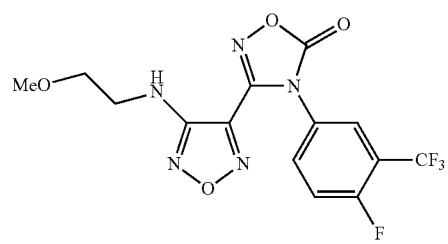

The desired compound was prepared according to the procedure of Example 13, step B, using N-[4-fluoro-3-(trifluoromethyl)phenyl]-N'-hydroxy-4-[(2-methoxyethyl)amino]-1,2,5-oxadiazole-3-carboximidamide as the starting material in 79% yield. LCMS for $C_{14}H_{12}F_4N_5O_4$ (M+H)$^+$: m/z=390.0. $^1$H NMR (400 MHz, DMSO-d$_6$): δ 8.20 (dd, J=6.3, 2.4 Hz, 1H), 8.03 (m, 1H), 7.76 (t, J=9.5 Hz, 1H), 6.41 (t, J=5.7 Hz, 1H), 3.49 (t, J=5.5 Hz, 2H), 3.39 (q, J=5.7 Hz, 2H), 3.25 (s, 3H).

Step C: 4-[4-Fluoro-3-(trifluoromethyl)phenyl]-3-{4-[(2-hydroxyethyl)amino]-1,2,5-oxadiazol-3-yl}-1,2,4-oxadiazol-5(4H)-one

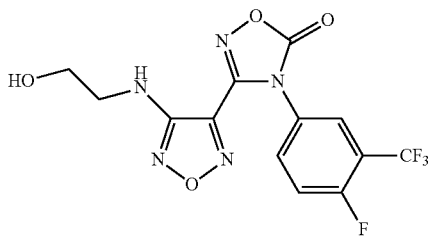 [SMILES: O=c1onc(-c2nonc2NCCO)n1-c1ccc(F)c(C(F)(F)F)c1]

The desired compound was prepared according to the procedure of Example 13, step C, using 4-[4-fluoro-3-(trifluoromethyl)phenyl]-3-{4-[(2-methoxyethyl)amino]-1,2,5-oxadiazol-3-yl}-1,2,4-oxadiazol-5(4H)-one as the starting material in 99% yield. LCMS for $C_{13}H_{10}F_4N_5O_4$ (M+H)$^+$: m/z=376.0. $^1$H NMR (400 MHz, DMSO-d$_6$): δ 8.22 (m, 1H), 8.05 (m, 1H), 7.76 (t, J=9.9 Hz, 1H), 6.34 (t, J=5.7 Hz, 1H), 4.87 (t, J=5.2 Hz, 1H), 3.56 (q, J=5.5 Hz, 2H), 3.29 (q, J=5.7 Hz, 2H).

Step D: 2-[(4-{4-[4-Fluoro-3-(trifluoromethyl)phenyl]-5-oxo-4,5-dihydro-1,2,4-oxadiazol-3-yl}-1,2,5-oxadiazol-3-yl)-amino]ethyl methanesulfonate

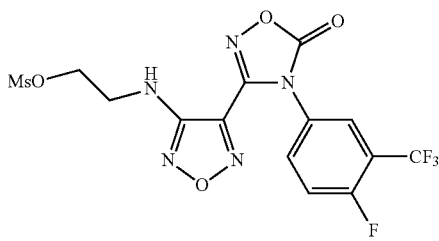

The desired compound was prepared according to the procedure of Example 13, step D, using 4-[4-fluoro-3-(trifluoromethyl)phenyl]-3-{4-[(2-hydroxyethyl)amino]-1,2,5-oxadiazol-3-yl}-1,2,4-oxadiazol-5(4H)-one as the starting material in 95% yield. LCMS for $C_{14}H_{12}F_4N_5O_6S$ (M+H)$^+$: m/z=454.0. $^1$H NMR (400 MHz, DMSO-d$_6$): δ 8.23 (dd, J=6.5, 2.5 Hz, 1H), 8.06 (m, 1H), 7.76 (t, J=9.6 Hz, 1H), 6.76 (t, J=5.8 Hz, 1H), 4.37 (t, J=5.4 Hz, 2H), 3.60 (q, J=5.5 Hz, 2H), 3.17 (s, 3H).

Step E: 3-{4-[(2-Azidoethyl)amino]-1,2,5-oxadiazol-3-yl}-4-[4-fluoro-3-(trifluoromethyl)phenyl]-1,2,4-oxadiazol-5(4H)-one

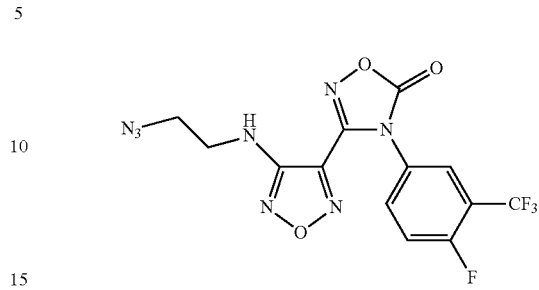

The desired compound was prepared according to the procedure of Example 13, step E, using 2-[(4-{4-[4-fluoro-3-(trifluoromethyl)phenyl]-5-oxo-4,5-dihydro-1,2,4-oxadiazol-3-yl}-1,2,5-oxadiazol-3-yl)amino]ethyl methanesulfonate as the starting material in 100% yield. LCMS for $C_{13}H_9F_4N_6O_3$ (M−N$_2$+H)$^+$: m/z=372.8. $^1$H NMR (400 MHz, DMSO-d$_6$): δ 8.22 (dd, J=6.2, 2.4 Hz, 1H), 8.05 (m, 1H), 7.76 (t, J=9.6 Hz, 1H), 6.75 (t, J=5.9 Hz, 1H), 3.53 (t, J=5.9 Hz, 2H), 3.45 (q, J=5.6 Hz, 2H).

Step F: 3-{4-[(2-Aminoethyl)amino]-1,2,5-oxadiazol-3-yl}-4-[4-fluoro-3-(trifluoromethyl)phenyl]-1,2,4-oxadiazol-5(4H)-one hydroiodide

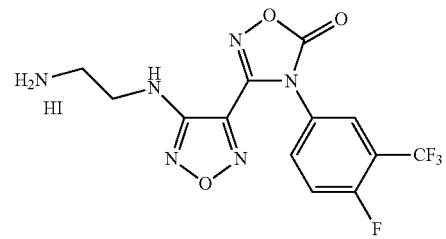

The desired compound was prepared according to the procedure of Example 13, step F, using 3-{4-[(2-azidoethyl)amino]-1,2,5-oxadiazol-3-yl}-4-[4-fluoro-3-(trifluoromethyl)phenyl]-1,2,4-oxadiazol-5(4H)-one as the starting material in 80% yield. LCMS for $C_{13}H_{11}F_4N_6O_3$ (M+H)$^+$: m/z=375.0. $^1$H NMR (400 MHz, DMSO-d$_6$): δ 8.20 (dd, J=6.2, 2.4 Hz, 1H), 8.03 (m, 1H), 7.74 (t, J=9.8 Hz, 1H), 7.10 (br s, 0.4H), 6.68 (t, J=5.5 Hz, 1H), 3.42 (q, J=5.8 Hz, 2H), 2.95 (t, J=6.5 Hz, 2H).

Step G: 4-({2-[(Aminosulfonyl)amino]ethyl}amino)-N-[4-fluoro-3-(trifluoromethyl)phenyl]-N'-hydroxy-1,2,5-oxadiazole-3-carboximidamide The title compound was prepared according to the procedure of Example 13, step G, using 3-{4-[(2-aminoethyl)amino]-1,2,5-oxadiazol-3-yl}-4-[4-fluoro-3-(trifluoromethyl)phenyl]-1,2,4-oxadiazol-5(4H)-one hydroiodide as the starting material in 55% yield. LCMS for $C_{12}H_{14}F_4N_7O_4S$ (M+H)$^+$: m/z=428.0. $^1$H NMR (400 MHz, DMSO-d$_6$): δ 11.60 (s, 1H), 9.06 (s, 1H), 7.30 (t, J=10.1 Hz, 1H), 7.14 (dd, J=6.1, 2.7 Hz, 1H), 7.03 (m, 1H), 6.71 (t, J=5.3 Hz, 1H), 6.58 (s, 2H), 6.23 (t, J=6.2 Hz, 1H), 3.36 (q, J=6.5 Hz, 2H), 3.08 (m, 2H).

Example 10

N-[4-Fluoro-3-(trifluoromethyl)phenyl]-N'-hydroxy-4-({2-[(methylsulfonyl)amino]ethyl}amino)-1,2,5-oxadiazole-3-carboximidamide

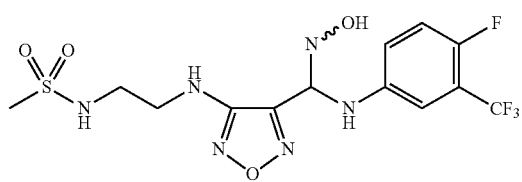 [SMILES: CS(=O)(=O)NCCNc1nonc1C(NO)Nc1ccc(F)c(C(F)(F)F)c1]

The title compound was prepared according to the procedure of Example 17 step E, using N'-hydroxy-4-({2-[(methylsulfonyl)amino]ethyl}amino)-1,2,5-oxadiazole-3-carboximidamide and 3-trifluoromethyl-4-fluoroaniline [Aldrich, product #217778] as the starting materials. LCMS for $C_{13}H_{15}F_4N_6O_4S$ (M+H)$^+$: m/z=427.0. $^1$H NMR (400 MHz, DMSO-d$_6$): δ 11.60 (s, 1H), 9.07 (s, 1H), 7.30 (t, J=10.1 Hz, 1H), 7.18 (t, J=6.0 Hz, 1H), 7.13 (dd, J=6.0, 2.7 Hz, 1H), 7.03 (m, 1H), 6.27 (t, J=6.3 Hz, 1H), 3.32 (m, 2H), 3.13 (q, J=6.0 Hz, 2H), 2.89 (s, 3H).

Example 11

4-({3-[(Aminosulfonyl)amino]propyl}amino)-N-[4-fluoro-3-(trifluoromethyl)phenyl]-N'-hydroxy-1,2,5-oxadiazole-3-carboximidamide

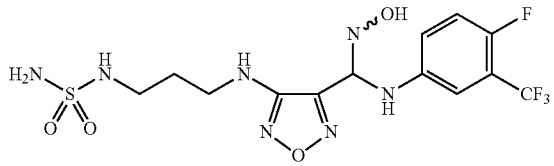 [SMILES: NS(=O)(=O)NCCCNc1nonc1C(NO)Nc1ccc(F)c(C(F)(F)F)c1]

Step A: 4-Amino-N'-hydroxy-N-(3-methoxypropyl)-1,2,5-oxadiazole-3-carboximidamide

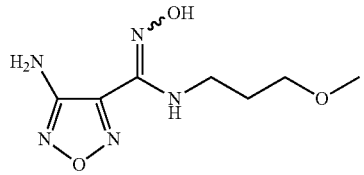

The desired compound was prepared according to the procedure of Example 1, step C, using 3-methoxy-1-propanamine as the starting material in 93% yield. LCMS for $C_7H_{14}N_5O_3$ (M+H)$^+$: m/z=216.1.

Step B: N'-Hydroxy-4-[(3-methoxypropyl)amino]-1,2,5-oxadiazole-3-carboximidamide

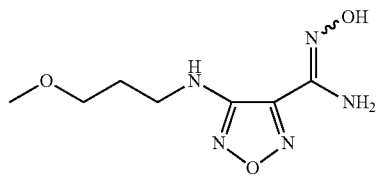

The desired compound was prepared according to the procedure of Example 1, step D, using 4-amino-N'-hydroxy-N-(3-methoxypropyl)-1,2,5-oxadiazole-3-carboximidamide as the starting material in 72% yield. LCMS for $C_7H_{14}N_5O_3$ (M+H)$^+$: m/z=216.1. $^1$H NMR (300 MHz, DMSO-d$_6$): δ 10.4 (s, 1H), 6.21-6.13 (m, 3H), 3.37 (t, J=6.1 Hz, 2H), 3.28-3.21 (m, 5H), 1.82-1.74 (m, 2H).

Step C: N-Hydroxy-4-[(3-methoxypropyl)amino]-1,2,5-oxadiazole-3-carboximidoyl chloride

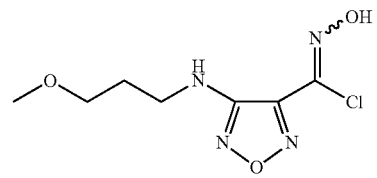

The desired compound was prepared according to the procedure of Example 1, step E, using N'-Hydroxy-4-[(3-methoxypropyl)amino]-1,2,5-oxadiazole-3-carboximidamide as the starting material in quantitative yield. LCMS for $C_7H_{12}ClN_4O_3$ (M+H)$^+$: m/z=235.1.

Step D: N-[4-Fluoro-3-(trifluoromethyl)phenyl]-N'-hydroxy-4-[(3-methoxypropyl)amino]-1,2,5-oxadiazole-3-carboximidamide

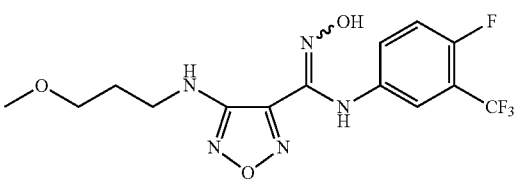 [SMILES: COCCCNc1nonc1C(=NO)Nc1ccc(F)c(C(F)(F)F)c1]

The desired compound was prepared according to the procedure of Example 1, step F, using N-hydroxy-4-[(3-methoxypropyl)amino]-1,2,5-oxadiazole-3-carboximidoyl chloride and 4-fluoro-3-(trifluoromethyl)benzeneamine as the starting materials in 87% yield. LCMS for $C_{14}H_{16}F_4N_5O_3$ (M+H)$^+$: m/z=378.1. $^1$H NMR (400 MHz, DMSO-d$_6$): δ 11.5 (s, 1H), 9.05 (s, 1H), 7.30 (dd, J=10.0, 9.6 Hz, 1H), 7.13-7.11 (m, 1H), 7.05-7.00 (m, 1H), 6.22 (t, J=5.7 Hz, 1H), 3.35-3.32 (m, 2H), 3.25-3.19 (m, 5H), 1.79-1.72 (m, 2H).

Step E: 4-[4-Fluoro-3-(trifluoromethyl)phenyl]-3-{4-[(3-methoxypropyl)amino]-1,2,5-oxadiazol-3-yl}-1,2,4-oxadiazol-5(4H)-one

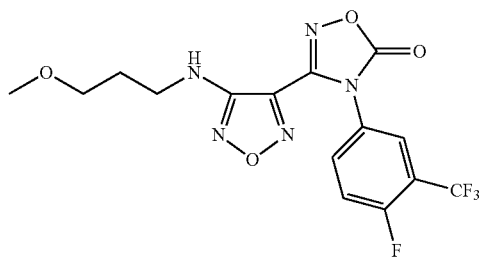 [SMILES: COCCCNc1nonc1-c1noc(=O)n1-c1ccc(F)c(C(F)(F)F)c1]

The desired compound was prepared according to the procedure of Example 1, step G, using N-[4-fluoro-3-(trifluoromethyl)phenyl]-N'-hydroxy-4-[(3-methoxypropyl)amino]-1,2,5-oxadiazole-3-carboximidamide as the starting material in quantitative yield. LCMS for $C_{15}H_4F_4N_5O_4$ $(M+H)^+$: m/z=404.0.

Step F: 4-[4-Fluoro-3-(trifluoromethyl)phenyl]-3-{4-[(3-hydroxypropyl)amino]-1,2,5-oxadiazol-3-yl}-1,2,4-oxadiazol-5(4H)-one

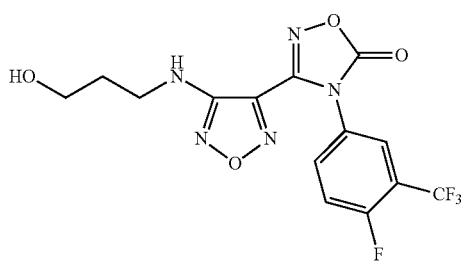 [SMILES: O=c1onc(-c2nonc2NCCCO)n1-c1ccc(F)c(C(F)(F)F)c1]

The desired compound was prepared according to the procedure of Example 3, step D, using 4-[4-fluoro-3-(trifluoromethyl)phenyl]-3-{4-[(3-methoxypropyl)amino]-1,2,5-oxadiazol-3-yl}-1,2,4-oxadiazol-5(4H)-one as the starting material in 97% yield. LCMS for $C_{14}H_{12}F_4N_5O_4$ $(M+H)^+$: m/z=390.0. $^1$H NMR (300 MHz, DMSO-$d_6$): δ 8.20 (dd, J=6.4, 2.6 Hz, 1H), 8.06-8.01 (m, 1H), 7.75 (dd, J=10.0, 9.4 Hz, 1H), 6.53 (t, J=5.7 Hz, 1H), 4.59 (t, J=5.0 Hz, 1H), 3.51-3.42 (m, 2H), 3.32-3.26 (m, 2H), 1.73-1.68 (m, 2H).

Step G: 3-{4-[(3-Azidopropyl)amino]-1,2,5-oxadiazol-3-yl}-4-[4-fluoro-3-(trifluoromethyl)phenyl]-1,2,4-oxadiazol-5(4H)-one

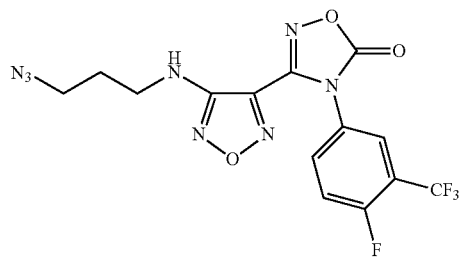 [SMILES: [N-]=[N+]=NCCCNc1nonc1-c1noc(=O)n1-c1ccc(F)c(C(F)(F)F)c1]

The desired compound was prepared according to the procedure of Example 3, step E, using 4-[4-fluoro-3-(trifluoromethyl)phenyl]-3-{4-[(3-hydroxypropyl)amino]-1,2,5-oxadiazol-3-yl}-1,2,4-oxadiazol-5(4H)-one as the starting material in quantitative yield. LCMS for $C_{14}H_{10}F_4N_8O_3Na$ $(M+Na)^+$: m/z=437.0.

Step H: 3-{4-[(3-Aminopropyl)amino]-1,2,5-oxadiazol-3-yl}-4-[4-fluoro-3-(trifluoromethyl)phenyl]-1,2,4-oxadiazol-5(4H)-one hydroiodide

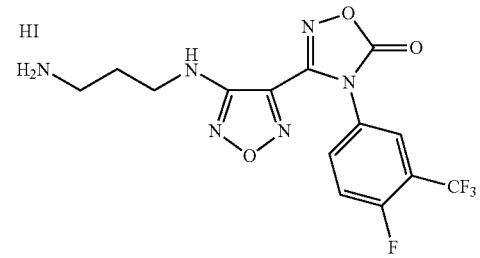

The desired compound was prepared according to the procedure of Example 3, step F, using 3-{4-[(3-azidopropyl)amino]-1,2,5-oxadiazol-3-yl}-4-[4-fluoro-3-(trifluoromethyl)phenyl]-1,2,4-oxadiazol-5(4H)-one as the starting material in 81% yield. LCMS for $C_{14}H_{13}F_4N_6O_3$ $(M+H)^+$: m/z=389.1. $^1$H NMR (300 MHz, DMSO-$d_6$): δ 8.18 (dd, J=6.4, 2.3 Hz, 1H), 8.06-8.01 (m, 1H), 7.72 (dd, J=9.7, 9.4 Hz, 1H), 7.34 (br s, 2H), 6.71 (br s, 1H), 2.78-2.73 (m, 2H), 1.85-1.75 (m, 2H).

Step I: 4-({3-[(Aminosulfonyl)amino]propyl}amino)-N-[4-fluoro-3-(trifluoromethyl)phenyl]-N'-hydroxy-1,2,5-oxadiazole-3-carboximidamide The desired compound was prepared according to the procedure of Example 15, step G, using 3-{4-[(3-aminopropyl)amino]-1,2,5-oxadiazol-3-yl}-4-[4-fluoro-3-(trifluoromethyl)phenyl]-1,2,4-oxadiazol-5(4H)-one hydroiodide as the starting material in 60% yield. LCMS for $C_{13}H_{16}F_4N_7O_4S$ $(M+H)^+$: m/z=442.0. $^1$H NMR (300 MHz, DMSO-$d_6$): δ 11.6 (s, 1H), 9.08 (s, 1H), 7.31 (dd, J=10.0, 9.4 Hz, 1H), 7.13 (dd, J=6.4, 2.9 Hz, 1H), 7.05-6.99 (m, 1H), 6.58 (t, J=6.0 Hz, 1H), 6.52 (s, 2H), 6.17 (t, J=5.9 Hz, 1H), 3.28-3.21 (m, 2H), 2.94-2.87 (m, 2H), 1.79-1.72 (m, 2H).

Example 12

N-[4-Fluoro-3-(trifluoromethyl)phenyl]-N'-hydroxy-4-({3-[(methylsulfonyl)amino]propyl}amino)-1,2,5-oxadiazole-3-carboximidamide

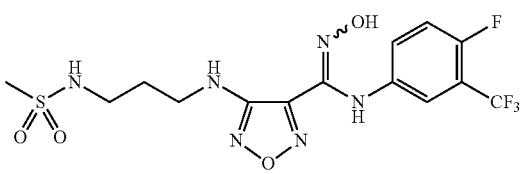 [SMILES: CS(=O)(=O)NCCCNc1nonc1C(=NO)Nc1ccc(F)c(C(F)(F)F)c1]

The desired compound was prepared according to the procedure of Example 16 using 3-{4-[(3-aminopropyl)amino]-1,2,5-oxadiazol-3-yl}-4-[4-fluoro-3-(trifluoromethyl)phenyl]-1,2,4-oxadiazol-5(4H)-one hydroiodide as the starting material in 70% yield. LCMS for $C_{14}H_{17}F_4N_6O_4S$ (M+H)$^+$: m/z=441.1. $^1$H NMR (400 MHz, DMSO-d$_6$): δ 11.6 (s, 1H), 9.07 (s, 1H), 7.30 (dd, J=10.0, 9.6 Hz, 1H), 7.13 (dd, J=6.2, 2.5 Hz, 1H), 7.05-7.02 (m, 2H), 6.19 (t, J=5.8 Hz, 1H), 3.27-3.21 (m, 2H), 2.99-2.94 (m, 2H), 2.87 (s, 3H), 1.76-1.72 (m, 2H).

Example 13

4-({2-[(Aminosulfonyl)amino]ethyl}amino)-N'-hydroxy-N-[3-(trifluoromethyl)phenyl]-1,2,5-oxadiazole-3-carboximidamide

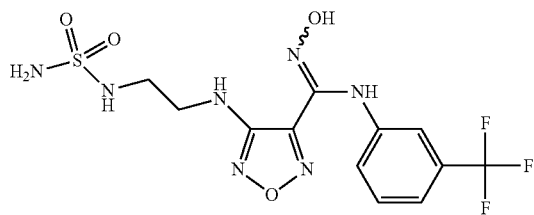 [SMILES: NS(=O)(=O)NCCNc1nonc1C(=NO)Nc1cccc(C(F)(F)F)c1]

Step A: N'-hydroxy-4-[(2-methoxyethyl)amino]-N-[3-(trifluoromethyl)phenyl]-1,2,5-oxadiazole-3-carboximidamide

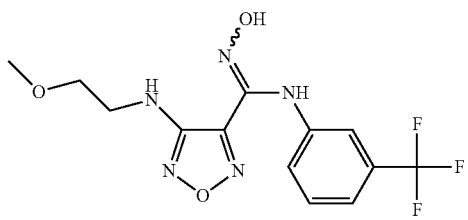 [SMILES: COCCNc1nonc1C(=NO)Nc1cccc(C(F)(F)F)c1]

N-Hydroxy-4-[(2-methoxyethyl)amino]-1,2,5-oxadiazole-3-carboximidoyl chloride (1.3 g, 5.0 mmol) [made according to Example 1, steps A through E] was stirred in water (10 mL) and warmed to 60° C. for 5 minutes. 3-(trifluoromethyl)aniline [Aldrich, product # A41801] (880 mg, 5.5 mmol) was added in one portion and the reaction stirred for 15 minutes. While remaining at 60° C., a solution of sodium bicarbonate (630 mg, 7.5 mmol) in water (10 mL) was added dropwise over 5 minutes. The reaction was stirred at 60° C. for an additional 50 minutes, and then allowed to cool to room temperature. Ethyl acetate (20 mL) and brine (30 mL) were added to the flask and the organic layer was collected. The aqueous layer was extracted with ethyl acetate (2×20 mL) and the combined organics were dried over sodium sulfate. The solvent was removed in vacuo to give the desired product as an orange solid (1.4 g, 80%). LCMS calculated for $C_{13}H_{15}F_3N_5O_3$ (M+H)$^+$: m/z=346.1. $^1$H NMR (400 MHz, CD$_3$OD): δ 7.36 (t, J=8.2 Hz, 1H), 7.23 (d, J=7.6 Hz, 1H), 7.09 (s, 1H), 7.02 (d, J=8.2 Hz, 1H), 3.60 (t, J=5.2 Hz, 2H), 3.46 (t, J=5.2 Hz, 2H), 3.38 (s, 3H).

Step B: 3-{4-[(2-Methoxyethyl)amino]-1,2,5-oxadiazol-3-yl}-4-[3-(trifluoromethyl)phenyl]-1,2,4-oxadiazol-5(4H)-one

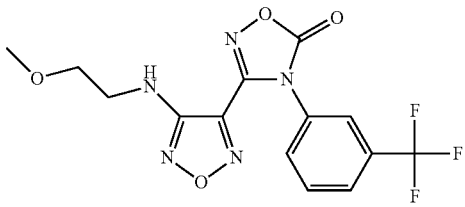 [SMILES: COCCNc1nonc1-c1noc(=O)n1-c1cccc(C(F)(F)F)c1]

N'-Hydroxy-4-[(2-methoxyethyl)amino]-N-[3-(trifluoromethyl)phenyl]-1,2,5-oxadiazole-3-carboximidamide (1.4 g, 3.80 mmol) and 1,1'-carbonyldiimidazole (1.16 g, 7.16 mmol) were dissolved in ethyl acetate (20 mL). The reaction mixture was heated at 70° C. for 40 minutes. Additional 1,1'-carbonyldiimidazole (0.26 g, 1.16 mmol) was added. After stirring at 70° C. for another 50 minutes, the reaction was allowed to cool to room temperature. Ethyl acetate (20 mL) was added and the crude reaction was washed with 1 N HCl in water (2×20 mL). Brine was added to aid in the separation of the first wash. The organic layer was dried over sodium sulfate and concentrated in vacuo. Purification by flash chromatography on silica gel with an eluent of ethyl acetate in hexanes gave the desired product (1.3 g, 90%). LCMS calculated for $C_{14}H_{13}F_3N_5O_4$ (M+H)$^+$: m/z=372.0. $^1$H NMR (400 MHz, DMSO-d$_6$): δ 8.07 (s, 1H), 7.92 (m, 2H), 7.79 (t, J=8.1 Hz, 1H), 6.42 (t, J=6.0 Hz, 1H), 3.47 (t, J=5.8 Hz, 2H), 3.38 (q, J=5.0 Hz, 2H), 3.24 (s, 3H).

Step C: 3-{4-[(2-Hydroxyethyl)amino]-1,2,5-oxadiazol-3-yl}-4-[3-(trifluoromethyl)phenyl]-1,2,4-oxadiazol-5(4H)-one

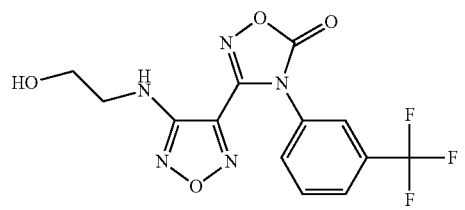 [SMILES: O=c1onc(-c2nonc2NCCO)n1-c1cccc(C(F)(F)F)c1]

In a round bottom flask under nitrogen atmosphere, 3-{4-[(2-methoxyethyl)amino]-1,2,5-oxadiazol-3-yl}-4-[3-(trifluoromethyl)phenyl]-1,2,4-oxadiazol-5(4H)-one (1.3 g, 3.6 mmol) was stirred in dichloromethane (11 mL). The temperature was brought to −78° C. and a solution of 1.0 M boron tribromide in dichloromethane (7.9 mL, 7.9 mmol) was added dropwise over 15 minutes. The reaction was warmed to room temperature over 45 minutes and continued to stir at room temperature for an additional 45 minutes. The reaction was cooled to 0° C. and a saturated solution of sodium bicarbonate in water (25 mL) was added dropwise over 15 minutes. After warming to room temperature, ethyl acetate (10 mL) and water (10 mL) were added to the flask. The organic layer was collected and the aqueous layer was extracted with ethyl acetate (2×20 mL). After drying the combined organic layers over sodium sulfate, the solvent was removed in vacuo to give the desired product (1.0 g, 81%). LCMS calculated for $C_{13}H_{11}F_3N_5O_4$ (M+H)$^+$: m/z=358.0. $^1$H NMR (400 MHz, DMSO-d$_6$): δ 8.08 (s, 1H), 7.93 (t, J=8.2 Hz, 2H), 7.79 (t, J=8.2 Hz, 1H), 6.35 (t, J=5.7 Hz, 1H), 4.86 (br s, 1H), 3.55 (t, J=6.0 Hz, 2H), 3.28 (m, 2H).

Step D: 2-[(4-{5-Oxo-4-[3-(trifluoromethyl)phenyl]-4,5-dihydro-1,2,4-oxadiazol-3-yl}-1,2,5-oxadiazol-3-yl)amino]ethyl methanesulfonate

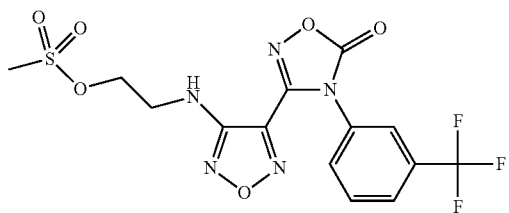 [SMILES: CS(=O)(=O)OCCNc1nonc1-c1noc(=O)n1-c1cccc(C(F)(F)F)c1]

To a solution of 3-{4-[(2-hydroxyethyl)amino]-1,2,5-oxadiazol-3-yl}-4-[3-(trifluoromethyl)phenyl]-1,2,4-oxadiazol-5(4H)-one (1.0 g, 2.9 mmol) in ethyl acetate (8.5 mL) was added methanesulfonyl chloride (0.29 mL, 3.7 mmol) in one portion. The reaction was stirred for 5 minutes and triethylamine (0.52 mL, 3.7 mmol) was added, also in one portion. After stirring for an additional 10 minutes, the reaction was quenched with the addition of water (5 mL). The product was extracted with ethyl acetate (2×5 mL), dried over sodium sulfate and concentrated in vacuo to give the desired product (1.2 g, 99%). LCMS calculated for $C_{14}H_{13}F_3N_5O_6S$ (M+H)$^+$: m/z=436.0. $^1$H NMR (400 MHz, DMSO-d$_6$): δ 8.10 (s, 1H), 7.92 (m, 2H), 7.80 (t, J=8.2 Hz, 1H), 6.77 (t, J=5.9 Hz, 1H), 4.36 (t, J=5.5 Hz, 2H), 3.58 (m, 2H), 3.17 (s, 3H).

Step E: 3-{-4-[(2-Azidoethyl)amino]-1,2,5-oxadiazol-3-yl}-4-[3-(trifluoromethyl)phenyl]-1,2,4-oxadiazol-5(4H)-one

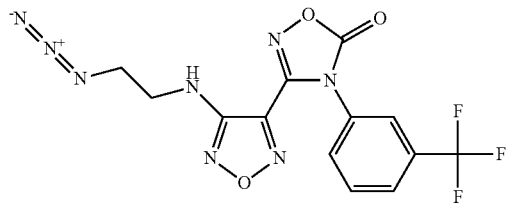

2-[(4-{5-Oxo-4-[3-(trifluoromethyl)phenyl]-4,5-dihydro-1,2,4-oxadiazol-3-yl}-1,2,5-oxadiazol-3-yl)amino]ethyl methanesulfonate (1.2 g, 2.9 mmol) was dissolved in N,N-dimethylformamide (2.7 mL). After sodium azide (280 mg, 4.3 mmol) was added in one portion, the temperature was brought to 65° C. and the reaction stirred for 6 hours. After cooling back to room temperature, water (10 mL) was added to quench the reaction. The product was extracted with ethyl acetate (3×10 mL) and the combined organic layers were dried over sodium sulfate. The solvent was removed in vacuo to give the desired product (1.05 g, 96%). LCMS calculated for $C_{13}H_{10}F_3N_6O_3$ (M−N$_2$+H)$^+$: m/z=355.0. $^1$H NMR (400 MHz, DMSO-d$_6$): δ 8.09 (s, 1H), 7.93 (m, 2H), 7.79 (t, J=8.2 Hz, 1H), 6.75 (t, J=5.8 Hz, 1H), 3.52 (t, J=5.7 Hz, 2H), 3.44 (q, J=5.5 Hz, 2H).

Step F: 3-{4-[(2-Aminoethyl)amino]-1,2,5-oxadiazol-3-yl}-4-[3-(trifluoromethyl)phenyl]-1,2,4-oxadiazol-5(4H)-one hydroiodide

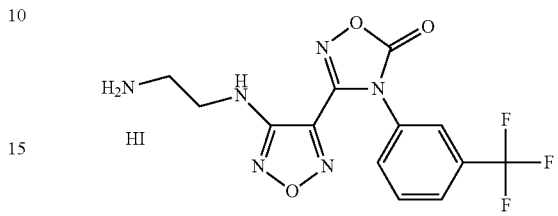

To a solution of 3-{4-[(2-azidoethyl)amino]-1,2,5-oxadiazol-3-yl}-4-[3-(trifluoromethyl)phenyl]-1,2,4-oxadiazol-5(4H)-one (1.05 g, 2.8 mmol) in methanol (12 mL) was added sodium iodide (2.5 g, 17 mmol). After stirring for 10 minutes, a solution of chlorotrimethylsilane (2.1 mL, 17 mmol) in methanol (1.41 mL) was added dropwise over 15 minutes. The reaction continued to stir for 40 minutes and then a solution of sodium thiosulfate (2.7 g, 17 mmol) in water (12.5 mL) was added in one portion. A beige solid precipitated upon addition of the sodium thiosulfate solution and it was collected by vacuum filtration. The solid was rinsed with water (2×10 mL) and was dried under vacuum overnight to give the desired product. A solid had also precipitated from the filtrate and it was collected by vacuum filtration. After washing with water (3×10 mL) in the funnel, the product was dried overnight under vacuum. The solid was slurry washed with ethyl acetate (3.8 mL) for 1 hour and recollected by filtration. After rinsing with ethyl acetate (2×2 mL) and drying overnight, additional product was obtained. In total, 760 mg of desired product (57%) was obtained as the hydroiodide salt. LCMS calculated for $C_{13}H_{12}F_3N_6O_3$ (M+H)$^+$: m/z=357.1. $^1$H NMR (400 MHz, DMSO-d$_6$): δ 8.10 (s, 1H), 7.95 (m, 2H), 7.81 (t, J=8.1 Hz, 1H), 7.68 (br s, 2H), 6.74 (t, J=6.7 Hz, 1H), 3.49 (m, 2H), 3.03 (t, J=6.7 Hz, 2H).

Step G: 4-({2-[(Aminosulfonyl)amino]ethyl}amino)-N'-hydroxy-N-[3-(trifluoromethyl)phenyl]-1,2,5-oxadiazole-3-carboximidamide To a solution of chlorosulfonyl isocyanate (9.2 μL, 0.11 mmol) in dichloromethane (0.24 mL), at 0° C. and under a nitrogen atmosphere, was added tert-butyl alcohol (10 μL, 0.11 mmol) in a dropwise fashion. The solution was allowed to stir at room temperature for 1 hour to obtain a solution of tert-butyl [chlorosulfonyl]carbamate.

In a separate flask, 3-{4-[(2-aminoethyl)amino]-1,2,5-oxadiazol-3-yl}-4-[3-(trifluoromethyl)phenyl]-1,2,4-oxadiazol-5(4H)-one hydroiodide (26 mg, 0.053 mmol) was suspended in dichloromethane (0.5 mL). A nitrogen atmosphere was established and the temperature brought to 0° C. The tert-butyl [chlorosulfonyl]carbamate solution (prepared as above) was added over 5 minutes to the stirred suspension of the amine salt. After 10 minutes, triethylamine (37 μL, 0.27 mmol) was added dropwise. The reaction mixture was stirred at room temperature for 1.5 hours. After concentrating in vacuo, the residue was treated with trifluoroacetic acid (0.5 mL, 6 mmol). This was stirred for 1 hour and the mixture was again concentrated to dryness in vacuo. The dried solids were suspended in methanol (0.5 mL) and a 2.0 N NaOH in water (0.53 mL, 1.1 mmol) was added in one portion. The reaction was heated to 45° C. and stirred for 30 minutes. After neutralization with acetic acid (60 μL, 1.1 mmol), the product was purified by preparative LCMS to give the desired product (8.5 mg, 39%). LCMS calculated for $C_{12}H_{15}F_3N_7O_4S$ (M+H)$^+$: m/z=410.0. $^1$H NMR (400 MHz, CD$_3$OD): δ 7.36 (t, J=7.8 Hz, 1H), 7.23 (d, J=7.8 Hz, 1H), 7.10 (s, 1H), 7.03 (d, J=7.8 Hz, 1H), 3.48 (m, 2H), 3.29 (m, 2H).

Example 14

N'-Hydroxy-4-({2-[(methylsulfonyl)amino]ethyl}amino)-N-[3-(trifluoromethyl)phenyl]-1,2,5-oxadiazole-3-carboximidamide

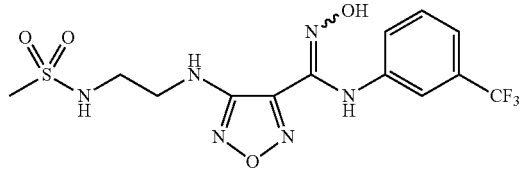 [SMILES: CS(=O)(=O)NCCNc1nonc1C(=NO)Nc1cccc(C(F)(F)F)c1]

The title compound was prepared according to the procedure of Example 17, step E, using N'-hydroxy-4-({2-[(methylsulfonyl)amino]ethyl}amino)-1,2,5-oxadiazole-3-carboximidamide and 3-trifluoromethylaniline [Aldrich, product # A41801] as the starting materials. LCMS for $C_{13}H_{16}F_3N_6O_4S$ (M+H)$^+$: m/z=409.1. $^1$H NMR (500 MHz, DMSO-d$_6$): δ 11.63 (s, 1H), 9.08 (s, 1H), 7.39 (t, J=7.6 Hz, 1H), 7.21 (m, 2H), 7.10 (s, 1H), 6.99 (d, J=8.1 Hz, 1H), 6.28 (t, J=5.4 Hz, 1H), 3.36 (q, J=5.8 Hz, 2H), 3.17 (q, J=5.8 Hz, 2H), 2.91 (s, 3H).

Example 15

4-({3-[(Aminosulfonyl)amino]propyl}amino)-N'-hydroxy-N-[3-(trifluoromethyl)phenyl]-1,2,5-oxadiazole-3-carboximidamide

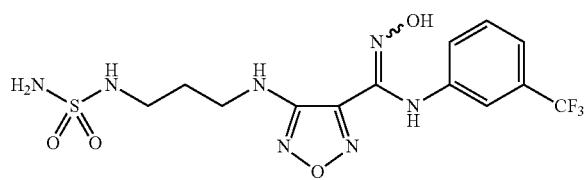 [SMILES: NS(=O)(=O)NCCCNc1nonc1C(=NO)Nc1cccc(C(F)(F)F)c1]

Step A: 3-(4-Amino-1,2,5-oxadiazol-3-yl)-4-[3-(trifluoromethyl)phenyl]-1,2,4-oxadiazol-5(4H)-one

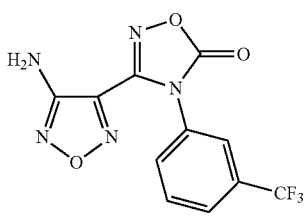 [SMILES: Nc1nonc1-c1noc(=O)n1-c1cccc(C(F)(F)F)c1]

The desired compound was prepared according to the procedure of Example 5, step A, using 4-amino-N'-hydroxy-N-[3-(trifluoromethyl)phenyl]-1,2,5-oxadiazole-3-carboximidamide [see US Pat. App. Pub. No. 2006/0258719] as the starting material in 97% yield. LCMS for $C_{11}H_7F_3N_5O_3$ (M+H)$^+$: m/z=314.1.

Step B: 2,2,2-Trifluoro-N-(4-{5-oxo-4-[3-(trifluoromethyl)phenyl]-4,5-dihydro-1,2,4-oxadiazol-3-yl}-1,2,5-oxadiazol-3-yl)acetamide

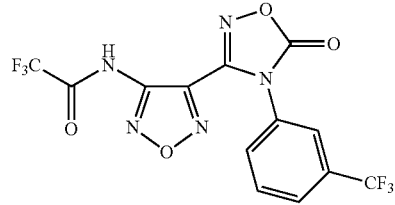 [SMILES: O=C(Nc1nonc1-c1noc(=O)n1-c1cccc(C(F)(F)F)c1)C(F)(F)F]

The desired compound was prepared according to the procedure of Example 5, step B, using 3-(4-amino-1,2,5-oxadiazol-3-yl)-4-[3-(trifluoromethyl)phenyl]-1,2,4-oxadiazol-5(4H)-one as the starting material in 90% yield. LCMS for $C_{13}H_6F_6N_5O_4$ (M+H)$^+$: m/z=410.0. $^1$H NMR (400 MHz, DMSO-d$_6$): δ 7.91-7.88 (m, 2H), 7.76-7.69 (m, 2H).

Step C: 3-{4-[(3-Methoxypropyl)amino]-1,2,5-oxadiazol-3-yl}-4-[3-(trifluoromethyl)phenyl]-1,2,4-oxadiazol-5(4H)-one

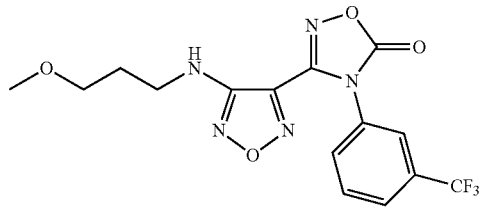 [SMILES: COCCCNc1nonc1-c1noc(=O)n1-c1cccc(C(F)(F)F)c1]

The desired compound was prepared according to the procedure of Example 3, step C, using 2,2,2-trifluoro-N-(4-{5-oxo-4-[3-(trifluoromethyl)phenyl]-4,5-dihydro-1,2,4-oxadiazol-3-yl}-1,2,5-oxadiazol-3-yl)acetamide as the starting material in 49% yield. LCMS for $C_{15}H_{15}F_3N_5O_4$ (M+H)$^+$: m/z=386.1. $^1$H NMR (300 MHz, CDCl$_3$): δ 7.83 (d, J=8.1 Hz, 1H), 7.72-7.67 (m, 2H), 7.59 (d, J=7.5 Hz, 1H), 6.08-6.04 (m, 1H), 3.57 (t, J=5.6 Hz, 2H), 3.54-3.47 (m, 2H), 3.40 (s, 3H), 2.01-1.93 (m, 2H).

Step D: 3-{4-[(3-Hydroxypropyl)amino]-1,2,5-oxadiazol-3-yl}-4-[3-(trifluoromethyl)phenyl]-1,2,4-oxadiazol-5(4H)-one

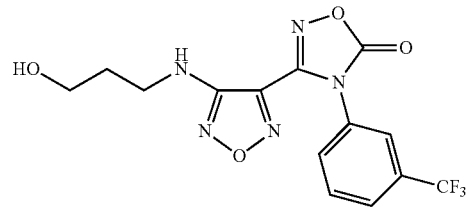 [SMILES: O=c1onc(-c2nonc2NCCCO)n1-c1cccc(C(F)(F)F)c1]

The desired compound was prepared according to the procedure of Example 3, step D, using 3-{4-[(3-methoxypropyl)amino]-1,2,5-oxadiazol-3-yl}-4-[3-(trifluoromethyl)phenyl]-1,2,4-oxadiazol-5(4H)-one as the starting material in 69% yield. LCMS for $C_{14}H_{13}F_3N_5O_4$ (M+H)$^+$: m/z=372.1. $^1$H NMR (400 MHz, DMSO-d$_6$): δ 8.07 (s, 1H), 7.95-7.90 (m, 2H), 7.79 (dd, J=7.9, 7.9 Hz, 1H), 6.55 (t, J=5.6 Hz, 1H), 4.59 (t, J=5.1 Hz, 1H), 3.47-3.42 (m, 2H), 3.30-3.25 (m, 2H), 1.72-1.65 (m, 2H).

Step E: 3-{4-[(3-Azidopropyl)amino]-1,2,5-oxadiazol-3-yl}-4-[3-(trifluoromethyl)phenyl]-1,2,4-oxadiazol-5(4H)-one

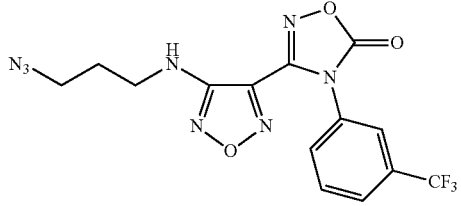 [SMILES: [N-]=[N+]=NCCCNc1nonc1-c1noc(=O)n1-c1cccc(C(F)(F)F)c1]

The desired compound was prepared according to the procedure of Example 3, step E, using 3-{4-[(3-hydroxypropyl)amino]-1,2,5-oxadiazol-3-yl}-4-[3-(trifluoromethyl)phenyl]-1,2,4-oxadiazol-5(4H)-one as the starting material in 92% yield. LCMS for $C_{14}H_{11}F_3N_8O_3Na$ (M+Na)$^+$: m/z=419.0.

Step F: 3-{4-[(3-Aminopropyl)amino]-1,2,5-oxadiazol-3-yl}-4-[3-(trifluoromethyl)phenyl]-1,2,4-oxadiazol-5(4H)-one hydroiodide

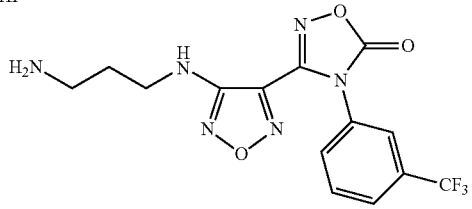

The desired compound was prepared according to the procedure of Example 3, step F, using 3-{-4-[(3-azidopropyl)amino]-1,2,5-oxadiazol-3-yl}-4-[3-(trifluoromethyl)phenyl]-1,2,4-oxadiazol-5(4H)-one as the starting material in 92% yield. LCMS for $C_{14}H_{14}F_3N_6O_3$ (M+H)$^+$: m/z=371.1. $^1$H NMR (400 MHz, DMSO-d$_6$): δ 8.09 (s, 1H), 7.96-7.92 (m, 2H), 7.80 (dd, J=8.0, 7.8 Hz, 1H), 7.53 (br s, 2H), 6.70-6.65 (m, 1H), 4.10 (br s, 1H), 3.32-3.31 (m, 2H), 2.81-2.78 (m, 2H), 1.85-1.82 (m, 2H).

Step G: 4-({3-[(Aminosulfonyl)amino]propyl}amino)-N'-hydroxy-N-[3-(trifluoromethyl)phenyl]-1,2,5-oxadiazole-3-carboximidamide A solution of 3-{4-[(3-aminopropyl)amino]-1,2,5-oxadiazol-3-yl}-4-[3-(trifluoromethyl)phenyl]-1,2,4-oxadiazol-5(4H)-one hydroiodide (1.5 g, 3.0 mmol) and sulfamide (1.7 g, 18 mmol) in pyridine (60 mL) was heated in a microwave at 130° C. for 10 min. The reaction mixture was concentrated to give the crude intermediate N-{3-[(4-{5-oxo-4-[3-(trifluoromethyl)phenyl]-4,5-dihydro-1,2,4-oxadiazol-3-yl}-1,2,5-oxadiazol-3-yl)amino]propyl}sulfamide. A solution of the crude intermediate in methanol (90 mL) was treated with 2 N NaOH (12 mL, 24 mmol) and stirred at 25° C. for 30 min. The reaction mixture was treated with 6 M HCl until the solution was acidic and extracted with ethyl acetate (250 mL). The organic layer was washed with water (100 mL) and brine (100 mL), dried over anhydrous sodium sulfate, filtered, and concentrated to give a crude residue. This material was purified by preparative LCMS to give the desired product (1.1 g, 82%) as a gummy solid. LCMS for $C_{13}H_{17}F_3N_7O_4S$ (M+H)$^+$: m/z=424.0. $^1$H NMR (400 MHz, DMSO-d$_6$): δ 11.6 (s, 1H), 9.12 (s, 1H), 7.37 (dd, J=8.0, 8.0 Hz, 1H), 7.21-7.18 (m, 1H), 7.07 (s, 1H), 6.95 (d, J=10.0 Hz, 1H), 6.52 (br s, 3H), 6.17 (t, J=6.0 Hz, 1H), 3.28-3.22 (m, 2H), 2.93-2.89 (m, 2H), 1.77-1.73 (m, 2H).

Example 16

N'-Hydroxy-4-({3-[(methylsulfonyl)amino]propyl}amino)-N-[3-(trifluoromethyl)phenyl]-1,2,5-oxadiazole-3-carboximidamide

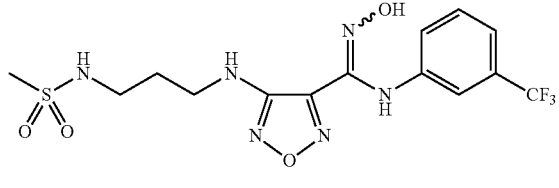 [SMILES: CS(=O)(=O)NCCCNc1nonc1C(=NO)Nc1cccc(C(F)(F)F)c1]

A solution of 3-{4-[(3-aminopropyl)amino]-1,2,5-oxadiazol-3-yl}-4-[3-(trifluoromethyl)phenyl]-1,2,4-oxadiazol-5(4H)-one hydroiodide (from Example 15, Step F; 25 mg, 50 µmol) in dichloromethane (1 mL) was treated with triethylamine (17 µL, 0.12 mmol) and methanesulfonyl chloride (6 µL, 70 µmol) and stirred at 25° C. for 2 h. The reaction mixture was concentrated to give the intermediate, N-{3-[(4-{5-oxo-4-[3-(trifluoromethyl)phenyl]-4,5-dihydro-1,2,4-oxadiazol-3-yl}-1,2,5-oxadiazol-3-yl)amino]propyl}methanesulfonamide, as a crude residue which was used without further purification. A solution of the crude intermediate in methanol (1 mL) was treated with 2 N NaOH (0.25 mL, 0.5 mmol) and stirred at 25° C. for 30 min. The reaction mixture was treated with acetic acid (50 µL, 0.9 mmol), filtered and purified by preparative LCMS to give the desired product (13 mg, 65%) as a solid. LCMS for $C_{14}H_{18}F_3N_6O_4S$ (M+H)$^+$: m/z=423.1. $^1$H NMR (400 MHz, DMSO-d$_6$): δ 11.6 (s, 1H), 9.11 (s, 1H), 7.37 (dd, J=8.0, 8.0 Hz, 1H), 7.20 (d, J=7.8 Hz, 1H), 7.07-7.01 (m, 2H), 6.96 (d, J=8.0 Hz, 1H), 6.20 (t, J=5.9 Hz, 1H), 3.27-3.22 (m, 2H), 2.99-2.94 (m, 2H), 2.87 (s, 3H), 1.78-1.71 (m, 2H).

Example 17

N-(4-Fluoro-3-methylphenyl)-N'-hydroxy-4-({2-[(methylsulfonyl)amino]ethyl}amino)-1,2,5-oxadiazole-3-carboximidamide

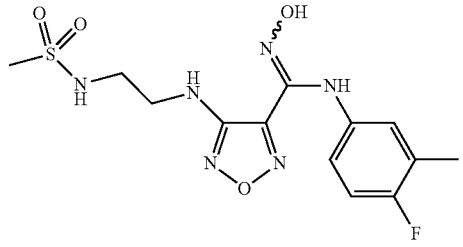

Step A: tert-Butyl {2-[(methylsulfonyl)amino]ethyl}carbamate

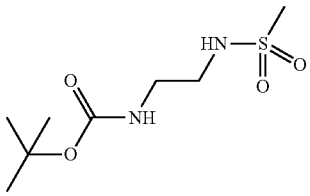

N-(2-Aminoethyl)(tert-butoxy)carboxamide (17.5 mL, 0.11 mol) [Alfa #L19947] was stirred in dichloromethane (320 mL) and triethylamine (33 mL, 0.24 mol) was added. A solution of methanesulfonyl chloride (8.5 mL, 0.11 mol) in dichloromethane (10 mL) was added. The resulting mixture was stirred for 1 hour and water (30 mL) was added. The product was extracted with dichloromethane (3×30 mL), dried over sodium sulfate and concentrated in vacuo to give the desired product (21 g, 81%). LCMS calculated for $C_3H_{11}N_2O_2S$ (M-Boc+H)$^+$: m/z=139.1.

Step B: N-(2-Aminoethyl)methanesulfonamide dihydrochloride

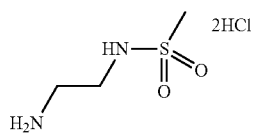

tert-Butyl {2-[(methylsulfonyl)amino]ethyl}carbamate (21 g, 88 mmol) was stirred in a solution of 4 N hydrogen chloride in 1,4-dioxane (97 mL, 388 mmol) for 30 minutes. Trituration with ethyl acetate and hexanes followed by diethyl ether and hexanes gave the desired compound as a gum (19 g, 100%). LCMS calculated for $C_3H_{11}N_2O_2S$ (M+H)$^+$: m/z=139.0.

Step C: 4-Amino-N'-hydroxy-N-{2-[(methylsulfonyl)amino]ethyl}-1,2,5-oxadiazole-3-carboximidamide

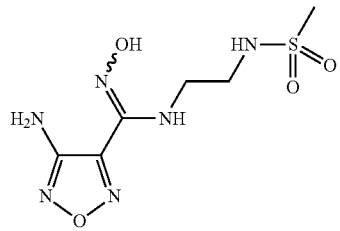 [SMILES: CS(=O)(=O)NCCNC(=NO)c1nonc1N]

4-Amino-N-hydroxy-1,2,5-oxadiazole-3-carboximidoyl chloride (9.7 g, 60 mmol) was stirred in ethanol (460 mL) and N-(2-aminoethyl)methanesulfonamide dihydrochloride (19 g, 109 mmol) was added slowly in portions and the temperature rose to 25° C. After cooling back to 0° C., triethylamine (53 mL, 380 mmol) was added dropwise over 15 minutes and the reaction was stirred for an additional 15 minutes. The solution was washed with water (300 mL) and brine (300 mL). The organic layer was dried over sodium sulfate and concentrated in vacuo to give the desired product (16 g, 100%). LCMS calculated for $C_6H_{13}N_6O_4S$ (M+H)$^+$: m/z=265.1. $^1$H NMR (400 MHz, DMSO-d$_6$): δ 10.16 (s, 1H), 9.07 (m, 1H), 7.18 (m, 1H), 6.37 (s, 2H), 3.36 (m, 2H), 3.15 (m, 2H), 2.87 (s, 3H).

Step D: N'-Hydroxy-4-({2-[(methylsulfonyl)amino]ethyl}amino)-1,2,5-oxadiazole-3-carboximidamide

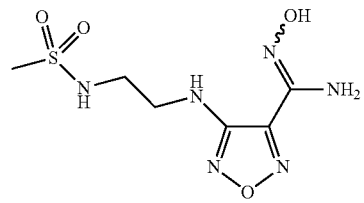 [SMILES: CS(=O)(=O)NCCNc1nonc1C(N)=NO]

4-Amino-N'-hydroxy-N-{2-[(methylsulfonyl)amino]ethyl}-1,2,5-oxadiazole-3-carboximidamide (0.47 g, 1.8 mmol) was stirred in 1,2-ethanediol (38 mL). Potassium hydroxide (600 g, 11 mmol) was added in one portion. The reaction was heated at 130° C. for 4 hours and allowed to cool to room temperature. 1 N HCl solution (60 mL) was added and the product was extracted with ethyl acetate (4×40 mL). The combined organics were dried over sodium sulfate and concentrated in vacuo to give the desired product (0.45 g, 96%). LCMS calculated for $C_6H_{12}N_6O_4S$ (M+H)$^+$: m/z=265.1. $^1$H NMR (400 MHz, DMSO-d$_6$): δ 10.49 (s, 1H), 7.18 (m, 1H), 6.20 (m, 3H), 3.36 (m, 2H), 3.15 (m, 2H), 2.87 (s, 3H).

Step E: N-(4-Fluoro-3-methylphenyl)-N'-hydroxy-4-({2-[(methylsulfonyl)amino]ethyl}amino)-1,2,5-oxadiazole-3-carboximidamide N'-Hydroxy-4-({2-[(methylsulfonyl)amino]ethyl}amino)-1,2,5-oxadiazole-3-carboximidamide (35 mg, 0.13 mmol) was stirred in 1,4-dioxane (2 mL) and 6 N hydrogen chloride solution (4 mL) was added. The solution was cooled to 0° C. and a solution of sodium nitrite (11 mg, 0.16 mmol) in water (3 mL) was slowly added. The mixture was stirred for 1 hour at 0° C. and evaporated. Dry 1,4-dioxane (2 mL) was added and the mixture evaporated two more times. A solution of 4-fluoro-3-methylaniline [Aldrich, product #559415] (25 mg, 0.20 mmol) in ethanol (2 mL) was added and the mixture was stirred for 1 hour. Purification by preparative LCMS (pH 2) gave the desired compound (17 mg, 27%). LCMS calculated for $C_{13}H_{18}FN_6O_4S$ (M+H)$^+$: m/z=373.1. $^1$H NMR (400 MHz, DMSO-d$_6$): δ 11.25 (s, 1H), 8.61 (s, 1H), 7.18 (m, 1H), 6.91 (m, 1H), 6.72 (m, 1H), 6.58 (m, 1H), 6.24 (s, 1H), 3.32 (m, 2H), 3.11 (m, 2H), 2.89 (s, 3H), 2.05 (s, 3H).

Example 18

4-({2-[(Aminosulfonyl)amino]ethyl}amino)-N-(3-cyano-4-fluorophenyl)-N'-hydroxy-1,2,5-oxadiazole-3-carboximidamide

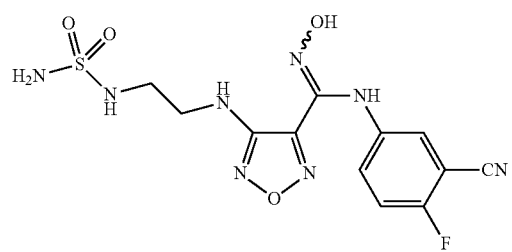 [SMILES: N#Cc1cc(NC(=NO)c2nonc2NCCNS(N)(=O)=O)ccc1F]

Step A: N-(3-Cyano-4-fluorophenyl)-N'-hydroxy-4-[(2-methoxyethyl)amino]-1,2,5-oxadiazole-3-carboximidamide

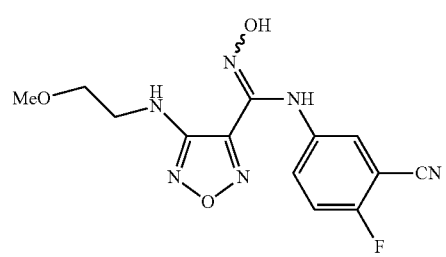 [SMILES: COCCNc1nonc1C(=NO)Nc1ccc(F)c(C#N)c1]

The desired compound was prepared according to the procedure of Example 13, step A, using N-hydroxy-4-[(2-methoxyethyl)amino]-1,2,5-oxadiazole-3-carboximidoyl chloride [made according to Example 1, steps A through E] and 5-amino-2-fluorobenzonitrile [Aldrich, product #639877] as the starting materials in 100% yield. LCMS for $C_{13}H_{14}FN_6O_3$ (M+H)$^+$: m/z=321.0.

Step B: 2-Fluoro-5-[3-{4-[(2-methoxyethyl)amino]-1,2,5-oxadiazol-3-yl}-5-oxo-1,2,4-oxadiazol-4(5H)-yl]benzonitrile

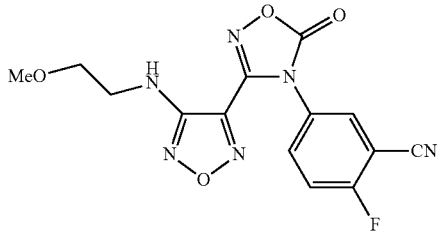

The desired compound was prepared according to the procedure of Example 13, step B, using N-(3-cyano-4-fluorophenyl)-N'-hydroxy-4-[(2-methoxyethyl)amino]-1,2,5-oxadiazole-3-carboximidamide as the starting material in 91% yield. LCMS for $C_{14}H_{12}FN_6O_4$ (M+H)$^+$: m/z=347.0. $^1$H NMR (400 MHz, DMSO-d$_6$): δ 8.25 (dd, J=5.7, 2.6 Hz, 1H), 8.06 (m, 1H), 7.77 (t, J=9.2 Hz, 1H), 6.41 (t, J=5.7 Hz, 1H), 3.48 (m, 2H), 3.40 (q, J=5.4 Hz, 2H), 3.25 (s, 3H).

Step C: 2-Fluoro-5-[3-{4-[(2-hydroxyethyl)amino]-1,2,5-oxadiazol-3-yl}-5-oxo-1,2,4-oxadiazol-4(5H)-yl]benzonitrile

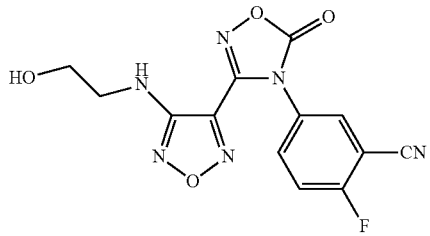 [SMILES: N#Cc1cc(-n2c(-c3nonc3NCCO)noc2=O)ccc1F]

The desired compound was prepared according to the procedure of Example 13, step C, using 2-fluoro-5-[3-{4-[(2-methoxyethyl)amino]-1,2,5-oxadiazol-3-yl}-5-oxo-1,2,4-oxadiazol-4(5H)-yl]benzonitrile as the starting material in quantitative yield. LCMS for $C_{13}H_{10}FN_6O_4$ (M+H)$^+$: m/z=333.0.

Step D: 2-({4-[4-(3-Cyano-4-fluorophenyl)-5-oxo-4,5-dihydro-1,2,4-oxadiazol-3-yl]-1,2,5-oxadiazol-3-yl}amino)ethyl methanesulfonate

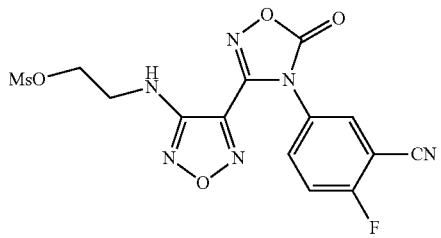 [SMILES: CS(=O)(=O)OCCNc1nonc1-c1noc(=O)n1-c1ccc(F)c(C#N)c1]

The desired compound was prepared according to the procedure of Example 13, step D, using 2-fluoro-5-[3-{4-[(2-hydroxyethyl)amino]-1,2,5-oxadiazol-3-yl}-5-oxo-1,2,4-oxadiazol-4(5H)-yl]benzonitrile as the starting material in 88% yield. LCMS for $C_{14}H_{12}FN_6O_6S$ (M+H)$^+$: m/z=411.0.

Step E: 5-[3-{4-[(2-Azidoethyl)amino]-1,2,5-oxadiazol-3-yl}-5-oxo-1,2,4-oxadiazol-4 (5H)-yl]-2-fluorobenzonitrile

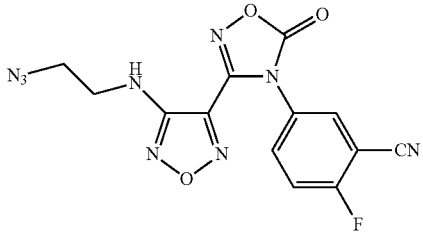 [SMILES: N#Cc1cc(-n2c(-c3nonc3NCCN=[N+]=[N-])noc2=O)ccc1F]

The desired compound was prepared according to the procedure of Example 13, step E, using 2-({4-[4-(3-cyano-4-fluorophenyl)-5-oxo-4,5-dihydro-1,2,4-oxadiazol-3-yl]-1,2,5-oxadiazol-3-yl}amino)ethyl methanesulfonate as the starting material in 95% yield.

Step F: 5-[3-{4-[(2-Aminoethyl)amino]-1,2,5-oxadiazol-3-yl}-5-oxo-1,2,4-oxadiazol-4 (5H)-yl]-2-fluorobenzonitrile hydroiodide

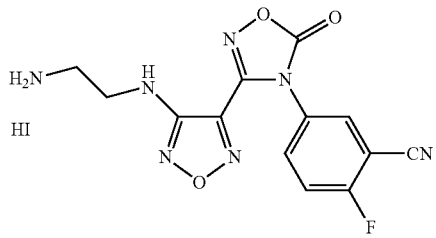

The desired compound was prepared according to the procedure of Example 13, step F, using 5-[3-{4-[(2-azidoethyl)amino]-1,2,5-oxadiazol-3-yl}-5-oxo-1,2,4-oxadiazol-4 (5H)-yl]-2-fluorobenzonitrile as the starting material in 57% yield. LCMS for $C_{13}H_{11}FN_7O_3$ (M+H)$^+$: m/z=332.0. $^1$H NMR (400 MHz, DMSO-d$_6$): δ 8.29 (dd, J=5.8, 2.7 Hz, 1H), 8.09 (m, 1H), 7.83 (br s, 3H), 7.79 (t, J=9.0 Hz, 1H), 6.77 (t, J=5.9 Hz, 1H), 3.50 (q, J=6.4 Hz, 2H), 3.04 (m, 2H).

Step G: 4-({2-[(Aminosulfonyl)amino]ethyl}amino)-N-(3-cyano-4-fluorophenyl)-N'-hydroxy-1,2,5-oxadiazole-3-carboximidamide In a microwave vial, 5-[3-{4-[(2-aminoethyl)amino]-1,2,5-oxadiazol-3-yl}-5-oxo-1,2,4-oxadiazol-4(5H)-yl]-2-fluorobenzonitrile hydroiodide (20.0 mg, 0.044 mmol) and sulfamide (25 mg, 0.26 mmol) were suspended in pyridine (0.5 mL). The reaction was heated to 120° C. for 10 minutes in a microwave reactor. The solvent was removed and the residue dissolved in methanol (0.17 mL). A solution of 2.0 N NaOH in water (0.22 mL, 0.44 mmol) was added in one portion. The reaction was stirred at room temperature overnight. After neutralization with acetic acid (50 μL), the product was purified using preparative LCMS to give the title compound (4.9 mg, 29%). LCMS for $C_{12}H_{14}FN_8O_4S$ (M+H)$^+$: m/z=385.0. $^1$H NMR (400 MHz, DMSO-d$_6$): δ 11.65 (s, 1H), 9.08 (s, 1H), 7.34 (t, J=9.1 Hz, 1H), 7.22 (dd, J=5.4, 2.8 Hz, 1H), 7.13 (m, 1H), 6.70 (t, J=5.9 Hz, 1H), 6.59 (s, 2H), 6.20 (t, J=6.1 Hz, 1H), 3.34 (m, 2H), 3.09 (m, 2H).

Example 19

N-(3-Cyano-4-fluorophenyl)-N'-hydroxy-4-({2-[(methylsulfonyl)amino]ethyl}amino)-1,2,5-oxadiazole-3-carboximidamide

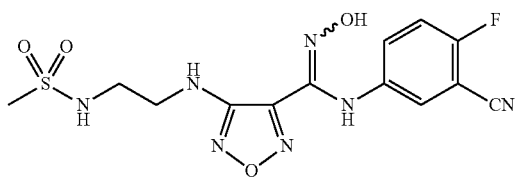 [SMILES: CS(=O)(=O)NCCNc1nonc1C(=NO)Nc1ccc(F)c(C#N)c1]

The title compound was prepared according to the procedure of Example 17, step E, using N'-hydroxy-4-({2-[(methylsulfonyl)amino]ethyl}amino)-1,2,5-oxadiazole-3-carboximidamide and 3-cyano-4-fluoroaniline [Aldrich, product #639877] as the starting materials. LCMS for C₁₃H₁₄FN₇NaO₄S (M+Na)⁺: m/z=406.0. ¹H NMR (400 MHz, DMSO-d₆): δ 11.65 (s, 1H), 9.08 (s, 1H), 7.35 (m, 1H), 7.18 (m, 3H), 6.56 (m, 1H), 6.23 (m, 1H), 6.24 (s, 2H), 3.32 (m, 2H), 3.14 (m, 2H), 2.89 (s, 3H).

Example 20

4-({2-[(Aminosulfonyl)amino]ethyl}amino)-N-[(4-bromo-2-furyl)methyl]-N'-hydroxy-1,2,5-oxadiazole-3-carboximidamide

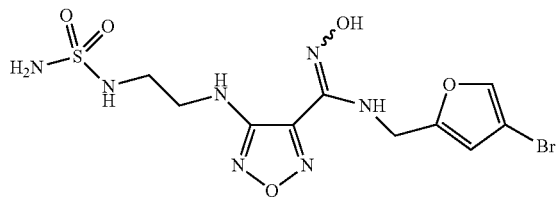 [SMILES: NS(=O)(=O)NCCNc1nonc1C(=NO)NCc1cc(Br)co1]

Step A: tert-Butyl [(4-bromo-2-furyl)methyl]carbamate

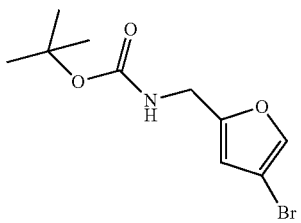

4-Bromo-2-furaldehyde [Aldrich, product #666599] (10.0 g, 57.1 mmol) was dissolved in ethanol (50 mL) and water (50 mL). N-Hydroxyamine hydrochloride (7.15 g, 103 mmol) and sodium acetate (8.44 g, 103 mmol) were added sequentially and the reaction mixture was brought to reflux at 100° C. for 1 hour. The solution was partially concentrated and the precipitate was collected and washed with cold water (2×10 mL). The filtrate was extracted with ethyl acetate (3×25 mL) and the combined organic layers were washed with brine (50 mL). After drying over sodium sulfate, the solution was concentrated in vacuo. The residue was combined with the precipitate and dissolved in acetic acid (70 mL). After placing in an ice-bath, zinc (14.7 g, 225 mmol) was added portion-wise over 25 minutes. The reaction warmed to room temperature over 1.5 hours and was filtered through Celite. The solvent was removed in vacuo.

The residue was stirred in tetrahydrofuran (72 mL). A solution of 2.0 N NaOH in water (179 mL, 358 mmol) was added dropwise over 45 minutes. After 5 minutes, di-tert-butyldicarbonate (16.9 g, 77.4 mmol) was added dropwise. The reaction was stirred for 2 hours and the tetrahydrofuran was removed in vacuo. Ethyl acetate (100 mL) was added and the suspension was filtered. The organic layer was collected and the product extracted with ethyl acetate (2×50 mL). The combined organic layers were washed with brine (100 mL) and water (100 mL), dried over sodium sulfate and concentrated in vacuo to give the desired product (15.3 g, 79%). LCMS calculated for C₁₀H₁₄BrNNaO₃ (M+Na)⁺: m/z=298.0. ¹H NMR (400 MHz, DMSO-d₆): δ 7.79 (s, 1H), 7.37 (t, J=5.8 Hz, 1H), 6.33 (s, 1H), 4.06 (d, J=6.1 Hz, 2H), 1.36 (s, 9H).

Step B: 1-(4-Bromo-2-furyl)methanamine trifluoroacetate

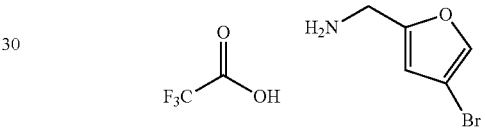

Under a nitrogen atmosphere, a solution of tert-butyl [(4-bromo-2-furyl)methyl]carbamate (153 g, 55.4 mmol) in dichloromethane (86 mL) at 0° C. was treated with trifluoroacetic acid (43 mL) over 15 minutes. The reaction mixture warmed to room temperature over 30 minutes. The solvent was removed in vacuo and chased with toluene (3×50 mL). The product was lyophilized for 18 hours to give the desired product as a brown solid (13.0 g, 81%). LCMS calculated for C₅H₄BrO (M−NH₂)⁺: m/z=158.9, 160.9. ¹H NMR (400 MHz, DMSO-d₆): δ 8.34 (br s, 3H), 8.01 (s, 1H), 6.70 (s, 1H), 4.08 (s, 1H).

Step C: N-[(4-Bromo-2-furyl)methyl]-N'-hydroxy-4-[(2-methoxyethyl)amino]-1,2,5-oxadiazole-3-carboximidamide

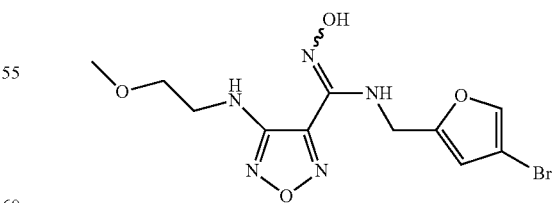

N-Hydroxy-4-(2-methoxyethylamino)-1,2,5-oxadiazole-3-carbimidoyl chloride [prepared according to the procedure of Example 1, steps A through E] (4.5 g, 20.3 mmol) was stirred in ethanol (20 mL) at room temperature. To this, a solution of 1-(4-bromo-2-furyl)methanamine trifluoroacetate (6.5 g, 22.4 mmol) in ethanol (24 mL) was added and the mixture was stirred for 15 minutes. Triethylamine (6.3 mL, 44.8 mmol) was added dropwise over 10 minutes and the reaction was stirred for an additional 15 minutes. The solvent was removed in vacuo and after adding water (50 mL), the product was extracted with ethyl acetate (3×50 mL). The combined organic layers were washed with brine (50 mL), dried over sodium sulfate and concentrated to give the desired product (7.5 g, 100%). LCMS calculated for $C_{11}H_{15}BrN_5O_4$ $(M+H)^+$: m/z=359.9, 361.9.

Step D: 4-[(4-Bromo-2-furyl)methyl]-3-{4-[(2-methoxyethyl)amino]-1,2,5-oxadiazol-3-yl}-1,2,4-oxadiazol-5(4H)-one

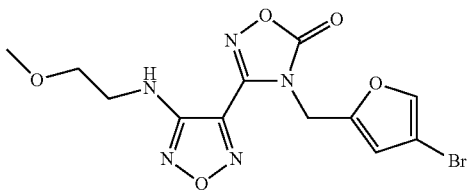 [SMILES: COCCNc1nonc1-c1noc(=O)n1Cc1cc(Br)co1]

N-[(4-Bromo-2-furyl)methyl]-N'-hydroxy-4-[(2-methoxyethyl)amino]-1,2,5-oxadiazole-3-carboximidamide (7.3 g, 20.4 mmol) and 1,1'-carbonyldiimidazole (5.0 g, 30.5 mmol) were dissolved in ethyl acetate (72 mL). The reaction mixture was heated at 65° C. for 15 minutes. Ethyl acetate (70 mL) was added and the crude reaction was washed with 0.1 N hydrogen chloride in water (2×70 mL). The organic layer was dried over sodium sulfate and concentrated in vacuo. Purification by flash chromatography on silica gel with an eluent of ethyl acetate in hexanes gave the desired product (4.1 g, 90%). LCMS calculated for $C_{12}H_{13}BrN_5O_5$ $(M+H)^+$: m/z=386.0, 388.0. $^1$H NMR (400 MHz, CD$_3$OD): δ 7.88 (s, 1H), 6.67 (s, 1H), 6.39 (t, J=5.7 Hz, 1H), 5.07 (s, 2H), 3.50 (m, 2H), 3.41 (q, J=5.7 Hz, 2H), 3.25 (s, 3H).

Step E: 4-[(4-Bromo-2-furyl)methyl]-3-{4-[(2-hydroxyethyl)amino]-1,2,5-oxadiazol-3-yl}-1,2,4-oxadiazol-5(4H)-one

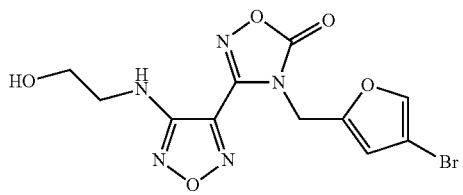 [SMILES: O=c1onc(-c2nonc2NCCO)n1Cc1cc(Br)co1]

In a round bottom flask under nitrogen atmosphere, 4-[(4-bromo-2-furyl)methyl]-3-{4-[(2-methoxyethyl)amino]-1,2,5-oxadiazol-3-yl}-1,2,4-oxadiazol-5(4H)-one (8.2 g, 21 mmol) was stirred in dichloromethane (68 mL). The temperature was brought to −78° C. and a solution of 1.0 M boron tribromide in dichloromethane (43 mL, 43 mmol) was added dropwise over 45 minutes. The reaction stirred at −78° C. for 45 minutes and continued to stir at 0° C. for an additional 30 minutes. While remaining at 0° C., a saturated solution of sodium bicarbonate in water (120 mL) was added dropwise over 25 minutes. After warming to room temperature, the organic layer was collected and the aqueous layer was extracted with ethyl acetate (2×50 mL). The combined organic layers were washed with brine (100 mL), dried over sodium sulfate and concentrated in vacuo to give the desired product (7.7 g, 97%) along with a small amount of 3-{4-[(2-bromoethyl)amino]-1,2,5-oxadiazol-3-yl}-4-[(4-bromo-2-furyl)methyl]-1,2,4-oxadiazol-5(4H)-one. LCMS calculated for $C_{11}H_{11}BrN_5O_5$ $(M+H)^+$: m/z=371.7, 374.0. $^1$H NMR (400 MHz, DMSO-d$_6$): δ 7.89 (s, 1H), 6.68 (s, 1H), 6.31 (t, J=5.8 Hz, 1H), 5.08 (s, 2H), 4.85 (br s, 1H), 3.56 (m, 2H), 3.30 (q, J=5.6 Hz, 2H).

Step F: 2-[(4-{4-[(4-Bromo-2-furyl)methyl]-5-oxo-4,5-dihydro-1,2,4-oxadiazol-3-yl}-1,2,5-oxadiazol-3-yl)amino]ethyl methanesulfonate

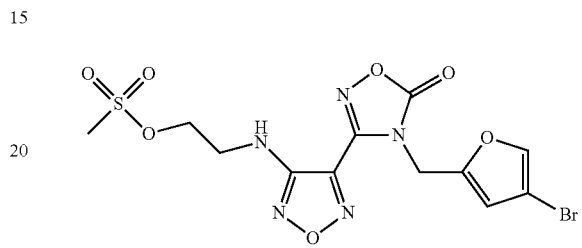

To a solution of 4-[(4-bromo-2-furyl)methyl]-3-{4-[(2-hydroxyethyl)amino]-1,2,5-oxadiazol-3-yl}-1,2,4-oxadiazol-5(4H)-one (7.7 g, 21 mmol, containing also some of the corresponding bromo-compound) in ethyl acetate (100 mL) was added methanesulfonyl chloride (0.96 mL, 12 mmol) in one portion. The reaction was stirred for 5 minutes and triethylamine (1.6 mL, 11 mmol) was added, also in one portion. After stirring for 30 minutes, additional methanesulfonyl chloride (0.4 mL, 5 mmol) was added, followed 5 minutes later by triethylamine (0.58 mL, 4.2 mmol). After 15 minutes, the reaction was quenched with the addition of water (100 mL). The product was extracted with ethyl acetate (3×50 mL) and the combined organic layers washed with brine (100 mL). After drying over sodium sulfate, the solvent was removed in vacuo to give the desired product (9.3 g, 100%). LCMS calculated for $C_{12}H_{13}BrN_5O_7S$ $(M+H)^+$: m/z=449.8, 451.8. $^1$H NMR (300 MHz, DMSO-d$_6$): δ 7.88 (s, 1H), 6.73 (t, J=6.2 Hz, 1H), 6.68 (s, 1H), 5.08 (s, 2H), 4.37 (m, 2H), 3.59 (q, J=5.8 Hz, 2H), 3.16 (s, 3H).

Step G: 3-{4-[(2-Azidoethyl)amino]-1,2,5-oxadiazol-3-yl}-4-[(4-bromo-2-furyl)methyl]-1,2,4-oxadiazol-5(4H)-one

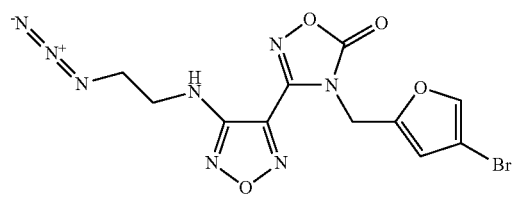

2-[(4-{4-[(4-Bromo-2-furyl)methyl]-5-oxo-4,5-dihydro-1,2,4-oxadiazol-3-yl}-1,2,5-oxadiazol-3-yl)amino]ethyl methanesulfonate (9.1 g, 20 mmol, containing also some of the corresponding bromo-compound) was dissolved in dimethylformamide (90 mL). Sodium azide (1.97 g, 30.3 mmol) was added in one portion and after 5 minutes, the temperature was brought to 65° C. The reaction stirred for 2 hours and was allowed to cool back to room temperature. Water (200 mL)

was added to quench the reaction. The product was extracted with ethyl acetate (3×100 mL) and the combined organic layers were washed with brine (2×150 mL) and water (150 mL). After drying over sodium sulfate, the solvent was removed in vacuo to give the desired product (7.7 g, 96%). LCMS calculated for $C_{11}H_9BrN_8NaO_4$ (M+Na)$^+$: m/z=418.7, 421.0. $^1$H NMR (400 MHz, DMSO-d$_6$): δ 7.88 (s, 1H), 6.71 (t, J=5.7 Hz, 1H), 6.68 (s, 1H), 5.08 (s, 2H), 3.54 (t, J=5.7 Hz, 2H), 3.47 (q, J=5.7 Hz, 2H).

Step H: 3-{4-[(2-Aminoethyl)amino]-1,2,5-oxadiazol-3-yl}-4-[(4-bromo-2-furyl)methyl]-1,2,4-oxadiazol-5(4H)-one hydroiodide

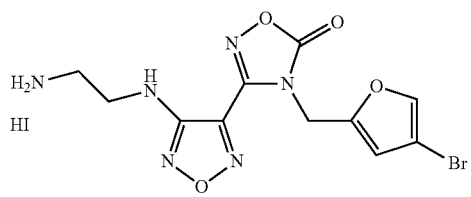

To a solution of 3-{4-[(2-azidoethyl)amino]-1,2,5-oxadiazol-3-yl}-4-[(4-bromo-2-furyl)methyl]-1,2,4-oxadiazol-5(4H)-one (7.7 g, 19 mmol) in methanol (80 mL) was added sodium iodide (17.4 g, 116 mmol). After stirring for 10 minutes, a solution of chlorotrimethylsilane (14.8 mL, 116 mmol) was added dropwise over 5 minutes. The reaction continued to stir for 1 hour, at which time it was slowly added to a solution of sodium thiosulfate (23.0 g, 145 mmol) in water (800 mL) at 0° C., resulting in a precipitate. The flask was rinsed with methanol (10 mL) and the precipitate was collected through vacuum filtration. The solid was rinsed with cold water (2×25 mL) and was dried under vacuum to give the desired product (5.8 g, 60%) as the hydroiodide salt. LCMS calculated for $C_{11}H_{12}BrN_6O_4$ (M+H)$^+$: m/z=370.9, 372.8. $^1$H NMR (400 MHz, DMSO-d$_6$): δ 7.86 (s, 1H), 7.36 (br s, 3H), 6.68 (t, J=5.8 Hz, 1H), 6.65 (s, 1H), 5.07 (s, 2H), 3.45 (q, J=5.8 Hz, 2H), 2.98 (t, J=5.8 Hz, 2H).

Step I: 4-({2-[(Aminosulfonyl)amino]ethyl}amino)-N-[(4-bromo-2-furyl)methyl]-N'-hydroxy-1,2,5-oxadiazole-3-carboximidamide

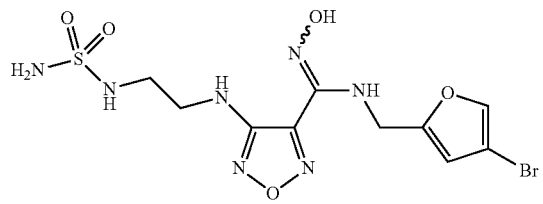 [SMILES: NS(=O)(=O)NCCNc1nonc1C(=NO)NCc1cc(Br)co1]

In a microwave vial, 3-{4-[(2-aminoethyl)amino]-1,2,5-oxadiazol-3-yl}-4-[(4-bromo-2-furyl)methyl]-1,2,4-oxadiazol-5(4H)-one hydroiodide (30 mg, 0.060 mmol) and sulfamide (29 mg, 0.30 mmol) were suspended in pyridine (1 mL). The reaction mixture was flushed with nitrogen and heated at 130° C. for 3 minutes in a microwave reactor. The solvent was removed and the crude intermediate was suspended in methanol (1 mL). A 2.0 N solution of NaOH in water (0.30 mL, 0.60 mmol) was added in one portion and the reaction was heated to 45° C. for 30 minutes. After neutralization with acetic acid (68 μL, 1.2 mmol), the product was purified by preparative LCMS to give the desired product (10.4 mg, 41%). LCMS calculated for $C_{10}H_{15}BrN_7O_5S$ (M+H)$^+$: m/z=423.9, 426.0. $^1$H NMR (400 MHz, DMSO-d$_6$): δ 10.87 (s, 1H), 7.75 (s, 1H), 6.83 (t, J=7.3 Hz, 1H), 6.68 (t, J=6.0 Hz, 1H), 6.56 (s, 2H), 6.30 (t, J=6.0 Hz, 1H), 6.23 (s, 1H), 4.56 (d, J=7.0 Hz, 2H), 3.32 (q, J=6.3 Hz, 2H), 3.07 (q, J=6.3 Hz, 2H).

Example 21

4-({2-[(Aminosulfonyl)amino]ethyl}amino)-N-[(4-chloro-2-furyl)methyl]-N'-hydroxy-1,2,5-oxadiazole-3-carboximidamide

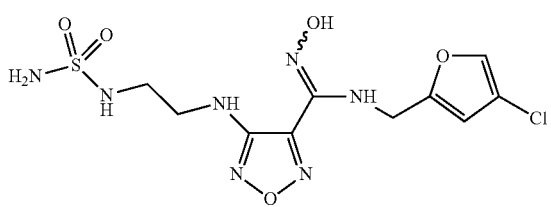 [SMILES: NS(=O)(=O)NCCNc1nonc1C(=NO)NCc1cc(Cl)co1]

Step A: 4-Chloro-2-furaldehyde

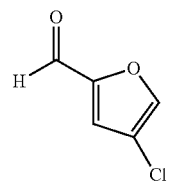

To a stirred suspension of aluminum trichloride (29.8 g, 0.223 mol) in dichloromethane (200 mL) under nitrogen atmosphere was added 2-furancarboxaldehyde (8.44 mL, 0.102 mol) over 15 minutes. After stirring for 30 minutes, chlorine was bubbled into the suspension using a pipette over a time period of 50 minutes. The flask was sealed and left to stir at room temperature for 90 hours. The reaction mixture was slowly added to a mixture of ice (500 mL) in a solution of 1.0 N hydrogen chloride in water (300 mL). The mixture was left to warm to room temperature over the next hour. The layers were separated and the organic layer collected. Additional product was extracted with dichloromethane (2×200 mL). The combined organic layers were washed with water (250 mL) and dried over sodium sulfate. The solvent was removed in vacuo to give a crude mixture containing the desired product (14.0 g, 100%, 60% purity). $^1$H NMR (400 MHz, DMSO-d$_6$): δ 9.56 (s, 1H), 8.36 (s, 1H), 7.71 (s, 1H).

Step B: tert-Butyl [(4-chloro-2-furyl)methyl]carbamate

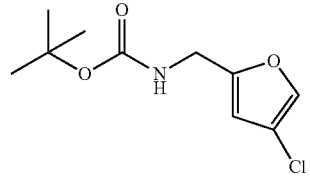

4-Chloro-2-furaldehyde (14.0 g, 60% purity, 64 mmol) was dissolved in ethanol (50 mL) and water (50 mL). N-Hydroxyamine hydrochloride (12.6 g, 182 mmol) and sodium acetate (14.9 g, 182 mmol) were added sequentially and the reaction mixture was brought to reflux at 100° C. for 1 hour. The solution was partially concentrated then water (25 mL) and ethyl acetate (50 mL) were added. The organic layer was collected and the aqueous was extracted with ethyl acetate (2×25 mL). The combined organic layers were washed with brine (50 mL) and water (50 mL). After drying over sodium sulfate, the solution was concentrated in vacuo. The intermediate was suspended in acetic acid (115 mL). The solution was cooled in an ice-bath and zinc (33.1 g, 506 mmol) was added portion-wise over 20 minutes. The reaction warmed to room temperature over 2 hours and was filtered through Celite. The solvent was removed in vacuo.

The residue was stirred in tetrahydrofuran (100 mL). A solution of 2.0 M NaOH in water (152 mL, 304 mmol) was added dropwise over 30 minutes. The reaction mixture was placed in an ice-bath and after 5 minutes, di-tert-butyldicarbonate (24.3 g, 111 mmol) was added dropwise over 15 minutes. The reaction was allowed to warm to room temperature over the next 2 hours and the tetrahydrofuran was then removed in vacuo. Ethyl acetate (100 mL) was added and the suspension was filtered. The organic layer was collected and the aqueous layer extracted with ethyl acetate (2×100 mL). The combined organic layers were washed with a 1:1 mixture of water/brine (100 mL), dried over sodium sulfate and concentrated in vacuo. Purification by flash chromatography on silica gel with an eluent of ethyl acetate in hexanes gave the desired product (3.05 g, 22%). LCMS calculated for C$_{10}$H$_{14}$ClNNaO$_3$ (M+Na)$^+$: m/z=253.9. $^1$H NMR (400 MHz, DMSO-d$_6$): δ 7.81 (s, 1H), 7.37 (t, J=5.3 Hz, 1H), 6.32 (s, 1H), 4.05 (d, J=6.0 Hz, 2H), 1.36 (s, 9H).

Step C: 1-(4-Chloro-2-furyl)methanamine trifluoroacetate

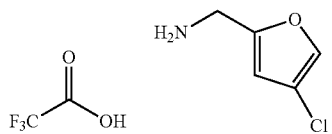 [SMILES: O=C(O)C(F)(F)F ; NCc1cc(Cl)co1]

The desired compound was prepared according to the procedure of Example 20, step B, using tert-butyl [(4-chloro-2-furyl)methyl]carbamate as the starting material in quantitative yield. LCMS calculated for C$_5$H$_4$ClO (M−NH$_2$)$^+$: m/z=115.0. $^1$H NMR (400 MHz, DMSO-d$_6$): δ 8.29 (br s, 3H), 8.04 (s, 1H), 6.69 (s, 1H), 4.07 (s, 2H).

Step D: N-[(4-Chloro-2-furyl)methyl]-N'-hydroxy-4-[(2-methoxyethyl)amino]-1,2,5-oxadiazole-3-carboximidamide

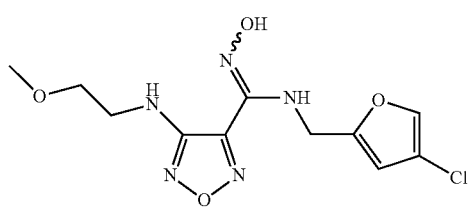 [SMILES: COCCNc1nonc1C(=NO)NCc1cc(Cl)co1]

The desired compound was prepared according to the procedure of Example 20, step C, using N-hydroxy-4-(2-methoxyethylamino)-1,2,5-oxadiazole-3-carbimidoyl chloride and 1-(4-chloro-2-furyl)methanamine trifluoroacetate as the starting material in quantitative yield. LCMS calculated for C$_{11}$H$_{15}$ClN$_5$O$_4$ (M+H)$^+$: m/z=316.0.

Step E: 4-[(4-Chloro-2-furyl)methyl]-3-{4-[(2-methoxyethyl)amino]-1,2,5-oxadiazol-3-yl}-1,2,4-oxadiazol-5(4H)-one

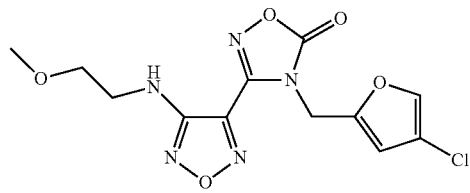 [SMILES: COCCNc1nonc1-c1noc(=O)n1Cc1cc(Cl)co1]

The desired compound was prepared according to the procedure of Example 20, step D, using N-[(4-chloro-2-furyl)methyl]-N'-hydroxy-4-[(2-methoxyethyl)amino]-1,2,5-oxadiazole-3-carboximidamide as the starting material in 51% yield. LCMS calculated for C$_{12}$H$_{13}$ClN$_5$O$_5$ (M+H)$^+$: m/z=342.0.

Step F: 4-[(4-Chloro-2-furyl)methyl]-3-{4-[(2-hydroxyethyl)amino]-1,2,5-oxadiazol-3-yl}-1,2,4-oxadiazol-5(4H)-one

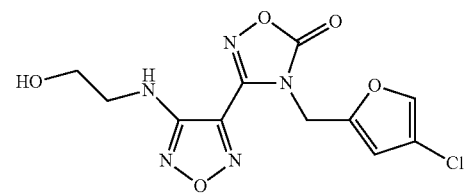 [SMILES: O=c1onc(-c2nonc2NCCO)n1Cc1cc(Cl)co1]

The desired compound was prepared according to the procedure of Example 20, step E, using 4-[(4-chloro-2-furyl)methyl]-3-{4-[(2-methoxyethyl)amino]-1,2,5-oxadiazol-3-yl}-1,2,4-oxadiazol-5(4H)-one as the starting material in quantitative yield. LCMS calculated for C$_{11}$H$_{10}$ClN$_5$NaO$_5$ (M+Na)$^+$: m/z=349.9.

Step G: 2-[(4-{4-[(4-Chloro-2-furyl)methyl]-5-oxo-4,5-dihydro-1,2,4-oxadiazol-3-yl}-1,2,5-oxadiazol-3-yl)amino]ethyl methanesulfonate

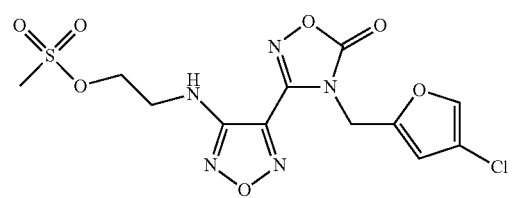 [SMILES: CS(=O)(=O)OCCNc1nonc1-c1noc(=O)n1Cc1cc(Cl)co1]

The desired compound was prepared according to the procedure of Example 20, step F, using 4-[(4-chloro-2-furyl)methyl]-3-{4-[(2-hydroxyethyl)amino]-1,2,5-oxadiazol-3-yl}-1,2,4-oxadiazol-5(4H)-one as the starting material in 69% yield. LCMS calculated for C$_{12}$H$_{13}$ClN$_5$O$_7$S (M+H)$^+$: m/z=405.8.

83

Step H: 3-{4-[(2-Azidoethyl)amino]-1,2,5-oxadiazol-3-yl}-4-[(4-chloro-2-furyl)methyl]-1,2,4-oxadiazol-5(4H)-one

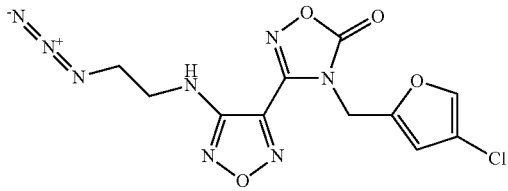

The desired compound was prepared according to the procedure of Example 20, step G, using 2-[(4-{4-[(4-chloro-2-furyl)methyl]-5-oxo-4,5-dihydro-1,2,4-oxadiazol-3-yl}-1,2,5-oxadiazol-3-yl)amino]ethyl methanesulfonate as the starting material in quantitative yield. LCMS calculated for $C_{11}H_9ClN_8NaO_4$ (M+Na)$^+$: m/z=374.9.

Step I: 3-{4-[(2-Aminoethyl)amino]-1,2,5-oxadiazol-3-yl}-4-[(4-chloro-2-furyl)methyl]-1,2,4-oxadiazol-5(4H)-one hydroiodide

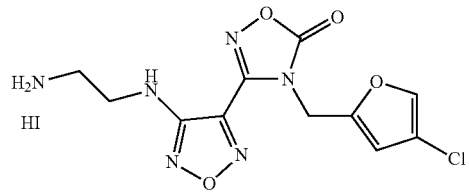

The desired compound was prepared according to the procedure of Example 20, step H, using 3-{4-[(2-azidoethyl)amino]-1,2,5-oxadiazol-3-yl}-4-[(4-chloro-2-furyl)methyl]-1,2,4-oxadiazol-5(4H)-one as the starting material in 57% yield. LCMS calculated for $C_{11}H_{12}ClN_6O_4$ (M+H)$^+$: m/z=326.9.

Step J: 4-({2-[(Aminosulfonyl)amino]ethyl}amino)-N-[(4-chloro-2-furyl)methyl]-N'-hydroxy-1,2,5-oxadiazole-3-carboximidamide

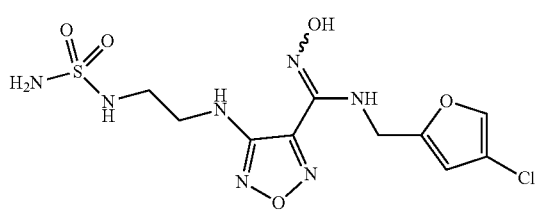 [SMILES: NS(=O)(=O)NCCNc1nonc1C(=NO)NCc1cc(Cl)co1]

The desired compound was prepared according to the procedure of Example 20, step I, using 3-{4-[(2-aminoethyl)amino]-1,2,5-oxadiazol-3-yl}-4-[(4-chloro-2-furyl)methyl]-1,2,4-oxadiazol-5(4H)-one hydroiodide as the starting material in 53% yield, LCMS calculated for $C_{10}H_{15}ClN_7O_5S$ (M+H)$^+$: m/z=379.9. $^1$H NMR (400 MHz, DMSO-d$_6$): δ 10.88 (s, 1H), 7.77 (s, 1H), 6.83 (t, J=6.8 Hz, 1H), 6.68 (t, J=5.9 Hz, 1H), 6.56 (s, 2H), 6.30 (t, J=5.9 Hz, 1H), 6.22 (s, 1H), 4.55 (d, 2H), 3.32 (q, J=6.3 Hz, 2H), 3.06 (q, J=6.3 Hz, 2H).

84

Example 22

Alternate Preparation of the Intermediate 3-(4-(2-aminoethylamino)-1,2,5-oxadiazol-3-yl)-4-(3-bromo-4-fluorophenyl)-1,2,4-oxadiazol-5(4H)-one hydroiodide

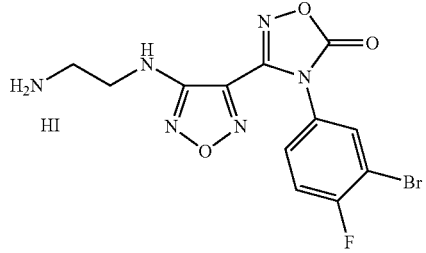

Step A: 4-Amino-N'-hydroxy-N-(2-methoxyethyl)-1,2,5-oxadiazole-3-carboximidamide

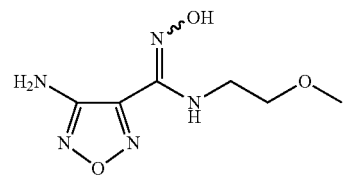

4-Amino-N-hydroxy-1,2,5-oxadiazole-3-carboximidoyl chloride (can be prepared according to Example 1, steps A-B, 200.0 g, 1.23 mol) was mixed with ethyl acetate (1.2 L). At 0-5° C. 2-methoxyethylamine [Aldrich, product #143693] (119.0 mL, 1.35 mol) was added in one portion while stirring. The reaction temperature rose to 41° C. The reaction was cooled to 0-5° C. Triethylamine (258 mL, 1.84 mol) was added. After stirring 5 min, LCMS indicated reaction completion. The reaction solution was washed with water (500 mL) and brine (500 mL), dried over sodium sulfate, and concentrated to give the desired product (294 g, 119%) as a crude dark oil. LCMS for $C_6H_{12}N_5O_3$ (M+H)$^+$: m/z=202.3. $^1$H NMR (400 MHz, DMSO-d$_6$): δ 10.65 (s, 1H), 6.27 (s, 2H), 6.10 (t, J=6.5 Hz, 1H), 3.50 (m, 2H), 3.35 (d, J=5.8 Hz, 2H), 3.08 (s, 3H).

Step B: N'-Hydroxy-4-[(2-methoxyethyl)amino]-1,2,5-oxadiazole-3-carboximidamide

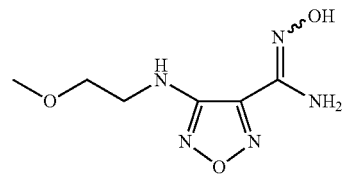

4-Amino-N'-hydroxy-N-(2-methoxyethyl)-1,2,5-oxadiazole-3-carboximidamide (248.0 g, 1.23 mol) was mixed with water (1 L). Potassium hydroxide (210 g, 3.7 mol) was added. The reaction was refluxed at 100° C. overnight (15 hours).

TLC with 50% ethyl acetate (containing 1% ammonium hydroxide) in hexane indicated reaction completed (product Rf=0.6, starting material Rf=0.5). LCMS also indicated reaction completion. The reaction was cooled to room temperature and extracted with ethyl acetate (3×1 L). The combined ethyl acetate solution was dried over sodium sulfate and concentrated to give the desired product (201 g, 81%) as a crude off-white solid. LCMS for $C_6H_{12}N_5O_3$ (M+H)$^+$: m/z=202.3 $^1$H NMR (400 MHz, DMSO-$d_6$): δ 10.54 (s, 1H), 6.22 (s, 2H), 6.15 (t, J=5.8 Hz, 1H), 3.45 (t, J=5.3 Hz, 2H), 3.35 (m, 2H), 3.22 (s, 3H).

Step C: N-Hydroxy-4-[(2-methoxyethyl)amino]-1,2,5-oxadiazole-3-carboximidoyl chloride

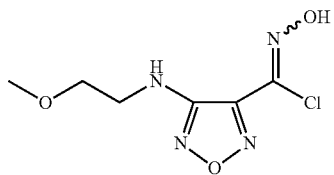

At room temperature N'-hydroxy-4-[(2-methoxyethyl)amino]-1,2,5-oxadiazole-3-carboximidamide (50.0 g, 0.226 mol) was dissolved in 6.0 M hydrochloric acid aqueous solution (250 mL, 1.5 mol). Sodium chloride (39.5 g, 0.676 mol) was added followed by water (250 mL) and ethyl acetate (250 mL). At 3-5° C. a previously prepared aqueous solution (100 mL) of sodium nitrite (15.0 g, 0.217 mol) was added slowly over 1 hr. The reaction was stirred at 3-8° C. for 2 hours and then room temperature over the weekend. LCMS indicated reaction completed. The reaction solution was extracted with ethyl acetate (2×200 mL). The combined ethyl acetate solution was dried over sodium sulfate and concentrated to give the desired product (49.9 g, 126%) as a crude white solid. LCMS for $C_6H_{10}ClN_4O_3$ (M+H)$^+$: m/z=221.0. $^1$H NMR (400 MHz, DMSO-$d_6$): δ 13.43 (s, 1H), 5.85 (t, J=5.6 Hz, 1H), 3.50 (t, J=5.6 Hz, 2H), 3.37 (dd, J=10.8, 5.6 Hz, 2H), 3.25 (s, 3H).

Step D: N-(3-Bromo-4-fluorophenyl)-N'-hydroxy-4-[(2-methoxyethyl)amino]-1,2,5-oxadiazole-3-carboximidamide

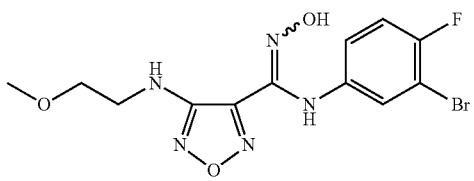

N-Hydroxy-4-[(2-methoxyethyl)amino]-1,2,5-oxadiazole-3-carboximidoyl chloride (46.0 g, 0.208 mol) was mixed with water (300 mL). The mixture was heated to 60° C. 3-Bromo-4-fluoroaniline [Oakwood products, product #013091] (43.6 g, 0.229 mol) was added and stirred for 10 min. A warm sodium bicarbonate (26.3 g, 0.313 mol) solution (300 mL water) was added over 15 min. The reaction was stirred at 60° C. for 20 min. LCMS indicated reaction completion. The reaction solution was cooled to room temperature and extracted with ethyl acetate (2×300 mL). The combined ethyl acetate solution was dried over sodium sulfate and concentrated to give the desired product (76.7 g, 98%) as a crude brown solid. LCMS for $C_{12}H_{14}BrFN_5O_3$ (M+H)$^+$: m/z=374.0, 376.0. $^1$H NMR (400 MHz, DMSO-$d_6$): δ 11.55 (s, 1H), 8.85 (s, 1H), 7.16 (t, J=8.8 Hz, 1H), 7.08 (dd, J=6.1, 2.7 Hz, 1H), 6.75 (m, 1H), 6.14 (t, J=5.8 Hz, 1H), 3.48 (t, J=5.2 Hz, 2H), 3.35 (dd, J=10.8, 5.6 Hz, 2H), 3.22 (s, 3H).

Step E: 4-(3-Bromo-4-fluorophenyl)-3-{4-[(2-methoxyethyl)amino]-1,2,5-oxadiazol-3-yl}-1,2,4-oxadiazol-5(4H)-one

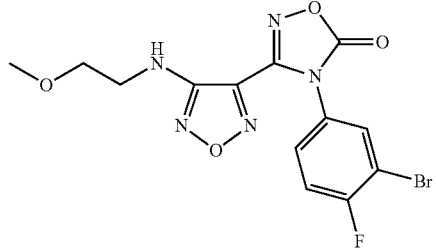 [SMILES: COCCNc1nonc1-c1noc(=O)n1-c1ccc(F)c(Br)c1]

A mixture of N-(3-bromo-4-fluorophenyl)-N'-hydroxy-4-[(2-methoxyethyl)amino]-1,2,5-oxadiazole-3-carboximidamide (76.5 g, 0.204 mol), 1,1'-carbonyldiimidazole (49.7 g, 0.307 mol), and ethyl acetate (720 mL) was heated to 60° C. and stirred for 20 min. LCMS indicated reaction completed. The reaction was cooled to room temperature, washed with 1 N HCl (2×750 mL), dried over sodium sulfate, and concentrated to give the desired product (80.4 g, 98%) as a crude brown solid. LCMS for $C_{13}H_{12}BrFN_5O_4$ (M+H)$^+$: m/z=400.0, 402.0. $^1$H NMR (400 MHz, DMSO-$d_6$): δ 7.94 (t, J=8.2 Hz, 1H), 7.72 (dd, J=9.1, 2.3 Hz, 1H), 7.42 (m, 1H), 6.42 (t, J=5.7 Hz, 1H), 3.46 (t, J=5.4 Hz, 2H), 3.36 (t, J=5.8 Hz, 2H), 3.26 (s, 3H).

Step F: 4-(3-Bromo-4-fluorophenyl)-3-{4-[(2-hydroxyethyl)amino]-1,2,5-oxadiazol-3-yl}-1,2,4-oxadiazol-5(4H)-one

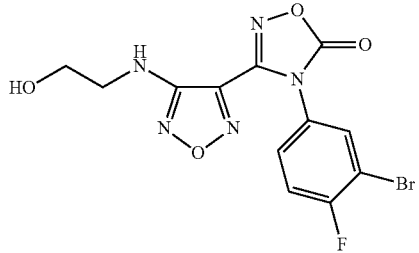

4-(3-Bromo-4-fluorophenyl)-3-{4-[(2-methoxyethyl)amino]-1,2,5-oxadiazol-3-yl}-1,2,4-oxadiazol-5(4H)-one (78.4 g, 0.196 mol) was dissolved in dichloromethane (600 mL). At −67° C. boron tribromide (37 mL, 0.392 mol) was added over 15 min. The reaction was warmed up to −10° C. in 30 min. LCMS indicated reaction completed. The reaction was stirred at room temperature for 1 hour. At 0-5° C. the reaction was slowly quenched with saturated sodium bicarbonate solution (1.5 L) over 30 min. The reaction temperature rose to 25° C. The reaction was extracted with ethyl acetate (2×500 mL, first extraction organic layer is on the bottom and second extraction organic lager is on the top). The combined organic layers were dried over sodium sulfate and concentrated to give the desired product (75 g, 99%) as a crude brown solid. LCMS for $C_{12}H_{10}BrFN_5O_4$ (M+H)$^+$: m/z=386.0, 388.0. $^1$H NMR (400 MHz, DMSO-$d_6$): δ 8.08 (dd, J=6.2, 2.5 Hz, 1H), 7.70 (m, 1H), 7.68 (t, J=8.7 Hz, 1H), 6.33 (t, J=5.6 Hz, 1H), 4.85 (t, J=5.0 Hz, 1H), 3.56 (dd, J=10.6, 5.6 Hz, 2H), 3.29 (dd, J=11.5, 5.9 Hz, 2H).

Step G: 2-({4-[4-(3-Bromo-4-fluorophenyl)-5-oxo-4,5-dihydro-1,2,4-oxadiazol-3-yl]-1,2,5-oxadiazol-3-yl}amino)ethyl methanesulfonate

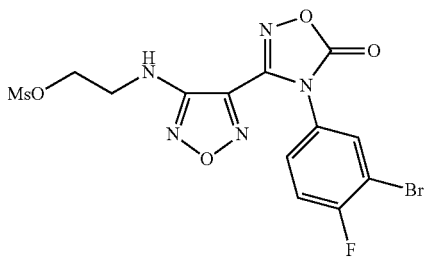 [SMILES: CS(=O)(=O)OCCNc1nonc1-c1noc(=O)n1-c1ccc(F)c(Br)c1]

4-(3-bromo-4-fluorophenyl)-3-(4-(2-hydroxyethylamino)-1,2,5-oxadiazol-3-yl)-1,2,4-oxadiazol-5(4H)-one (72.2 g, 0.188 mol) was mixed with ethyl acetate (600 mL). Methanesulfonyl chloride (19.2 mL, 0.248 mol) was added followed by triethylamine (34.9 mL, 0.250 mol). The reaction was stirred at room temperature for 5 min. When LCMS indicated completion of reaction (M+H=442), 500 mL of water was added into reaction. The reaction was extracted with ethyl acetate (2×500 mL). The combined ethyl acetate solution was washed with brine (500 mL), dried over sodium sulfate and concentrated to give 85.1 g crude brown solid. $^1$H NMR verified the structure. Crude yield was 97%. LCMS for $C_{13}H_{11}BrFN_5O_6SNa$ (M+Na)$^+$: m/z=485.9, 487.9. $^1$H NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.9 Hz, 1H), 4.36 (t, J=5.3 Hz, 2H), 3.58 (dd, J=11.2, 5.6 Hz, 2H), 3.18 (s, 3H).

Step H: 3-{4-[(2-Azidoethyl)amino]-1,2,5-oxadiazol-3-yl}-4-(3-bromo-4-fluorophenyl)-1,2,4-oxadiazol-5(4H)-one

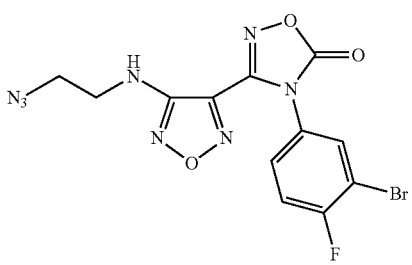 [SMILES: [N-]=[N+]=NCCNc1nonc1-c1noc(=O)n1-c1ccc(F)c(Br)c1]

2-(4-(4-(3-bromo-4-fluorophenyl)-5-oxo-4,5-dihydro-1,2,4-oxadiazol-3-yl)-1,2,5-oxadiazol-3-ylamino)ethyl methanesulfonate (50.0 g, 0.108 mol) was dissolved in N,N-dimethylformamide (83 mL). Sodium azide (10.5 g, 0.162 mol) was added. The reaction was stirred at 65° C. for 5-6 hours. LCMS indicated reaction completed (M+Na=435). The reaction was quenched with water (250 mL) and extracted with ethyl acetate (2×250 mL). The combined ethyl acetate solution was washed with water (250 mL, layer separation was slow, 100 mL of brine was added to improve the separation), dried over sodium sulfate, and concentrated to give 49.7 g crude brown solid. Crude yield is 112%. LCMS for $C_{12}H_8BrFN_8O_3Na$ (M+Na)$^+$: m/z=433.0, 435.0. $^1$H NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.7 Hz, 1H), 3.54 (t, J=5.3 Hz, 2H), 3.45 (dd, J=11.1, 5.2 Hz, 2H).

Step I: 3-(4-(2-aminoethylamino)-1,2,5-oxadiazol-3-yl)-4-(3-bromo-4-fluorophenyl)-1,2,4-oxadiazol-5(4H)-one hydroiodide

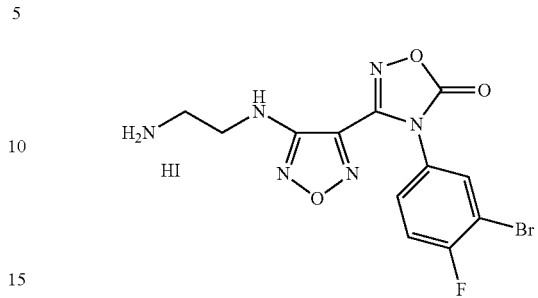

3-(4-(2-azidoethylamino)-1,2,5-oxadiazol-3-yl)-4-(3-bromo-4-fluorophenyl)-1,2,4-oxadiazol-5(4H)-one (80.0 g, 0.194 mol) was mixed with methanol (800 mL). Sodium iodide (175.0 g, 1.17 mol) was added. The reaction was stirred at room temperature for 10 min. Chlorotrimethylsilane (148 mL, 1.17 mol) was dissolved in methanol (100 mL) and added to the reaction over 30 min. The reaction temperature rose 42° C. The reaction was stirred at room temperature for 30 min. LCMS indicated reaction completed (M+H=386). The reaction was quenched with sodium thiosulfate (190.0 g, 1.20 mol) in water (900 mL). A large amount of solid precipitated. The product was collected by filtration (filtration speed was slow), rinsed with water (200 mL), and dried on vacuum overnight. The filter cake was slurried in ethyl acetate (500 mL) for 30 min. The product was filtered (filtration speed is slow) and dried under vacuum over weekend to give 95 g of an off-white solid. LCMS for $C_{12}H_{11}BrFN_6O_3$ (M+H)$^+$: m/z=384.9, 386.9. $^1$H NMR (400 MHz, DMSO-$d_6$): δ 8.12 (m, 4H), 7.76 (m, 1H), 7.58 (t, J=8.7 Hz, 1H), 6.78 (t, J=6.1 Hz, 1H), 3.51 (dd, J=11.8, 6.1 Hz, 2H), 3.02 (m, 2H).

Example 23

Alternate preparation of 4-({2-[(Aminosulfonyl)amino]ethyl}amino)-N-(3-bromo-4-fluorophenyl)-N'-hydroxy-1,2,5-oxadiazole-3-carboximidamide

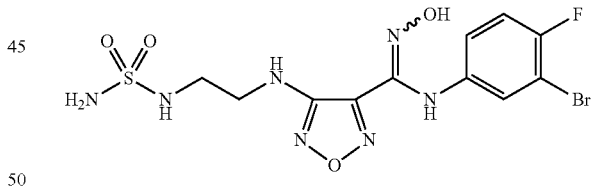

Step A: 4-(3-bromo-4-fluorophenyl)-3-(4-(2-hydroxyethylamino)-1,2,5-oxadiazol-3-yl)-1,2,4-oxadiazol-5(4H)-one

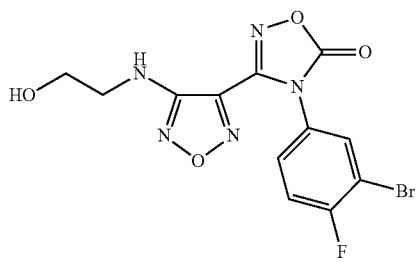

To a solution of 4-(3-bromo-4-fluorophenyl)-3-(4-(2-methoxyethylamino)-1,2,5-oxadiazol-3-yl)-1,2,4-oxadiazol-5(4H)-one (can be prepared according to Example 1, steps A-G; 1232 g, 3.08 mol) in dichloromethane (12 L) stirring in a 22 L flask at 0° C. was added boron tribromide (354 mL, 3.67 mL) dropwise at a rate so that the temperature did not exceed 10° C. After stirring on ice for 1 h, a solution of saturated aqueous sodium bicarbonate (2 L) was carefully added at a rate so that the temperature did not exceed 20° C. (addition time 10 min). The resulting mixture was transferred to a 50 L separatory funnel, diluted with water (10 L), and the pH of the aqueous layer adjusted from 1 to 8 using solid sodium bicarbonate. The layers were separated, and the organic layer was washed with water (10 L), and the solvents removed in vacuo to afford a tan solid (24 mol processed in multiple runs, 9.54 kg, quant. yield). The material was slurried in 4 volumes of 7:1 heptane:ethyl acetate (4×22 L flasks), filtered, and dried to furnish the title compound as a tan solid (8679 g, 94%). The product was a mixture of the hydroxy- and the corresponding bromo-species.

Step B: 2-(4-(4-(3-bromo-4-fluorophenyl)-5-oxo-4,5-dihydro-1,2,4-oxadiazol-3-yl)-1,2,5-oxadiazol-3-ylamino)ethyl methanesulfonate

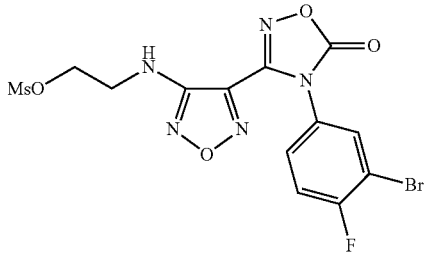 [SMILES: CS(=O)(=O)OCCNc1nonc1-c1noc(=O)n1-c1ccc(F)c(Br)c1]

To a solution of 4-(3-bromo-4-fluorophenyl)-3-{4-[(2-hydroxyethyl)amino]-1,2,5-oxadiazol-3-yl}-1,2,4-oxadiazol-5(4H)-one (1.5 kg, 3.9 mol, containing also some of the corresponding bromo-compound) in ethyl acetate (12 L) was added methanesulfonyl chloride (185 mL, 2.4 mol) dropwise over 1 h at room temperature. Triethylamine (325 mL, 2.3 mol) was added dropwise over 45 min, during which time the reaction temperature increased to 35° C. After 2 h, the reaction mixture was washed with water (5 L), brine (1 L), dried over sodium sulfate, combined with 3 more reactions of the same size, and the solvents removed in vacuo to afford the desired product (7600 g, quantitative yield, containing also some of the corresponding bromo-compound, Caution: irritating dust!) as a tan solid. LCMS for $C_{13}H_{11}BrFN_5O_6SNa$ (M+Na)$^+$: m/z=485.9, 487.9. $^1$H NMR (400 MHz, DMSO-$d_6$): δ 8.08 (dd, J=6.2, 2.5 Hz, 1H), 7.72 (m, 1H), 7.58 (t, J=8.7 Hz, 1H), 6.75 (t, J=5.9 Hz, 1H), 4.36 (t, J=5.3 Hz, 2H), 3.58 (dd, J=11.2, 5.6 Hz, 2H), 3.18 (s, 3H).

Step C: 3-(4-(2-azidoethylamino)-1,2,5-oxadiazol-3-yl)-4-(3-bromo-4-fluorophenyl)-1,2,4-oxadiazol-5(4H)-one

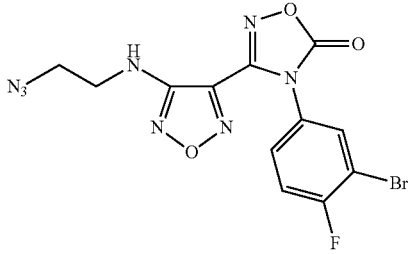 [SMILES: [N-]=[N+]=NCCNc1nonc1-c1noc(=O)n1-c1ccc(F)c(Br)c1]

To a solution of 2-({4-[4-(3-bromo-4-fluorophenyl)-5-oxo-4,5-dihydro-1,2,4-oxadiazol-3-yl]-1,2,5-oxadiazol-3-yl}amino)ethyl methanesulfonate (2.13 kg, 4.6 mol, containing also some of the corresponding bromo-compound) in dimethylformamide (4 L) stirring in a 22 L flask was added sodium azide (380 g, 5.84 mol). The reaction was heated at 50° C. for 6 h, poured into ice/water (8 L), and extracted with 1:1 ethyl acetate:heptane (20 L). The organic layer was washed with water (5 L) and brine (5 L), and the solvents removed in vacuo to afford the desired product (1464 g, 77%) as a tan solid. LCMS for $C_{12}H_8BrFN_8O_3Na$ (M+Na)$^+$: m/z=433.0, 435.0. $^1$H NMR (DMSO-$d_6$, 400 MHz): δ 8.08 (dd, J=6.2, 2.5 Hz, 1H), 7.72 (m, 1H), 7.58 (t, J=8.7 Hz, 1H), 6.75 (t, J=5.7 Hz, 1H), 3.54 (t, J=5.3 Hz, 2H), 3.45 (dd, J=11.1, 5.2 Hz, 2H).

Step D: 3-{4-[(2-Aminoethyl)amino]-1,2,5-oxadiazol-3-yl}-4-(3-bromo-4-fluorophenyl)-1,2,4-oxadiazol-5(4H)-one hydrochloride

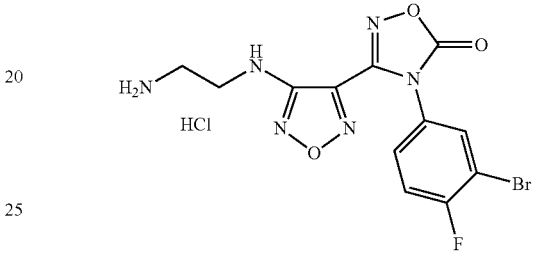

Step D, Part 1: tert-Butyl 2-(4-(4-(3-bromo-4-fluorophenyl)-5-oxo-4,5-dihydro-1,2,4-oxadiazol-3-yl)-1,2,5-oxadiazol-3-ylamino)ethylcarbamate

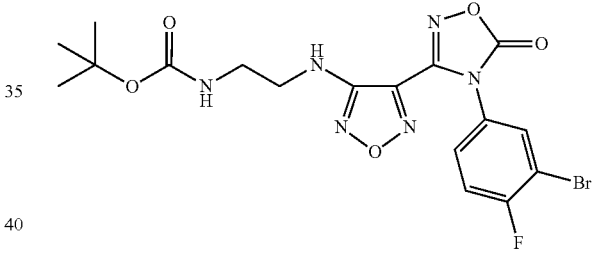

Sodium iodide (1080 g, 7.2 mol) was added to 3-{4-[(2-azidoethyl)amino]-1,2,5-oxadiazol-3-yl}-4-(3-bromo-4-fluorophenyl)-1,2,4-oxadiazol-5(4H)-one (500 g, 1.22 mol) in methanol (6 L). The mixture was allowed to stir for 30 min during which time a mild exotherm was observed. Chlorotrimethylsilane (930 mL, 7.33 mol) was added as a solution in methanol (1 L) dropwise at a rate so that the temperature did not exceed 35° C., and the reaction was allowed to stir for 3.5 h at ambient temperature. The reaction was neutralized with 33 wt % solution of sodium thiosulfate pentahydrate in water (~1.5 L), diluted with water (4 L), and the pH adjusted to 9 carefully with solid potassium carbonate (250 g—added in small portions: watch foaming). Di-tert-butyl dicarbonate (318 g, 1.45 mol) was added and the reaction was allowed to stir at room temperature. Additional potassium carbonate (200 g) was added in 50 g portions over 4 h to ensure that the pH was still at or above 9. After stirring at room temperature overnight, the solid was filtered, triturated with water (2 L), and then MTBE (1.5 L). A total of 11 runs were performed (5.5 kg, 13.38 mol). The combined solids were triturated with 1:1 THF:dichloromethane (24 L, 4 runs in a 20 L rotary evaporator flask, 50° C., 1 h), filtered, and washed with dichloromethane (3 L each run) to afford an off-white solid. The crude material was dissolved at 55° C. tetrahydrofuran (5 mL/g), treated with decolorizing carbon (2 wt %) and silica gel (2 wt %), and filtered hot through celite to afford the product as an off-white solid (5122 g). The combined MTBE, THF, and dichloromethane filtrates were concentrated in vacuo and chromatographed (2 kg silica gel, heptane with a 0-100% ethyl acetate gradient, 30 L) to afford more product (262 g). The combined solids of tert-butyl 2-(4-(4-(3-bromo-4-fluorophenyl)-5-oxo-4,5-dihydro-1,2,4-oxadiazol-3-yl)-1,2,5-oxadiazol-3-ylamino)ethylcarbamate were dried to a constant weight in a convection oven (5385 g, 83%).

Step D, Part 2: 3-{4-[(2-Aminoethyl)amino]-1,2,5-oxadiazol-3-yl}-4-(3-bromo-4-fluorophenyl)-1,2,4-oxadiazol-5(4H)-one hydrochloride Method A:
In a 22 L flask was charged hydrogen chloride (4 N solution in 1,4-dioxane, 4 L, 16 mol). tert-Butyl [2-({4-[4-(3-bromo-4-fluorophenyl)-5-oxo-4,5-dihydro-1,2,4-oxadiazol-3-yl]-1,2,5-oxadiazol-3-yl}amino)ethyl]carbamate (2315 g, 4.77 mol) was added as a solid in portions over 10 min. The slurry was stirred at room temperature and gradually became a thick paste that could not be stirred. After sitting overnight at room temperature, the paste was slurried in ethyl acetate (10 L), filtered, re-slurried in ethyl acetate (5 L), filtered, and dried to a constant weight to afford the desired product as a white solid (combined with other runs, 5 kg starting material charged, 4113 g, 95%). LCMS for $C_{12}H_{11}BrFN_6O_3$ (M+H)$^+$: m/z=384.9, 386.9. $^1$H NMR (400 MHz, DMSO-$d_6$): δ 8.12 (m, 4H), 7.76 (m, 1H), 7.58 (t, J=8.7 Hz, 1H), 6.78 (t, J=6.1 Hz, 1H), 3.51 (dd, J=11.8, 6.1 Hz, 2H), 3.02 (m, 2H).

Method B:
tert-Butyl [2-({4-[4-(3-bromo-4-fluorophenyl)-5-oxo-4,5-dihydro-1,2,4-oxadiazol-3-yl]-1,2,5-oxadiazol-3-yl}amino)ethyl]carbamate (5000 g) was added to a mixture of isopropanol (20 L) and 4 N HCl in 1,4-dioxane (10 L) at room temperature. The batch was heated to 40-45° C. and held for 1 h. Ethyl acetate was added to the batch at 40-45° C. and held for 2.5 h. Upon reaction completion, as indicated by HPLC, heptane (10 L) was added to the batch. The batch was cooled to 25° C. The product was isolated by filtration and the wet cake was washed with ethyl acetate (3×5.0 L). The product was dried in a vacuum, oven at 20° C. to give 4344 g (93.4% yield) of the title compound. LC-MS, $^1$H and $^{13}$C NMR, and HPLC data of this lot were identical to those of the product prepared by Method A.

Step E: tert-Butyl({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate

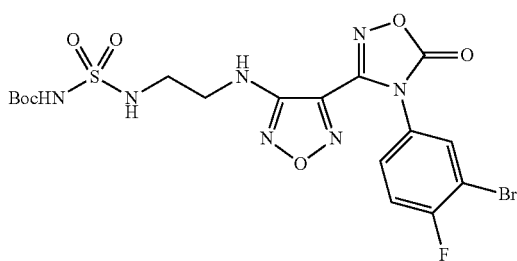 [SMILES: CC(C)(C)OC(=O)NS(=O)(=O)NCCNc1nonc1-c1noc(=O)n1-c1ccc(F)c(Br)c1]

A 5 L round bottom flask was charged with chlorosulfonyl isocyanate [Aldrich, product #142662] (149 mL, 1.72 mol) and dichloromethane (1.5 L) and cooled using an ice bath to 2° C. tert-Butanol (162 mL, 1.73 mol) in dichloromethane (200 mL) was added dropwise at a rate so that the temperature did not exceed 10° C. The resulting solution was stirred at room temperature for 30-60 min to provide tert-butyl [chlorosulfonyl]carbamate.

A 22 L flask was charged with 3-{4-[(2-aminoethyl)amino]-1,2,5-oxadiazol-3-yl}-4-(3-bromo-4-fluorophenyl)-1,2,4-oxadiazol-5 (4H)-one hydrochloride (661 g, 1.57 mol) and 8.5 L dichloromethane. After cooling to −15° C. with an ice/salt bath, the solution of tert-butyl [chlorosulfonyl]carbamate (prepared as above) was added at a rate so that the temperature did not exceed −10° C. (addition time 7 min). After stirring for 10 min, triethylamine (1085 mL, 7.78 mol) was added at a rate so that the temperature did not exceed −5° C. (addition time 10 min). The cold bath was removed, the reaction was allowed to warm to 10° C., split into two portions, and neutralized with 10% conc HCl (4.5 L each portion). Each portion was transferred to a 50 L separatory funnel and diluted with ethyl acetate to completely dissolve the white solid (~25 L). The layers were separated, and the organic layer was washed with water (5 L), brine (5 L), and the solvents removed in vacuo to afford an off-white solid. The solid was triturated with MTBE (2×1.5 L) and dried to a constant weight to afford a white solid. A total of 4113 g starting material was processed in this manner (5409 g, 98%). $^1$H NMR (400 MHz, DMSO-$d_6$): δ 10.90 (s, 1H), 8.08 (dd, J=6.2, 2.5 Hz, 1H), 7.72 (m, 1H), 7.59 (t, J=8.6 Hz, 1H), 6.58 (t, J=5.7 Hz, 1H), 3.38 (dd, J=12.7, 6.2 Hz, 2H), 3.10 (dd, J=12.1, 5.9 Hz, 2H), 1.41 (s, 9H).

Step F: N-[2-({4-[4-(3-Bromo-4-fluorophenyl)-5-oxo-4,5-dihydro-1,2,4-oxadiazol-3-yl]-1,2,5-oxadiazol-3-yl}amino)ethyl]sulfamide

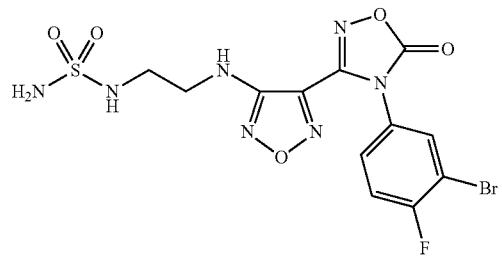 [SMILES: NS(=O)(=O)NCCNc1nonc1-c1noc(=O)n1-c1ccc(F)c(Br)c1]

Method A: Using Trifluoroacetic Acid
To a 22 L flask containing 98:2 trifluoroacetic acid:water (8.9 L) was added tert-butyl({[2-({4-[4-(3-bromo-4-fluorophenyl)-5-oxo-4,5-dihydro-1,2,4-oxadiazol-3-yl]-1,2,5-oxadiazol-3-yl}amino)ethyl]amino}sulfonyl)carbamate (1931 g, 3.42 mol) in portions over 10 minutes. The resulting mixture was stirred at room temperature for 1.5 h, the solvents removed in vacuo, and chased with dichloromethane (2 L). The resulting solid was treated a second time with fresh 98:2 trifluoroacetic acid:water (8.9 L), heated for 1 h at 40-50° C., the solvents removed in vacuo, and chased with dichloromethane (3×2 L). The resulting white solid was dried in a vacuum drying oven at 50° C. overnight. A total of 5409 g was processed in this manner (4990 g, quant. yield). LCMS for $C_{12}H_{12}BrFN_7O_5S$ (M+H)$^+$: m/z=463.9, 465.9. $^1$H NMR (400 MHz, DMSO-$d_6$): δ 8.08 (dd, J=6.2, 2.5 Hz, 1H), 7.72 (m, 1H), 7.59 (t, J=8.7 Hz, 1H), 6.67 (t, J=5.9 Hz, 1H), 6.52 (t, J=6.0 Hz, 1H), 3.38 (dd, J=12.7, 6.3 Hz, 2H), 3.11 (dd, J=12.3, 6.3 Hz).

Method B: Using Hydrochloric Acid
To solution of tert-butyl({[2-({4-[4-(3-bromo-4-fluorophenyl)-5-oxo-4,5-dihydro-1,2,4-oxadiazol-3-yl]-1,2,5- oxadiazol-3-yl}amino)ethyl]amino}sulfonyl)carbamate (4500 g) in isopropanol (9 L) was added 4 N HCl in dioxane (8.0 L). The reaction mixture was heated to 40-45° C. and was held at this temperature for about 5 h. Upon completion of reaction (as indicated by HPLC analysis), heptane (72 L) was added to the reaction mixture. The resultant mixture was heated to 68° C. and held at this temperature for 1 h. The batch was allowed to cool to about 23° C. The solid product was collected by filtration. The wet cake was washed with a mixture of heptane (16 L) and isopropanol (1.2 L) and dried under suction on a filter funnel. The crude product was dissolved in ethyl acetate (10.8 L) at about 43° C. Heptane (32.4 L) was added to the ethyl acetate solution over 15 min. The batch was heated to 70° C. and held at this temperature for 1 h. The batch was cooled to 21° C. and solid product was collected by filtration. The wet cake was washed with heptane (14.4 L) and dried under suction on the filter funnel. Yield of product was 3034 g. LC-MS, $^1$H and $^{13}$C NMR, and HPLC data of this lot were identical to those of the product prepared by Method A.

Step G: (Z)-4-({2-[(Aminosulfonyl)amino] ethyl}amino)-N-(3-bromo-4-fluorophenyl)-N'-hydroxy-1,2,5-oxadiazole-3-carboximidamide Method A:

To a crude mixture of N-[2-({4-[4-(3-bromo-4-fluorophenyl)-5-oxo-4,5-dihydro-1,2,4-oxadiazol-3-yl]-1,2,5-oxadiazol-3-yl}amino)ethyl]sulfamide (2.4 mol) containing residual amounts of trifluoroacetic acid stirring in a 22 L flask was added THF (5 L). The resulting solution was cooled to 0° C. using an ice bath and 2 N NaOH (4 L) was added at a rate so that the temperature did not exceed 10° C. After stirring at ambient temperature for 3 h (LCMS indicated no starting material remained), the pH was adjusted to 3-4 with concentrated HCl (~500 mL). The THF was removed in vacuo, and the resulting mixture was extracted with ethyl acetate (15 L). The organic layer was washed with water (5 L), brine (5 L), and the solvents removed in vacuo to afford a solid. The solid was triturated with MTBE (2×2 L), combined with three other reactions of the same size, and dried overnight in a convection oven to afford a white solid (3535 g). The solid was recrystallized (3×22 L flasks, 2:1 deionized ultra-filtered water: ethanol, 14.1 L each flask) and dried in a 50° C. convection oven to a constant weight to furnish the title compound as an off-white solid (3290 g, 78%). LCMS for $C_{11}H_{14}BrFN_7O_4S$ (M+H)$^+$: m/z=437.9, 439.9, $^1$H NMR (400 MHz, DMSO-d$_6$): δ 11.51 (s, 1H), 8.90 (s, 1H), 7.17 (t, J=8.8 Hz, 1H), 7.11 (dd, J=6.1, 2.7 Hz, 1H), 6.76 (m, 1H), 6.71 (t, J=6.0 Hz, 1H), 6.59 (s, 2H), 6.23 (t, J=6.1 Hz, 1H), 3.35 (dd, J=10.9, 7.0 Hz, 2H), 3.10 (dd, J=12.1, 6.2 Hz, 2H). X-ray crystallographic analysis determined that the title compound adopts a Z-configuration (Z-isomer) with respect to the carbon-nitrogen double bond (C=N) of oxime functionality.

Method B:

N-[2-({4-[4-(3-bromo-4-fluorophenyl)-5-oxo-4,5-dihydro-1,2,4-oxadiazol-3-yl]-1,2,5-oxadiazol-3-yl}amino) ethyl]sulfamide (1500 g) was added to THF (6.0 L) and the batch was cooled to 2° C. Trifluoroacetic acid (0.006 L) was added to the batch at 2° C. followed by addition of aqueous sodium hydroxide solution (384 g of solid NaOH in 4.8 L of water) at 0-2° C. The batch was warmed up to about 16° C. and held for 5 h. Upon completion of reaction, as indicated by HPLC, concentrated hydrochloric acid (0.7 L) was added to adjust the pH of the batch to 3-4. About 4 L of solvent was removed from the batch by distillation under reduced pressure. The batch was added to ethyl acetate (18.0 L) and the biphasic mixture was stirred for 15 min. The organic layer was washed with water (6.0 L) and brine (6.0 L) sequentially. The organic solution was dried over anhydrous magnesium sulfate. Magnesium sulfate was filtered and the filtrate was evaporated to dryness under reduced pressure. To the resultant solid, MTBE (3.0 L) was added and the slurry was stirred for 15 min. The solid product was isolated by filtration. The filter cake was washed with MTBE (1.2 L) and heptane (1.2 L) sequentially. The solid was dried on the filter funnel under suction to give 1416 g (87.9%) of the product. The product (2440 g, obtained in two batches) was further purified by re-slurrying in MTBE (9.6 L) at 17° C. for 2 h. The batch was cooled to 6° C. for 30 min. The solid product was collected by filtration and the wet cake was washed with MTBE (3.6 L) and heptane (1.2 L) sequentially. The product was dried in a vacuum oven at 20° C. to give 1962 g of the title compound in 81.7% yield. LC-MS, $^1$H and $^{13}$C NMR, and HPLC data of this lot were identical to those of the product prepared by Method A.

Example 24

Compound Data

Select physical and biological activity data for the compounds of Example 1-19 are summarized in Table 2 below. IC$_{50}$ data are from the assay provided in Example A.

TABLE 2

| Ex. No. | R$_1$ | R$_2$ | R$_3$ | n | IDO IC$_{50}$ (nM) | MS [M + H] |
|---|---|---|---|---|---|---|
| 1 | NH$_2$ | Br | F | 1 | <200 | 437.9, 439.9 |
| 2 | Me | Br | F | 1 | <200 | 437.0, 439.0 |
| 3 | NH$_2$ | Br | F | 2 | <100 | 451.8, 453.9 |
| 4 | Me | Br | F | 2 | <100 | 451.0, 453.0 |
| 5 | NH$_2$ | Cl | F | 1 | <200 | 394.0 |
| 6 | Me | Cl | F | 1 | <200 | 393.0 |
| 7 | NH$_2$ | Cl | F | 2 | <200 | 408.1 |
| 8 | Me | Cl | F | 2 | <200 | 407.1 |
| 9 | NH$_2$ | CF$_3$ | F | 1 | <100 | 428.0 |
| 10 | Me | CF$_3$ | F | 1 | <100 | 427.0 |
| 11 | NH$_2$ | CF$_3$ | F | 2 | <100 | 442.0 |
| 12 | Me | CF$_3$ | F | 2 | <100 | 441.1 |
| 13 | NH$_2$ | CF$_3$ | H | 1 | <500 | 410.0 |
| 14 | Me | CF$_3$ | H | 1 | <200 | 409.1 |
| 15 | NH$_2$ | CF$_3$ | H | 2 | <200 | 424.0 |
| 16 | Me | CF$_3$ | H | 2 | <200 | 423.1 |
| 17 | Me | CH$_3$ | F | 1 | <500 | 373.1 |
| 18 | NH$_2$ | CN | F | 1 | <750 | 385.0 |
| 19 | Me | CN | F | 1 | <500 | 406.0* |

*[M + Na]

Example 25

Compound Data

IDO IC$_{50}$ data (see Example A) for the compounds of Examples 20 and 21 is provided below in Table 3.

TABLE 3

| Ex. No. | IDO IC$_{50}$ (nM) |
|---|---|
| 20 | <500 |
| 21 | <750 |

Example 26

NMR Data $^1$H NMR data (Varian Inova 500 spectrometer, a Mercury 400 spectrometer, or a Varian (or Mercury) 300 spectrometer) for the compounds of Examples 1-21 is provided below in Table 4.

TABLE 4

| Ex. No. | Solvent | MHz | $^1$H NMR Spectra |
|---|---|---|---|
| 1 | DMSO-d$_6$ | 400 | δ 11.5 (s, 1 H), 8.89 (s, 1 H), 7.17 (dd, J = 8.8, 8.6 Hz, 1 H), 7.09 (dd, J = 6.1, 2.7 Hz, 1 H), 6.76-6.72 (m, 1 H), 6.56 (dd, J = 6.1, 6.1 Hz, 1 H), 6.51 (s, 2 H), 6.17 (dd, J = 5.9, 5.9 Hz, 1 H), 3.27-3.21 (m, 2 H), 2.94-2.88 (m, 2 H), 1.78-1.71 (m, 2 H) |
| 2 | DMSO-d$_6$ | 400 | δ 11.49 (s, 1H), 8.90 (s, 1H), 7.17 (m, 2H), 7.09 (dd, J = 6.3, 2.5 Hz, 1H), 6.26 (t, J = 6.1 Hz, 1H), 3.33 (m, 2H), 3.13 (q, J = 6.0 Hz, 2H), 2.89 (s, 3H) |
| 3 | DMSO-d$_6$ | 400 | δ 11.5 (s, 1 H), 8.89 (s, 1 H), 7.17 (dd, J = 8.8, 8.6 Hz, 1 H), 7.09 (dd, J = 6.1, 2.7 Hz, 1 H), 6.76-6.72 (m, 1 H), 6.56 (dd, J = 6.1, 6.1 Hz, 1 H), 6.51 (s, 2 H), 6.17 (dd, J = 5.9, 5.9 Hz, 1 H), 3.27-3.21 (m, 2 H), 2.94-2.88 (m, 2 H), 1.78-1.71 (m, 2 H) |
| 4 | CD$_3$OD | 400 | δ 7.12 (dd, J = 5.9, 2.4 Hz, 1H), 7.05 (t, J = 8.7 Hz, 1H), 6.83 (m, 1H), 3.39 (t, J = 6.8 Hz, 2H), 3.14 (t, J = 6.6 Hz, 2H), 2.94 (s, 3H), 1.87 (m, 2H) |
| 5 | DMSO-d$_6$ | 400 | δ 7.96 (dd, J = 6.8, 2.1 Hz, 0.05 H), 7.32-7.29 (m, 0.1 H), 7.18 (dd, J = 9.1, 9.1 Hz, 0.95 H), 6.93 (dd, J = 6.4, 2.7 Hz, 0.95 H), 6.71-6.66 (m, 0.95 H), 6.33 (br s, 1 H), 3.35-3.27 (m, 2 H), 3.10-3.06 (m, 2 H) |
| 6 | DMSO-d$_6$ | 400 | δ 11.50 (s, 1H), 8.91 (s, 1H), 7.19 (m, 2H), 6.96 (dd, J = 6.7, 2.5 Hz, 1H), 6.71 (m, 1H), 6.26 (t, J = 6.4 Hz, 1H), 3.32 (m, 2H), 3.13 (q, J = 5.8 Hz, 2H), 2.89 (s, 3H) |
| 7 | DMSO-d$_6$ | 400 | δ 8.90 (s, 1 H), 7.20 (dd, J = 9.2, 9.0 Hz, 1 H), 6.96 (dd, J = 6.4, 2.7 Hz, 1 H), 6.72-6.69 (m, 1 H), 6.55 (t, J = 6.0 Hz, 1 H), 6.51 (s, 2 H), 6.16 (t, J = 5.9 Hz, 1 H), 3.28-3.21 (m, 2 H), 2.93-2.87 (m, 2H), 1.76-1.72 (m, 2 H) |
| 8 | CD$_3$OD | 300 | δ 7.06 (t, J = 8.9 Hz, 1H), 6.98 (m, 1H), 6.80 (m, 1H), 3.73 (m, 2H), 3.28 (m, 2H), 2.94 (s, 3H), 1.28 (m, 2H) |
| 9 | DMSO-d$_6$ | 400 | δ 11.60 (s, 1H), 9.06 (s, 1H), 7.30 (t, J = 10.1 Hz, 1H), 7.14 (dd, J = 6.1, 2.7 Hz, 1H), 7.03 (m, 1H), 6.71 (t, J = 5.3 Hz, 1H), 6.58 (s, 2H), 6.23 (t, J = 6.2 Hz, 1H), 3.36 (q, J = 6.5 Hz, 2H), 3.08 (m, 2H) |
| 10 | DMSO-d$_6$ | 400 | δ 11.60 (s, 1H), 9.07 (s, 1H), 7.30 (t, J = 10.1 Hz, 1H), 7.18 (t, J = 6.0 Hz, 1H), 7.13 (dd, J = 6.0, 2.7 Hz, 1H), 7.03 (m, 1H), 6.27 (t, J = 6.3 Hz, 1H), 3.32 (m, 2H), 3.13 (q, J = 6.0 Hz, 2H), 2.89 (s, 3H) |
| 11 | DMSO-d$_6$ | 300 | δ 11.6 (s, 1 H), 9.08 (s, 1 H), 7.31 (dd, J = 10.0, 9.4 Hz, 1 H), 7.13 (dd, J = 6.4, 2.9 Hz, 1 H), 7.05-6.99 (m, 1 H), 6.58 (t, J = 6.0 Hz, 1 H), 6.52 (s, 2 H), 6.17 (t, J = 5.9 Hz, 1 H), 3.28-3.21 (m, 2 H), 2.94-2.87 (m, 2 H), 1.79-1.72 (m, 2 H) |
| 12 | DMSO-d$_6$ | 400 | δ 11.6 (s, 1 H), 9.07 (s, 1 H), 7.30 (dd, J = 10.0, 9.6 Hz, 1 H), 7.13 (dd, J = 6.2, 2.5 Hz, 1 H), 7.05-7.02 (m, 2 H), 6.19 (t, J = 5.8 Hz, 1 H), 3.27-3.21 (m, 2 H), 2.99-2.94 (m, 2 H), 2.87 (s, 3 H), 1.76-1.72 (m, 2 H) |
| 13 | CD$_3$OD | 400 | δ 7.36 (t, J = 7.8 Hz, 1H), 7.23 (d, J = 7.8 Hz, 1H), 7.10 (s, 1H), 7.03 (d, J = 7.8 Hz, 1H), 3.48 (m, 2H), 3.29 (m, 2H) |
| 14 | DMSO-d$_6$ | 500 | δ 11.63 (s, 1H), 9.08 (s, 1H), 7.39 (t, J = 7.6 Hz, 1H), 7.21 (m, 2H), 7.10 (s, 1H), 6.99 (d, J = 8.1 Hz, 1H), 6.28 (t, J = 5.4 Hz, 1H), 3.36 (q, J = 5.8 Hz, 2H), 3.17 (q, J = 5.8 Hz, 2H), 2.91 (s, 3H) |
| 15 | DMSO-d$_6$ | 400 | δ 11.6 (s, 1 H), 9.12 (s, 1 H), 7.37 (dd, J = 8.0, 8.0 Hz, 1 H), 7.21-7.18 (m, 1 H), 7.07 (s, 1 H), 6.95 (d, J = 10.0 Hz, 1 H), 6.52 (br s, 3 H), 6.17 (t, J = 6.0 Hz, 1 H), 3.28-3.22 (m, 2 H), 2.93-2.89 (m, 2 H), 1.77-1.73 (m, 2 H) |
| 16 | DMSO-d$_6$ | 400 | δ 11.6 (s, 1 H), 9.11 (s, 1 H), 7.37 (dd, J = 8.0, 8.0 Hz, 1 H), 7.20 (d, J = 7.8 Hz, 1 H), 7.07-7.01 (m, 2 H), 6.96 (d, J = 8.0 Hz, 1 H), 6.20 (t, J = 5.9 Hz, 1 H), 3.27-3.22 (m, 2 H), 2.99-2.94 (m, 2 H), 2.87 (s, 3 H), 1.78-1.71 (m, 2 H) |
| 17 | DMSO-d$_6$ | 400 | δ 11.25 (s, 1H), 8.61 (s, 1H), 7.18 (m, 1H), 6.91 (m, 1H), 6.72 (m, 1H), 6.58 (m, 1H), 6.24 (s, 2H), 3.32 (m, 2H), 3.11 (m, 2H), 2.89 (s, 3H), 2.05 (s, 3H). |
| 18 | DMSO-d$_6$ | 400 | δ 11.65 (s, 1H), 9.08 (s, 1H), 7.34 (t, J = 9.1 Hz, 1H), 7.22 (dd, J = 5.4, 2.8 Hz, 1H), 7.13 (m, 1H), 6.70 (t, J = 5.9 Hz, 1H), 6.59 (s, 2H), 6.20 (t, J = 6.1 Hz, 1H), 3.34 (m, 2H), 3.09 (m, 2H) |
| 19 | DMSO-d$_6$ | 400 | δ 11.65 (s, 1H), 9.08 (s, 1H), 7.35 (m, 1H), 7.18 (m, 3H), 6.56 (m, 1H), 6.23 (m, 1H), 6.24 (s, 2H), 3.32 (m, 2H), 3.14 (m, 2H), 2.89 (s, 3H) |

TABLE 4-continued

| Ex. No. | Solvent | MHz | $^1$H NMR Spectra |
|---|---|---|---|
| 20 | DMSO-d$_6$ | 400 | δ 10.87 (s, 1 H), 7.75 (s, 1 H), 6.83 (t, J = 7.3 Hz, 1 H), 6.68 (t, J = 6.0 Hz, 1 H), 6.56 (s, 2 H), 6.30 (t, J = 6.0 Hz, 1 H), 6.23 (s, 1 H), 4.56 (d, J = 7.0 Hz, 2 H), 3.32 (q, J = 6.3 Hz, 2 H), 3.07 (q, J = 6.3 Hz, 2 H) |
| 21 | DMSO-d$_6$ | 400 | δ 10.88 (s, 1 H), 7.77 (s, 1 H), 6.83 (t, J = 6.8 Hz, 1 H), 6.68 (t, J = 5.9 Hz, 1 H), 6.56 (s, 2 H), 6.30 (t, J = 5.9 Hz, 1 H), 6.22 (s, 1 H), 4.55 (d, 2 H), 3.32 (q, J = 6.3 Hz, 2 H), 3.06 (q, J = 6.3 Hz, 2 H) |

Example A

Human Indoleamine 2,3-Dioxygenasae (IDO) Enzyme Assay

Human indoleamine 2,3-dioxygenasae (IDO) with an N-terminal His tag was expressed in *E. coli* and purified to homogeneity. IDO catalyzes the oxidative cleavage of the pyrrole ring of the indole nucleus of tryptophan to yield N'-formylkynurenine. The assays were performed at room temperature as described in the literature using 95 nM IDO and 2 mM D-Trp in the presence of 20 mM ascorbate, 5 μM methylene blue and 0.2 mg/mL catalase in 50 mM potassium phosphate buffer (pH 6.5). The initial reaction rates were recorded by continuously following the absorbance increase at 321 nm due to the formation of N'-formylkynurenine (See: Sono, M., et al., 1980, *J. Biol. Chem.* 255, 1339-1345).

Example B

Determination of Inhibitor Activity in Hela Cell-Based Indoleamine 2,3-Dioxygenase (IDO)/Kynurenine Assay HeLa cells (#CCL-2) were obtained from the American Type Tissue Culture Collection (ATCC, Manassas, Va.) and routinely maintained in minimum essential medium (eagle) with 2 mM L-glutamine and Earle's BSS adjusted to contain 1.5 g/L sodium bicarbonate, 0.1 mM non-essential amino acids, 1 mM sodium pyruvate and 10% fetal bovine serum (all from Invitrogen). Cells were kept at 37° C. in a humidified incubator supplied with 5% CO$_2$. The assay was performed as follows: HeLa cells were seeded in a 96 well culture plate at a density of 5×10$^3$ per well and grown overnight. On the next day, IFN-γ (50 ng/mL final concentration) and serial dilutions of compounds (in total volume of 200 μL culture medium) were added into cells. After 48 hours of incubation, 140 μL of the supernatant per well was transferred to a new 96 well plate. 10 μL of 6.1 N trichloroacetic acid (#T0699, Sigma) was mixed into each well and incubated at 50° C. for 30 min to hydrolyze N-formylkynurenine produced by indoleamine 2,3-dioxygenase to kynurenine. The reaction mixture was then centrifuged for 10 min at 2500 rpm to remove sediments. 100 μL of the supernatant per well was transferred to another 96 well plate and mixed with 100 μl of 2% (w/v) p-dimethylaminobenzaldehyde (#15647-7, Sigma-Aldrich) in acetic acid. The yellow color derived from Kynurenine was measured at 480 nm using a SPECTRAmax 250 microplate reader (Molecular Devices). L-kynurenine (#K8625, Sigma) was used as standard. The standards (240, 120, 60, 30, 15, 7.5, 3.75, 1.87 μM) were prepared in 100 μL culture media and mixed with equal volume of 2% (w/v) p-dimethylaminobenzaldehyde. The percent inhibition at individual concentrations was determined and the average values of duplicates were obtained. The data was analyzed by using nonlinear regression to generate IC$_{50}$ values (Prism Graphpad). See: Takikawa O, et al., 1988, *J. Biol, Chem.*, 263 (4): 2041-8.

Example C

Determination of Effect of IDO Inhibitors on T Cell Proliferation that is Suppressed by IDO-Expressing Dendritic Cells Monocytes were collected from human peripheral mononuclear cells by leukophoresis. Monocytes were then seeded at a density of 1×10$^6$ cells/well in a 96 well plate, using RPMI 1640 medium supplemented with 10% fetal bovine serum and 2 mM L-glutamine (all from Invitrogen). Adherent cells were retained on the plate after overnight culture at 37° C. Adherent monocytes were then stimulated for 5-7 days with 100 ng/ml GM-CSF (#300-03, PeproTech) and 250 ng/ml IL-4 (#200-04, PeproTech), followed by activation with 5 μg/mL LPS from *Salmonella typhimurium* (#437650, Sigma) and 50 ng/mL IFN-γ (#285-IF, R&D Systems) for additional 2 days to induce dendritic cell maturation.

After dendritic cell activation, the medium was replaced with completed RPMI 1640 supplemented with 100-200 U/mL IL-2 (#CYT-209, ProSpec-Tany TechnoGene) and 100 ng/mL anti-CD3 antibody (#555336, PharMingen), T cells (2-3×10$^5$ cells/well), and serial dilutions of IDO compounds. After incubation for 2 more days, T cell proliferation was measured by BrdU incorporation assay, using a colorimetric Cell Proliferation ELISA kit per manufacturer's instruction (#1647229, Roche Molecular Biochemicals). Cells were continuously cultured for 16-18 hrs in presence of 10 μM BrdU labeling solution. Then, the labeling medium was removed, and 200 μL FixDenat per well was added to the cells and incubated for 30 minutes at room temperature. The FixDenat solution was removed and 100 μL/well anti-BrdU-POD antibody conjugate working solution was added. The reaction was carried out for 90 minutes at room temperature. The antibody conjugate was then removed, and cells were rinsed three times with 200 μL/well washing solution. Finally, 100 μL/well of substrate solution was added and the results were obtained using a microplate reader (Spectra Max PLUS, Molecular Devices) during color development. Multiple readings at various time points were obtained to ensure the data was within the linear range. The data was routinely obtained from replicated experiments, and appropriate controls were included. See: Terness P, et al. 2002, *J. Exp. Med.*, 196 (4): 447-57; and Hwu, P, et al. 2000, *J. Immunol.*, 164 (7): 3596-9.

Example D

In Vivo Testing of IDO Inhibitors for Antitumor Activity

In vivo anti-tumor efficacy can be tested using modified tumor allograft/xenograft protocols. For instance, it has been described in the literature that IDO inhibition can syngerize with cytotoxic chemotherapy in immune-competent mice (Muller, A. J., et al. 2005, *Nat. Med.* 11:312-319). This synergy was shown to be dependent on T-cells by comparison of the synergistic effects of an investigational IDO inhibitor in murine tumor xenograft models (e.g. B16 and related variants, CT-26, LLC) grown in immune competent syngenic mice to that observed in syngenic mice treated with neutralizing anti-CD4 antibodies, or the same tumors grown in immune-compromised mice (e.g. nu/nu).

The concept of differential anti-tumor effects in immune-competent versus immune-compromised mice may also permit testing of investigational IDO inhibitors as single agents. For instance, LLC tumors grow well in their syngenic host strain, C57Bl/6. However, if these mice are treated with the IDO inhibitor 1-MT (versus placebo) the formation of tumors is markedly delayed, implying that IDO inhibition was growth inhibitory (Friberg, M., et al. 2002, *Int. J. Cancer* 101:151-155). Following this logic, one can examine the efficacy of IDO inhibition in the LLC xenograft tumor model grown in C57Bl/6 immune competent mice and compare that to the effects of IDO inhibitors on LLC tumor growth in nude or SCID mice (or C57Bl/6 mice treated with antibodies that neutralize T-cell activity). As the effects of relieving the tumor-mediated immune suppressive activity of IDO will likely differ depending on the immunogenic potential of different tumor models, genetic modifications can be made to the tumor cells to increase their immunogenic potential. For instance, expression of GM-CSF in B16.F10 cells increases their immunogenic potential (Dranoff, G., et al. 1993, *Proc. Natl. Acad. Sci., USA,* 90:3539-3543). As such, in some tumor models (e.g. B16.F10) one can generate [poly]clones that express immune stimulatory proteins such as GM-CSF and test the growth inhibitory effects of IDO inhibitors against tumors established from these tumor cells in both immune-competent and -compromised mice.

A third avenue for assessing the efficacy of IDO inhibitors in vivo employs 'pre-immunization' murine tumor allograft/xenograft models. In these models, immune-competent mice are sensitized to a specific tumor antigen or antigens to mimic a therapeutic anti-tumor vaccination. This primes the mice for an anti-tumor response mediated by the immune system when mice are subsequently challenged with murine tumor cell lines (possessing similar tumor antigens to those used for immunization) in xenograft experiments. Expression of IDO has been shown to blunt the anti-tumor response and allow xenografts to grow more rapidly. Importantly, the growth of tumors in this model is inhibited by the IDO inhibitor 1-MT (Uyttenhove, C., et al. 2003, *Nat. Med.* 9:1269-1274). This model is particularly attractive as IDO activity is permissive for P815 tumor growth and specific inhibition of IDO should therefore growth inhibitory.

Lastly, therapeutic immunization may be used to evaluate the impact of IDO inhibitors in vivo. For example, it has been demonstrated using B16-BL6 cells that one can challenge Blk/6 mice with an intravenous injection of tumor cells followed by treatment with a well characterized immunogenic peptide (e.g. TRP-2) expressed by the tumor cells (Ji, et al., 2005, *J. Immunol,* 175: 1456-63). Importantly, immune system modifiers, such as anti-CTL-4 antibody, can improve responses to such therapeutic immunizations. The impact of IDO inhibitors may be evaluated in a similar manner—tumor peptide immunization with or without IDO inhibitor. Efficacy is assess by animal survival (time to morbidity) or by the measurement of tumor metastases to the lungs and/or other organs at defined timepoints.

In any/all of the above mentioned models, it may also be possible to directly and/or indirectly measure the number and/or activity of tumor reactive immune cells. Methods for measuring the number and/or activity of tumor reactive immune cells are well established and can be performed using techniques familiar to those schooled in the art (Current Protocols in Immunology, Vol. 4, Coligan, J. E., et al.; *Immunotherapy of Cancer*, Human Press, 2006, Disis, M. L. and references therein). Conceptually, a reduction in the immune suppressive effects of IDO may result in increased numbers or reactivity of tumor specific immune cells. Further, IDO inhibition may further increase the number or reactivity of tumor reactive immune cells when combined with other therapeutics, for example chemotherapeutics and/or immune modulators (e.g. anti-CTLA4 antibody).

All allograft/xenograft experiments can be performed using standard tumor techniques (reviewed by Corbett, et al., In *Cancer Drug Discovery and Development: Anticancer Drug Development Guide: Preclinical Screening, Clinical Trials, and Approval,* $2^{nd}$ Ed. Teicher, B. A. and Andrews, P. A., Gumana Press Inc.: Totowa, N.J., 2004). The cloning and introduction of genes (e.g. IDO, GM-CSF) into tumor cell lines, can be performed using techniques familiar to those schooled in the art (reviewed in Sambrook, J. and Russel, D., *Molecular Cloning: A laboratory Manual* ($3^{rd}$ edition), Cold Spring Harbor Laboratory Press: Cold Spring Harbor, N.Y., 2001).

Example E

In Vivo Testing of IDO Inhibitors in Human Immunodeficiency Virus-1 (HIV-1) Encephalitis Model 1. Cell Isolation and Viral Infection Monocytes and PBL can be obtained by countercurrent centrifugal elutriation of leukopheresis packs from HIV-1, 2 and hepatitis B seronegative donors. Monocytes are cultivated in suspension culture using Teflon flasks in Dulbecco's Modified Eagle's Medium (DMEM, Sigma-Aldrich) supplemented with 10% heat-inactivated pooled human serum, 1% glutamine, 50 µg/mL gentamicin, 10 µg/mL ciprofloxacin (Sigma), and 1000 U/mL highly purified recombinant human macrophage colony stimulating factor. After seven days in culture, MDM are infected with HIV-$1_{ADA}$ at multiplicity of infection of 0.01.

2. Hu-PBL-NOD/SCID HIVE Mice

Four-wk old male NOD/C.B-17 SCID mice can be purchased (Jackson Laboratory). Animals are maintained in sterile microisolator cages under pathogen-free conditions. All animals are injected intraperitoneally with rat anti-CD122 (0.25 mg/mouse) three days before PBL transplantation and twice with rabbit asialo-GM1 antibodies (0.2 mg/mouse) (Wako) one day before and three days after PBL injection ($20 \times 10^6$ cells/mouse). HIV-$1_{ADA}$-infected MDM ($3 \times 10^5$ cells in 10 µL) are injected intracranially (i.c.) eight days following PBL reconstitution generating hu-PBL-NOD/SCID HIVE mice. Immediately following i.c. injection of HIV-1 infected MDM the hu-PBL-NOD/SCID HIVE mice are subcutaneously (s.c) implanted with control (vehicle) or compound pellets (14 or 28 day slow release, Innovative Research). Initial experiments are designed to confirm the induction of virus-specific CTL in the hu PBL-NOD/SCID HIVE animals treated with IDO compounds. This is confirmed by tetramer staining and neuropathologic analyses of MDM elimination from the brain tissue. Then, the experiment is designed to analyze human lymphocyte reconstitution, humoral immune responses, and neuropathological alterations. In these experiments, animals are bled on day 7 and sacrificed at 14 and 21 days after i.c. injection of human MDM. Blood collected in EDTA-containing tubes is used for flow cytometry and plasma is used for detection of HIV-1 p24 using ELISA (Beckman Coulter™). HIV-1-specific antibodies are detected by Western blot tests according to the manufacturer instructions (Cambridge Biotech HIV-1 Western blot kit, Calypte Biomedical). Similar amount of virus-specific antibodies are detected in control and compound-treated animals. A total of three independent experiments can be performed using three different human leukocyte donors.

3. FACScan of Peripheral Blood and Spleen in hu PBL-NOD/SCID HIVE Mice

Two-color FACS analysis can be performed on peripheral blood at wk 1-3 and splenocytes at wk 2 and 3 after i.c. injection of human MDM. Cells are incubated with fluorochrome-conjugated monoclonal Abs (mAbs) to human CD4, CD8, CD56, CD3, IFN-γ (eBioscience) for 30 min at 4° C. To evaluate the cellular immune response, IFN-γ intracellular staining is performed in combination with anti-human CD8 and FITC-conjugated anti-mouse CD45 to exclude murine cells. To determine the Ag-specific CTL, allophycocyanin-conjugated tetramer staining for HIV-1$^{gag}$ (p17 (aa77-85) SLYNTVATL, SL-9) and HIV-1$^{pol}$ [(aa476-485) ILKEPVHGV, IL-9] is performed on phytohemaglutinin/interleukin-2 (PHA/IL-2)-stimulated splenocytes. Cells are stained following the recommendation of the NIH/National Institute of Allergy and Infections Disease, National Tetramer Core Facilities. Data were analyzed with a FACS Calibur™ using CellQuest software (Becton Dickinson Immunocytometry System).

4. Histopathology and Image Analyses

Brain tissue is collected at days 14 and 21 after i.c. injection of MDM, fixed in 4% phosphate-buffered paraformaldehyde and embedded in paraffin or frozen at −80° C. for later use. Coronal sections from the embedded blocks are cut in order to identify the injection site. For each mouse, 30-100 (5-μm-thick) serial sections are cut from the human MDM injection site and 3-7 slides (10 sections apart) are analyzed. Brain sections are deparaffinized with xylene and hydrated in gradient alcohols. Immunohistochemical staining follows a basic indirect protocol, using antigen retrieval by heating to 95° C. in 0.01 mol/L citrate buffer for 30 min for antigen retrieval. To identify human cells in mouse brains, mAb to vimentin (1:50, clone 3B4, Dako Corporation), which identifies all human leukocytes is used. Human MDM and CD8$^+$ lymphocytes are detected with CD68 (1:50 dilution, clone KP 1) and CD8 (1:50 dilution, clone 144B) antibodies, respectively. Virus-infected cells are labeled with mAb to HIV-1 p24 (1:10, clone Kal-1, all from Dako). Reactive murine microglial cells are detected with Iba-1 antibody (1:500, Wako). Expression of human IDO (huIDO) is visualized with Abs obtained from the Department of Cell Pharmacology, Central Research Institute, Graduate School of Medicine, Hokkaido University, Sapporo, Japan. Primary antibodies are detected with the appropriate biotinylated secondary antibodies and visualized with avidin-biotin complexes (Vectastain Elite ABC kit, Vector Laboratories) and horseradish peroxidase (HRP) coupled dextran polymer (EnVision, Dako Corporation). Immunostained sections are counterstained with Mayer's hematoxylin. Sections from which primary antibody is deleted or irrelevant IgG isotype is incorporated served as controls. Two independent observers in a blinded fashion count the numbers of CD8$^+$ lymphocytes, CD68$^+$ MDM and HIV-1 p24$^+$ cells in each section from each mouse. Light microscopic examination is performed with a Nikon Eclipse 800 microscope (Nikon Instruments Inc). Semi-quantitative analysis for Iba1 (percentage of area occupied by immunostaining) is carried out by computer-assisted image analysis (Image-Pro®Plus, Media Cybernetics) as previously described.

5. Statistical Analysis

Data can be analyzed using Prism (Graph Pad) with Student t-test for comparisons and ANOVA. P-values <0.05 were considered significant.

6. Reference

Poluektova L Y, Munn D H, Persidsky Y, and Gendelman H E (2002). Generation of cytotoxic T cells against virus-infected human brain macrophages in a murine model of HIV-1 encephalitis. *J. Immunol.* 168 (8):3941-9.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of suppressing immunosuppression or treating a disease selected from breast cancer, ovarian cancer, HIV infection, HCV infection, depression, Alzheimer's disease, Huntington's disease, trauma, age-related cataracts, organ transplant rejection, asthma, rheumatoid arthritis, multiple sclerosis, allergic inflammation, inflammatory bowel disease, psoriasis, and systemic lupus erythematosus in a patient, comprising administering to said patient a therapeutically effective amount of a compound of Formula I or Formula F28:

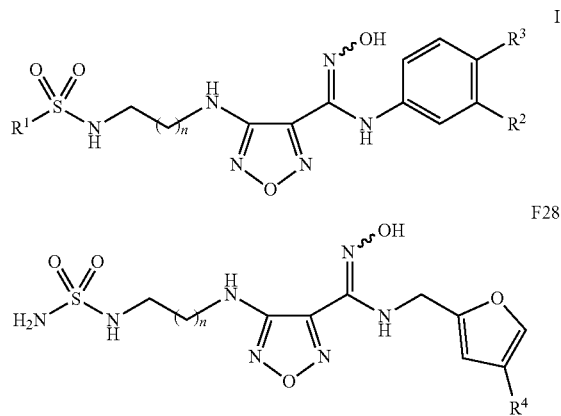

or a pharmaceutically acceptable salt thereof, wherein said treating refers to inhibiting the disease or ameliorating the disease; wherein:
$R^1$ is $NH_2$ or $CH_3$;
$R^2$ is Cl, Br, $CF_3$, $CH_3$, or CN;
$R^3$ is H or F;
$R^4$ is F, Cl, Br, or I; and
n is 1 or 2.

2. The method of claim 1, wherein said method is a method of treating a disease selected from breast cancer and ovarian cancer.

3. The method of claim 1, further comprising administering an anti-viral agent, an anti-cancer vaccine, an anti-CTLA-4 antibody, a chemotherapeutic, an immunosuppressant, radiation, an anti-tumor vaccine, an anti-viral vaccine, cytokine therapy, or a tyrosine kinase inhibitor to said patient.

4. The method of claim 3, wherein said cytokine therapy is IL-2.

5. The method of claim 3, wherein said chemotherapeutic is a cytotoxic agent.

6. The method of claim 1, wherein said compound is a compound of Formula I:

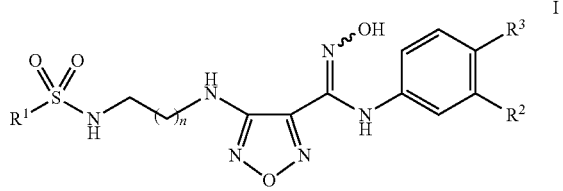

or a pharmaceutically acceptable salt thereof, wherein:
$R^1$ is $NH_2$ or $CH_3$;
$R^2$ is Cl, Br, $CF_3$, $CH_3$, or CN;
$R^3$ is H or F; and
n is 1 or 2.

7. The method of claim 6, wherein $R^1$ is $NH_2$.
8. The method of claim 6, wherein $R^2$ is Br.
9. The method of claim 6, wherein $R^3$ is F.
10. The method of claim 6, wherein n is 2.
11. The method of claim 6, wherein said compound is selected from:
4-({2-[(aminosulfonyl)amino]ethyl}amino)-N-(3-bromo-4-fluorophenyl)-N'-hydroxy-1,2,5-oxadiazole-3-carboximidamide;
N-(3-bromo-4-fluorophenyl)-N'-hydroxy-4-({2-[(methylsulfonyl)amino]ethyl}amino)-1,2,5-oxadiazole-3-carboximidamide;
4-({3-[(aminosulfonyl)amino]propyl}amino)-N-(3-bromo-4-fluorophenyl)-N'-hydroxy-1,2,5-oxadiazole-3-carboximidamide;
N-(3-bromo-4-fluorophenyl)-N'-hydroxy-4-({3-[(methylsulfonyl)amino]propyl}amino)-1,2,5-oxadiazole-3-carboximidamide;
4-({2-[(aminosulfonyl)amino]ethyl}amino)-N-(3-chloro-4-fluorophenyl)-N'-hydroxy-1,2,5-oxadiazole-3-carboximidamide;
N-(3-chloro-4-fluorophenyl)-N'-hydroxy-4-({2-[(methylsulfonyl)amino]ethyl}amino)-1,2,5-oxadiazole-3-carboximidamide;
4-({3-[(aminosulfonyl)amino]propyl}amino)-N-(3-chloro-4-fluorophenyl)-N'-hydroxy-1,2,5-oxadiazole-3-carboximidamide;
N-(3-chloro-4-fluorophenyl)-N'-hydroxy-4-({3-[(methylsulfonyl)amino]propyl}amino)-1,2,5-oxadiazole-3-carboximidamide;
4-({2-[(aminosulfonyl)amino]ethyl}amino)-N-[4-fluoro-3-(trifluoromethyl)phenyl]-N'-hydroxy-1,2,5-oxadiazole-3-carboximidamide;
N-[4-fluoro-3-(trifluoromethyl)phenyl]-N'-hydroxy-4-({2-[(methylsulfonyl)amino]ethyl}-amino)-1,2,5-oxadiazole-3-carboximidamide;
4-({3-[(aminosulfonyl)amino]propyl}amino)-N-[4-fluoro-3-(trifluoromethyl)phenyl]-N'-hydroxy-1,2,5-oxadiazole-3-carboximidamide;
N-[4-fluoro-3-(trifluoromethyl)phenyl]-N'-hydroxy-4-({3-[(methylsulfonyl)amino]propyl}-amino)-1,2,5-oxadiazole-3-carboximidamide;
4-({2-[(aminosulfonyl)amino]ethyl}amino)-N'-hydroxy-N-[3-(trifluoromethyl)phenyl]-1,2,5-oxadiazole-3-carboximidamide;
N'-hydroxy-4-({2-[(methylsulfonyl)amino]ethyl}amino)-N-[3-(trifluoromethyl)phenyl]-1,2,5-oxadiazole-3-carboximidamide;
4-({3-[(aminosulfonyl)amino]propyl}amino)-N'-hydroxy-N-[3-(trifluoromethyl)phenyl]-1,2,5-oxadiazole-3-carboximidamide;
N'-hydroxy-4-({3-[(methylsulfonyl)amino]propyl}amino)-N-[3-(trifluoromethyl)phenyl]-1,2,5-oxadiazole-3-carboximidamide;
N-(4-fluoro-3-methylphenyl)-N'-hydroxy-4-({2-[(methylsulfonyl)amino]ethyl}amino)-1,2,5-oxadiazole-3-carboximidamide;
4-({2-[(aminosulfonyl)amino]ethyl}amino)-N-(3-cyano-4-fluorophenyl)-N'-hydroxy-1,2,5-oxadiazole-3-carboximidamide; and
N-(3-cyano-4-fluorophenyl)-N'-hydroxy-4-({2-[(methylsulfonyl)amino]ethyl}amino)-1,2,5-oxadiazole-3-carboximidamide;
or a pharmaceutically acceptable salt thereof.

12. A method of suppressing immunosuppression or treating a disease selected from breast cancer, ovarian cancer, HIV infection, HCV infection, depression, Alzheimer's disease, Huntington's disease, trauma, age-related cataracts, organ transplant rejection, asthma, rheumatoid arthritis, multiple sclerosis, allergic inflammation, inflammatory bowel disease, psoriasis, and systemic lupus erythematosus in a patient, comprising administering to said patient a therapeutically effective amount of 4-({2-[(aminosulfonyl)amino]ethyl}amino)-N-(3-bromo-4-fluorophenyl)-N'-hydroxy-1,2,5-oxadiazole-3-carboximidamide, or a pharmaceutically acceptable salt thereof, wherein said treating refers to inhibiting the disease or ameliorating the disease.

13. The method of claim 12, further comprising administering an anti-viral agent, an anti-cancer vaccine, an anti-CTLA-4 antibody, a chemotherapeutic, an immunosuppressant, radiation, an anti-tumor vaccine, an anti-viral vaccine, cytokine therapy, or a tyrosine kinase inhibitor to said patient.

14. The method of claim 13, wherein said cytokine therapy is IL-2.

15. The method of claim 13, wherein said chemotherapeutic is a cytotoxic agent.

16. The method of claim 12, wherein said compound is 4-({2-[(aminosulfonyl)amino]ethyl}amino)-N-(3-bromo-4-fluorophenyl)-N'-hydroxy-1,2,5-oxadiazole-3-carboximidamide.

17. The method of claim 1, wherein said compound is a compound of Formula F28:

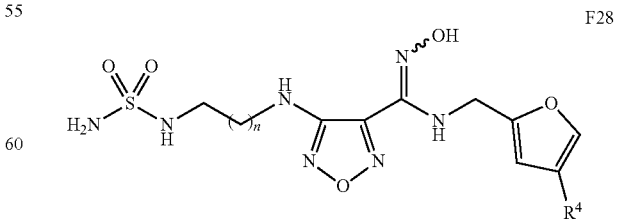

or a pharmaceutically acceptable salt thereof; wherein:
$R^4$ is F, Cl, Br, or I; and
n is 1 or 2.

18. A method of suppressing immunosuppression or treating a disease selected from breast cancer, ovarian cancer, HIV infection, HCV infection, depression, Alzheimer's disease, Huntington's disease, trauma, age-related cataracts, organ transplant rejection, asthma, rheumatoid arthritis, multiple sclerosis, allergic inflammation, inflammatory bowel disease, psoriasis, and systemic lupus erythematosus in a patient, comprising administering to said patient a therapeutically effective amount of 4-({2-[(aminosulfonyl)amino]ethyl}amino)-N-[(4-bromo-2-furyl)methyl]-N'-hydroxy-1,2,5-oxadiazole-3-carboximidamide, or a pharmaceutically acceptable salt thereof, wherein said treating refers to inhibiting the disease or ameliorating the disease.

19. The method of claim 18, further comprising administering an anti-viral agent, an anti-cancer vaccine, an anti-CTLA-4 antibody, a chemotherapeutic, an immunosuppressant, radiation, an anti-tumor vaccine, an anti-viral vaccine, cytokine therapy, or a tyrosine kinase inhibitor to said patient.

20. The method of claim 19, wherein said cytokine therapy is IL-2.

21. The method of claim 19, wherein said chemotherapeutic is a cytotoxic agent.

22. The method of claim 17, wherein said compound is 4-({2-[(aminosulfonyl)amino]ethyl}amino)-N-[(4-chloro-2-furyl)methyl]-N'-hydroxy-1,2,5-oxadiazole-3-carboximidamide, or a pharmaceutically acceptable salt thereof.

23. A process for preparing a compound of Formula F15:

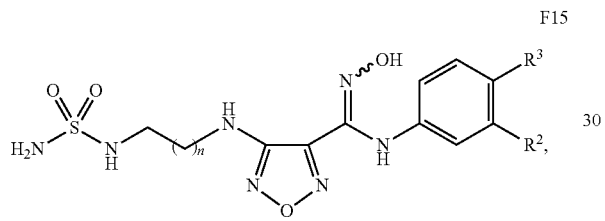

F15 or a salt thereof, wherein $R^2$ is Cl, Br, $CF_3$, $CH_3$, or CN; $R^3$ is H or F; and n is 1 or 2, comprising:
a) reacting a compound of Formula F12:

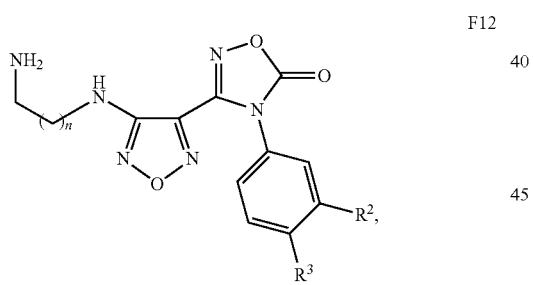

F12 or a salt thereof, with sulfamide and an organic base to afford a compound of Formula F14:

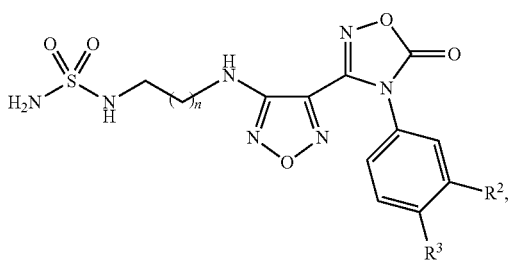

F14 or a salt thereof, and
b) reacting said compound of Formula F14, or a salt thereof, with a base to afford said compound of Formula F15.

24. A process for preparing a compound of Formula F15:

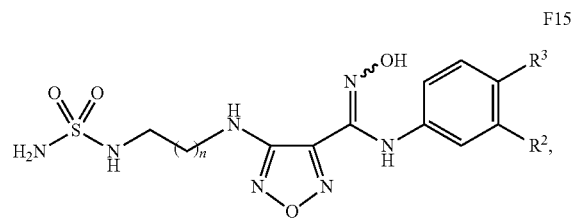

F15 or a salt thereof, wherein $R^2$ is Cl, Br, $CF_3$, $CH_3$, or CN; $R^3$ is H or F; and n is 1 or 2, comprising:
a) reacting a compound of Formula F13:

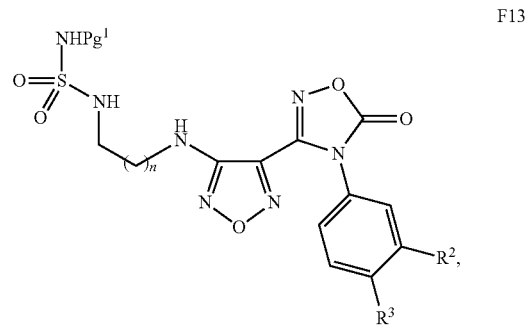

F13 or a salt thereof, wherein $Pg^1$ is an amino protecting group, with an amino deprotecting agent to afford a compound of Formula F14:

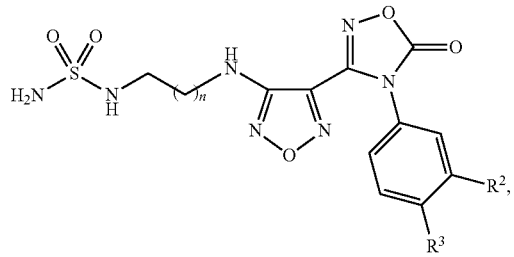

F14 or a salt thereof; and
b) reacting said compound of Formula F14 with a base to afford said compound of Formula F15.

25. The method of claim 12, wherein said method is a method of treating breast cancer.

26. The method of claim 12, wherein said method is a method of treating ovarian cancer.

27. The method of claim 12, wherein said method is a method of treating HIV infection.

28. The method of claim 12, wherein said method is a method of treating HCV infection.

29. The method of claim 12, wherein said method is a method of treating depression.

30. The method of claim 12, wherein said method is a method of treating Alzheimer's disease.

31. The method of claim 12, wherein said method is a method of treating Huntington's disease.

32. The method of claim 12, wherein said method is a method of treating trauma.

33. The method of claim 12, wherein said method is a method of treating age-related cataracts.

34. The method of claim 12, wherein said method is a method of treating organ transplant rejection.

35. The method of claim 12, wherein said method is a method of treating asthma.

36. The method of claim 12, wherein said method is a method of treating rheumatoid arthritis.

37. The method of claim 12, wherein said method is a method of treating multiple sclerosis.

38. The method of claim 12, wherein said method is a method of treating allergic inflammation.

39. The method of claim 12, wherein said method is a method of treating inflammatory bowel disease.

40. The method of claim 12, wherein said method is a method of treating psoriasis.

41. The method of claim 12, wherein said method is a method of treating systemic lupus erythematosus.

42. The method of claim 18, wherein said method is a method of treating breast cancer.

43. The method of claim 18, wherein said method is a method of treating ovarian cancer.

44. The method of claim 18, wherein said method is a method of treating HIV infection.

45. The method of claim 18, wherein said method is a method of treating HCV infection.

46. The method of claim 18, wherein said method is a method of treating depression.

47. The method of claim 18, wherein said method is a method of treating Alzheimer's disease.

48. The method of claim 18, wherein said method is a method of treating Huntington's disease.

49. The method of claim 18, wherein said method is a method of treating trauma.

50. The method of claim 18, wherein said method is a method of treating age-related cataracts.

51. The method of claim 18, wherein said method is a method of treating organ transplant rejection.

52. The method of claim 18, wherein said method is a method of treating asthma.

53. The method of claim 18, wherein said method is a method of treating rheumatoid arthritis.

54. The method of claim 18, wherein said method is a method of treating multiple sclerosis.

55. The method of claim 18, wherein said method is a method of treating allergic inflammation.

56. The method of claim 18, wherein said method is a method of treating inflammatory bowel disease.

57. The method of claim 18, wherein said method is a method of treating psoriasis.

58. The method of claim 18, wherein said method is a method of treating systemic lupus erythematosus.

59. The method of claim 1, wherein the method is a method of treating breast cancer or ovarian cancer, wherein said method further comprises administering an anti-CTLA-4 antibody to said patient.

60. The method of claim 1, wherein the method is a method of treating breast cancer or ovarian cancer, wherein said method further comprises administering an anti-PD-1 antibody to said patient.

61. The method of claim 12, wherein the method is a method of treating breast cancer, wherein said method further comprises administering an anti-CTLA-4 antibody to said patient.

62. The method of claim 12, wherein the method is a method of treating ovarian cancer, wherein said method further comprises administering an anti-CTLA-4 antibody to said patient.

63. The method of claim 12, wherein the method is a method of treating breast cancer, wherein said method further comprises administering an anti-PD-1 antibody to said patient.

64. The method of claim 12, wherein the method is a method of treating ovarian cancer, wherein said method further comprises administering an anti-PD-1 antibody to said patient.

65. The method of claim 18, wherein the method is a method of treating breast cancer, wherein said method further comprises administering an anti-CTLA-4 antibody to said patient.

66. The method of claim 18, wherein the method is a method of treating ovarian cancer, wherein said method further comprises administering an anti-CTLA-4 antibody to said patient.

67. The method of claim 18, wherein the method is a method of treating breast cancer, wherein said method further comprises administering an anti-PD-1 antibody to said patient.

68. The method of claim 18, wherein the method is a method of treating ovarian cancer, wherein said method further comprises administering an anti-PD-1 antibody to said patient.

* * * * *

UNITED STATES PATENT AND TRADEMARK OFFICE
CERTIFICATE OF CORRECTION

PATENT NO. : 8,796,319 B2  
APPLICATION NO. : 13/294711  
DATED : August 5, 2014  
INVENTOR(S) : Andrew P. Combs et al.

Page 1 of 1

It is certified that error appears in the above-identified patent and that said Letters Patent is hereby corrected as shown below:

On the Title Page

Page 2, Column 2 (Other Publications), Line 55, delete "antihypertenstive" and insert -- antihypertensive --.

Page 3, Column 1 (Other Publications), Line 22, delete "Compaunds" and insert -- Compounds --.

Page 3, Column 1 (Other Publications), Line 28, delete "Compaunds" and insert -- Compounds --.

Page 4, Column 1 (Other Publications), Line 28, delete "3 8" and insert -- 38 --.

Page 4, Column 1 (Other Publications), Line 39, delete "Struktumoi" and insert -- Strukturnoi --.

Page 4, Column 2 (Other Publications), Line 5, delete "Zelinskii" and insert -- Zelinsky --.

Page 4, Column 2 (Other Publications), Line 18, delete "pheny1" and insert -- phenyl --.

Page 4, Column 2 (Other Publications), Line 24, delete "Cycloaddtion" and insert -- Cycloaddition --.

In the Claims

Column 104, Line 1, Claim 11, delete "trifluor omethyl" and insert -- trifluoromethyl --.

Column 104, Line 1, Claim 11, delete "hydroxy -4" and insert -- hydroxy-4 --.

Signed and Sealed this  
Twenty-seventh Day of April, 2021

Drew Hirshfeld  
*Performing the Functions and Duties of the  
Under Secretary of Commerce for Intellectual Property and  
Director of the United States Patent and Trademark Office*